(12) United States Patent
LaVoie et al.

(10) Patent No.: US 8,796,300 B2
(45) Date of Patent: Aug. 5, 2014

(54) THERAPEUTIC COMPOUNDS

(75) Inventors: Edmond J. LaVoie, New Brunswick, NJ (US); Joseph E. Rice, New Brunswick, NJ (US); Suzanne G. Rzuczek, New Brunswick, NJ (US); Daniel S. Pilch, Somerset, NJ (US)

(73) Assignees: Rutgers, the State University of New Jersey, New Brunswick, NJ (US); University of Medicine and Dentistry of New Jersey, Somerset, NJ (US)

( * ) Notice: Subject to any disclaimer, the term of this patent is extended or adjusted under 35 U.S.C. 154(b) by 11 days.

(21) Appl. No.: 13/508,012

(22) PCT Filed: Nov. 5, 2010

(86) PCT No.: PCT/US2010/055709
§ 371 (c)(1), (2), (4) Date: May 3, 2012

(87) PCT Pub. No.: WO2011/057126
PCT Pub. Date: May 12, 2011

(65) Prior Publication Data
US 2012/0238595 A1    Sep. 20, 2012

Related U.S. Application Data

(60) Provisional application No. 61/258,475, filed on Nov. 5, 2009.

(51) Int. Cl.
| C07D 513/22 | (2006.01) |
| A61K 31/429 | (2006.01) |
| A61K 45/00 | (2006.01) |
| A61P 43/00 | (2006.01) |

(52) U.S. Cl.
USPC ............................ 514/279; 514/375; 540/456

(58) Field of Classification Search
USPC ................................... 540/456; 514/279, 375
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,851,524 A | 7/1989 | Brois et al. |
| 4,938,949 A | 7/1990 | Borch et al. |
| 4,992,478 A | 2/1991 | Geria |
| 8,093,235 B2 | 1/2012 | Lavoie et al. |
| 2009/0156627 A1 | 6/2009 | Lavoie et al. |
| 2011/0230531 A1 | 9/2011 | Lavoie et al. |
| 2012/0046234 A1 | 2/2012 | Lavoie et al. |
| 2012/0071527 A1 | 3/2012 | Lavoie et al. |

FOREIGN PATENT DOCUMENTS

| CA | 2436942 A1 | 6/2002 |
| EP | 1350794 A1 | 10/2003 |
| EP | 1602659 A1 | 12/2005 |
| EP | 2186810 A1 | 5/2010 |
| JP | 11-180997 A | 7/1999 |
| JP | 2006-316008 A | 11/2006 |
| WO | WO 97/48708 A1 | 12/1997 |
| WO | WO 02/48153 A1 | 6/2002 |
| WO | WO 2005/000880 A2 | 1/2005 |
| WO | WO 2007/127173 A2 | 11/2007 |
| WO | WO 2007/127173 A4 | 11/2007 |
| WO | WO 2009/018549 A1 | 2/2009 |
| WO | WO 2009/018551 A2 | 2/2009 |

OTHER PUBLICATIONS

Barbieri, C.M., et al., "Defining the mode, energetic and specificity with which a macrocyclic hexaoxazole binds to human telomeric G-quadruplex DNA", *Nucleic Acids Res.*, 35(10), 3272-3286 (2007).
Bertram et al., "Concise synthesis of stereodefined, thiazole-containing cyclic hexa- and octapeptide relatives of the Lissoclinums, via cyclooligomerisation reactions", *Tetrahedron* vol. 59, No. 35, 6979-6990 (2003).
Binz, N., et al., "Telomerase inhibition, telomere shortening, cell growth suppression and induction of apoptosis by telomestatin in childhood neuroblastoma cells", *Eur. J. Cancer*, 41(18), 2873-2881 (2005).
Chattopadhyay, S.K. and S. Biswas, "Convergent synthesis of a 24-membered macrocyclic hexaoxazole derivative related to the novel telomerase inhibitor telomestatin", *Tetrahedron Letters*, 47(45), 7897-7900 (2006).
Chattopadhyay, "Efficient Construction of Doubly Functionalized Trisoxazole Derivative Relevant to the Synthesis of the Novel Telomerase Inhibitor Telomestatin and its Analogues", *Synthesis*, 1289-1294 (2006).
Database Accession No. 2006:1228832, Database Caplus [Online] Chemical Abstracts Service, Columbus, Ohio, US; XP002659478, 9 pages (2006).
Deeley, "Synthesis and establishment of stereochemistry of the unusual polyoxazole-thiazole based cyclopeptide YM-216391 isolated from *Streptomyces nobilis*", *Chem. Communications*, 797-799 (2005).

(Continued)

*Primary Examiner* — Bruck Kifle
(74) *Attorney, Agent, or Firm* — Viksnins Harris & Padys PLLP

(57) ABSTRACT

The invention provides compounds of formula (I) wherein u, d, v, m, n, $R^1$, W, X, Y, and Z have any values defined herein, as well as salts thereof. The compounds have activity as anti-proliferative agents.

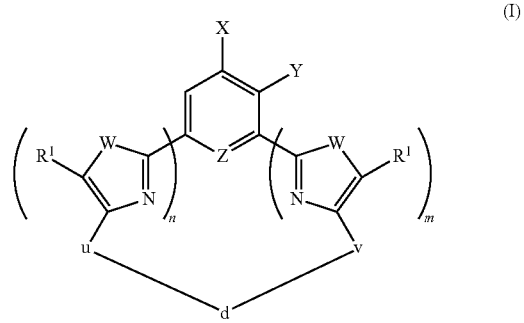

16 Claims, No Drawings

(56) References Cited

OTHER PUBLICATIONS

DOI, "Total Synthesis of (R)-Telomestatin", *Organic Letters*, 8, 4165-4167 (2006).
Endoh, "Useful Synthesis of Longer Array Oxazole Rings for Telomestatin", *Heterocycles*, 60, 1567-2572 (2003).
European Patent Office, Supplementary European Search Report and European Opinion, Application No. 10829184.0, 9 pages, Apr. 5, 2013.
Han et al., "G-quadruplex DNA: a potential target for anti-cancer drug design", *TiPS*, vol. 21, 136-142 (2000).
Jantos, "Oxazole-Based Peptide Macrocycles: A New Class of G-Quadruplex Binding Ligands", *J. Am. Chem. Soc.*, 128, 13662-13663, (2006).
Kim, et al. "Telomestatin, a potent telomerase inhibitor that interacts quite specifically with the human telomeric intramolecular g-quadruplex", *J. Am. Chem. Soc.*, 124, 2098-2099 (2002).
Kim, M., et al., "The Different Biological Effects of Telomestatin and TMPyP4 Can Be Attributed to Their Selectivity for Interaction with Intramolecular or Intermolecular G-Quadruplex Structures", *Cancer Res.*, 63, 3247-3256, (2003).
Liu, W., et al., "Binding of G-Quadruplex-interactive Agents to Distinct G-Quadruplexes Induces Different Biological Effects in MiaPaCa Cells", *Nucleosides, Nucleotides, and Nucleic Acids*, 24, 1801-1815, (2005).
Lucke et al., "Designing supramolecular structures from models of cyclic peptide scaffolds with heterocyclic constraints", *Journal of Molecular Graphics and Modeling*, vol. 21, pp. 341-355 (2003).
Marson, C.M. and M. Saadi, "Synthesis of the penta-oxazole core of telomestatin in a convergent approach to poly-oxazolemacrocycles", *Organic & Biomolecular Chemistry*, 4(21), 3892-3893 (2006).
Minhas, G.S. et al., "Synthesis and G-quadruplex stabilizing properties of a series of oxazole-containing macrocycles", *Bioorganic & Medicinal Chemistry Letters*, 16(15), 3891-3895 (2006).
Nakajima, "Telomerase inhibition enhances apoptosis in human acute leukemia cells: possibility of antitelomerase therapy", *Leukemia*, 17, 560-567 (2003).
Patent Cooperation Treaty, International Search Report and Written Opinion, PCT/US10/55709, 11 pages, Jan. 31, 2011.
Rzuczek et al., "Macrocyclic Pyridyl Polyoxazoles: Selective RNA and DNA G-Quadruplex Ligands as Antitumor Agents", *J. Med. Chem.*, 53, 3632-3644 (2010).
Satyanarayana, M., et al., "Ring-closing metathesis for the synthesis of a highly G-quadruplex selective macrocyclic hexaoxazole having enhanced cytotoxic potency", *Bioorg. Med. Chem. Lett.*, 18(13), 3802-3804 (2008).
Satyanarayana, et al., "Macrocyclic hexaoxazoles: Influence of aminoalkyl substituents on RNA and DNA G-quadruplex stabilization and cytotoxicity", *Bioorg. Med. Chem. Lett.*, vol. 20, 3150-3154 (2010).
Shin-Ya, K., et al., "Telomestatin, a Novel Telomerase Inhibitor from *Streptomyces anulatus*", *J. Am. Chem. Soc.*, 123(6), 1262-1263, (2001).
Singh et al., "Novel cylindrical, conical, and macrocyclic peptides from the cyclooligomerization of functionalized thiazole amino acids", *J. Am. Chem. Soc.*, vol. 123, 333-334, including 13 supplemental pages (2001).
Sohda, K, et al., "YM-216391, a Novel Cytotoxic Cyclic Peptide from *Streptomyces nobilis*. I. Fermentation, Isolation and Biological Activities", *J. Antibiotics*, 58(1), 27-31, (2005).
Sohda, K., et al., "YM-216391, a novel cytotoxic cyclic peptide from *Streptomyces nobilis*. II. Physico-chemical properties and structure elucidation", *J. Antibiot.* (Tokyo), 58(1), 32-36, (2005).
Tauchi, T., et al., "Activity of a novel G-quadruplex-interactive telomerase inhibitor, telomestatin (SOT-095), against human leukemia cells: involvement of ATM-dependent DNA damage response pathways", *Oncogene*, 22, 5338-5347, (2003).
Tauchi et al., "Telomerase inhibition with a novel G-quadruplex-interactive agent, telomestatin: in vitro and in vivo studies in acute leukemia", *Oncogene*, 25, 5719-5725 (2006).
Wang, "First Total Synthesis of Leucamide A", *J. Org. Chem.*, 68, 1636-1639, (2003).

THERAPEUTIC COMPOUNDS

PRIORITY OF INVENTION

This application claims priority from U.S. Provisional Application No. 61/258,475 filed Nov. 5, 2009, which application is incorporated by reference.

BACKGROUND OF THE INVENTION

A diverse array of compounds, including anthraquinones, acridines, cationic porphyrins, perylenes, thidium derivatives, fluorenones, pentacyclic acridinium salts, fluoroquinophenoxazines, and other specific miscellaneous polycyclic compounds, have been reported to stabilize G-quadruplex DNA. Most of these compounds have limited selectivity for G-quadruplex vs. duplex DNA.

Telomestatin is a natural product isolated from *Streptomyces anulatus* 3533-SV4 (Shinya et al., *J. Am. Chem. Soc.*, 2001, 123, 1262-1263). At the time of its discovery, telomestatin was viewed as the most potent inhibitor of telomerase. In vitro, telomestatin stabilizes G-quadruplex vs. duplex DNA in a 70:1 ratio (Kim et al., *Cancer Res.*, 2003, 63, 3247-3256). It has been suggested that telomestatin also inhibits telomerase function in vivo, since cells treated with the natural product exhibit a cellular senescence phenotype. Like telomere dysfunction, telomestatin activates the ATM signaling pathway. While the precise mechanism by which telomestatin interacts with a G-quadruplex has not been definitively elucidated, telomestatin does suppress the plating efficiency of K62 leukemia cells but has a much lesser effect on burst-forming units-erythrocyte (BFU-E) and colony-forming units-granulocyte/macrophage (CFU-GM) from natural bone marrow CD34-positive cells (Tauchi et al., *Oncogene*, 2003, 22, 5338-5347).

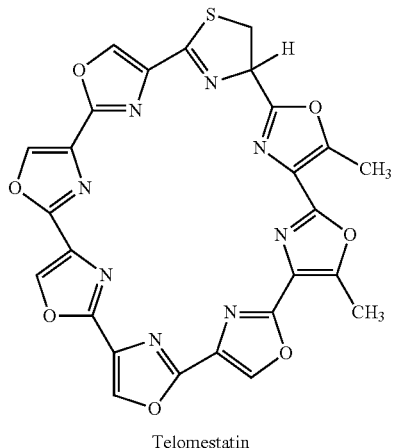 [SMILES: Cc1oc2nc1-c1nc(co1)-c1nc(co1)-c1nc(co1)-c1nc(co1)-c1nc(co1)C1=NC(CS1)c1nc-2c(C)o1]

Telomestatin

The anticancer potential of telomestatin has been reported to be associated with its telomerase inhibitory activity ($IC_{50}$ 5 nM) and in its ability to enhance apoptosis. Telomestatin has been evaluated for cytotoxicity in the human neuroblastoma cell lines SK-N-AS, LAN5, WAC2, and LAN1 with $IC_{50}$ values of 0.8, 2.5, 3.2, and 4.0 µM respectively (Binz et al., *Eur. J. Cancer*, 2005, 41, 2873-2881) and in the human pancreatic carcinoma MiaPaCa with an $IC_{50}$ value of 0.5 µM (Liu et al., *Nucleosides, Nucleotides, and Nucleic Acids*, 2005, 24, 1801-1815). The in vivo activity of telomestatin has also been evaluated in xenographs of acute human leukemia (U937) cells in mice (Tauchi et al., *Oncogene*, 2006, 25, 5719-5725).

Another macrocyclic polyoxazole, YM-216391 isolated from *Streptomyces nobilis* is active against the human breast cancer cell lines HBC-4, BSY-1, HBC-5, MCF-7, and MDA-MB-231 with $GI_{50}$ values ranging from 15-33 nM (Sohda, K-y., et al., *J. Antibiotics*, 2005, 58, 27-31 and Sohda, K-y., et al., Hiramoto, M., Suzumura, K-i., Takebayashi, Y., Suzuki, K-i., Tanaka, A. *J. Antibiotics*, 2005, 58, 32-36).

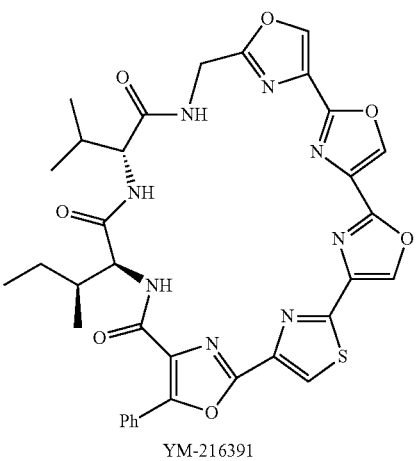

YM-216391

The mechanism of action of YM-216391 has not yet been elucidated.

Certain specific compounds have also been reported to stabilize G-quadruplex DNA and RNA (Barbieri, C., *Nucleic Acids Research*, 2007, 35(10) 3272-3286).

International Patent Applications Publication Numbers WO2007/127173, WO2009/018551, and WO2009/018549 disclose compounds that are reported to stabilize G-quadruplex DNA. However, the commercial development of these compounds may be less desirable due to the difficult synthetic processes and low yields associated with their preparation.

Currently, there is a need for novel therapeutic agents and therapeutic methods that are useful for treating diseases such as cancer. Such agents may have improved binding affinity for G-quadruplex DNA and/or they may have advantageous drug-like properties. Additionally, there is a need for compounds that stabilize G-quadruplex DNA, which can be prepared in commercially useful quantities using commercially viable starting materials and processes.

SUMMARY OF THE INVENTION

The present invention provides compounds that stabilize G-quadruplex DNA and RNA. The present invention also provides compounds that possess anti-cancer properties. Accordingly there is provided a compound of the invention which is compound of formula (I):

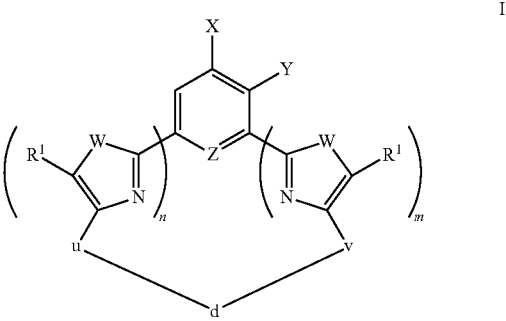

wherein:
Z is CH or N;
each W is independently NH, S, or O;

n is 1 and m is 3; or n is 2 and m is 2; or n is 3 and m is 1; or n is 4 and m is 0;

X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;

Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;

each $R^1$ is independently H or $(C_1-C_6)$alkyl wherein any $(C_1-C_6)$alkyl of $R^1$ is optionally is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{a1}R_{b1}$, $-C(=O)NR_{a1}R_{b1}$, and $-NR_{a1}C(=O)-R_{c1}$;

each $R_a$ and $R_b$ is independently H, $(C_1-C_6)$alkyl, $(C_1-C_6)$alkanoyl, or aryl$(C_1-C_6)$alkyl; or $R_a$ and $R_b$ together with the nitrogen to which they are attached form an N-linked heterocycle that is optionally substituted with one or more oxo;

each $R_c$ is $(C_1-C_3)$haloalkyl;

each $R_{a1}$ and $R_{b1}$ is independently H, $(C_1-C_6)$alkyl, $(C_1-C_6)$alkanoyl, or aryl$(C_1-C_6)$alkyl; or $R_{a1}$ and $R_{b1}$ together with the nitrogen to which they are attached form an N-linked heterocycle that is optionally substituted with one or more oxo;

each $R_{c1}$ is halo$(C_1-C_6)$alkyl, $(C_1-C_6)$alkoxy or aryl$(C_1-C_6)$alkoxy; and -u-d-v- taken together form an organic radical that comprises a 9 membered chain that taken together with the remainder of formula I forms a compound that comprises a 24 membered ring;

or a salt thereof.

The invention also provides a pharmaceutical composition comprising a compound of formula (I), or a pharmaceutically acceptable salt thereof, in combination with a pharmaceutically acceptable diluent or carrier.

Additionally, the invention provides a therapeutic method for treating cancer comprising administering to a mammal (e.g., a human male or female) in need of such therapy, an effective amount of a compound of formula (I), or a pharmaceutically acceptable salt thereof.

The invention provides a compound of formula (I) or a pharmaceutically acceptable salt thereof for use in medical therapy (e.g., for use in treating cancer), as well as the use of a compound of formula (I) or a pharmaceutically acceptable salt thereof for the manufacture of a medicament useful for the treatment of cancer in a mammal, such as a human.

The invention also provides a compound of formula (I) or a pharmaceutically acceptable salt thereof for use in the prophylactic or therapeutic treatment of cancer.

The invention also provides a method to stabilize G-quadruplex DNA or RNA comprising contacting the G-quadruplex DNA or RNA with a compound of formula I or a pharmaceutically acceptable salt thereof.

The invention also provides a method to stabilize G-quadruplex DNA comprising contacting the G-quadruplex DNA with a compound of formula I or a pharmaceutically acceptable salt thereof.

The invention also provides a method to stabilize G-quadruplex RNA comprising contacting the G-quadruplex RNA with a compound of formula I or a pharmaceutically acceptable salt thereof.

The invention also provides processes and intermediates disclosed herein that are useful for preparing compounds of formula (I) or salts thereof.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

Aryl denotes a phenyl radical or an ortho-fused bicyclic carbocyclic radical having about nine to ten ring atoms in which at least one ring is aromatic. Examples of aryl include phenyl, indenyl, and naphthyl.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) and quinolyl (or its N-oxide).

The term "heterocycle" refers to a monovalent saturated or partially unsaturated cyclic non-aromatic group which contains at least one heteroatom, preferably 1 to 4 heteroatoms, selected from nitrogen ($NR_x$, wherein $R_x$ is hydrogen, alkyl, or a direct bond at the point of attachment of the heterocycle group), sulfur, phosphorus, and oxygen within at least one cyclic ring and which may be monocyclic or multi-cyclic. Such heterocycle groups preferably contain from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, phthalimidyl (e.g. phthalimid-2-yl), quinuclidinyl and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1, -pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be pyridyl.

The term haloalkyl refers to an alkyl as defined above wherein at least one hydrogen and up to all of hydrogen atoms of the alkyl group are each independently replaced with a halo. A $(C_1-C_3)$haloalkyl is a haloalkyl which comprises one to three carbon atoms. Specific groups include trifluoromethyl, perfluoropropane and dichlorofluoromethane.

In specific embodiment, the invention the compound of formula I is a compound of formula II:

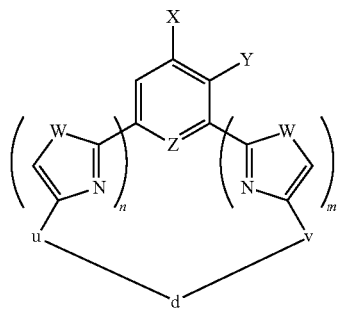

wherein:
Z is CH or N;
each W is independently NH, S, or O;
n is 1 and m is 3; or n is 2 and m is 2; or n is 3 and m is 1; or n is 4 and m is 0;
X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —$NR_aR_b$, —$C(=O)NR_aR_b$, or —$NR_aC(=O)$—$R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_aR_b$, —$C(=O)NR_aR_b$, and —$NR_aC(=O)$—$R_c$;
Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —$NR_aR_b$, —$C(=O)NR_aR_b$, or —$NR_aC(=O)$—$R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_aR_b$, —$C(=O)NR_aR_b$, and —$NR_aC(=O)$—$R_c$;
each $R_a$ and $R_b$ is independently H, $(C_1-C_6)$alkyl, $(C_1-C_6)$alkanoyl, or aryl$(C_1-C_6)$alkyl; or $R_a$ and $R_b$ together with the nitrogen to which they are attached form an N-linked heterocycle that is optionally substituted with one or more oxo;
each $R_c$ is $(C_1-C_3)$alkyl; and
-u-d-v- taken together form an organic radical that comprises a 9 membered chain that taken together with the remainder of formula I forms a compound that comprises a 24 membered ring;
or a salt thereof.

The specific embodiments and values listed below are embodiments and values for compounds of formula I and formula II.

In one specific embodiment of the invention n is 1 and m is 3.

In one specific embodiment of the invention n is 2 and m is 2.

In one specific embodiment of the invention n is 3 and m is 1.

In one specific embodiment of the invention u is —$C(=O)NHCH_2$—.

In one specific embodiment of the invention v is —$C(=O)NHCH_2$—.

In one specific embodiment of the invention u is —$C(=O)NHCH_2CH_2$—.

In one specific embodiment of the invention v is —$C(=O)NHCH_2CH_2$—.

In one specific embodiment of the invention both u and v are —$C(=O)NHCH_2$—.

In one specific embodiment of the invention u is —$C(=O)NHCH_2$— and v is —$C(=O)NHCH_2CH_2$—.

In one specific embodiment of the invention u is —$C(=O)NHCH_2CH_2$— and v is —$C(=O)NHCH_2$—.

In one specific embodiment of the invention both u and v are —$C(=O)NHCH_2CH_2$—.

In one specific embodiment of the invention u is —$C(=O)NHCR_oR_p$—; wherein $R_o$ and $R_p$ are each independently selected from H, $(C_1-C_6)$alkyl, aryl and aryl$(C_1-C_6)$alkyl; and wherein any $(C_1-C_6)$alkyl, aryl or aryl$(C_1-C_6)$alkyl of $R_o$ or $R_p$ is optionally substituted with one or more groups independently selected from OH, halo and $NR_sR_t$; wherein $R_s$ and $R_t$ are each independently H or $(C_1-C_6)$alkyl.

In one specific embodiment of the invention u is —$C(=O)NHCHR_o$—; wherein $R_o$ is selected from H, $(C_1-C_6)$alkyl, aryl and aryl$(C_1-C_6)$alkyl; and wherein any $(C_1-C_6)$alkyl, aryl or aryl$(C_1-C_6)$alkyl of $R_o$ is optionally substituted with one or more groups independently selected from OH, halo and $NR_sR_t$; wherein $R_s$ and $R_t$ are each independently H or $(C_1-C_6)$alkyl.

In one specific embodiment of the invention v is —$C(=O)NHCR_oR_p$—; wherein $R_o$ and $R_p$ are each independently selected from H, $(C_1-C_6)$alkyl, aryl and aryl$(C_1-C_6)$alkyl; and wherein any $(C_1-C_6)$alkyl, aryl or aryl$(C_1-C_6)$alkyl of $R_o$ or $R_p$ is optionally substituted with one or more groups independently selected from OH, halo and $NR_sR_t$; wherein $R_s$ and $R_t$ are each independently H or $(C_1-C_6)$alkyl.

In one specific embodiment of the invention v is —$C(=O)NHCHR_o$—; wherein $R_o$ is selected from H, $(C_1-C_6)$alkyl, aryl and aryl($C_1$-$C_6$)alkyl; and wherein any ($C_1$-$C_6$)alkyl, aryl or aryl($C_1$-$C_6$)alkyl of $R_o$ is optionally substituted with one or more groups independently selected from OH, halo and $NR_sR_t$; wherein $R_s$ and $R_t$ are each independently H or ($C_1$-$C_6$)alkyl.

In one specific embodiment of the invention u is —C(=O)NH($CR_oR_p$)$_2$—; wherein each $R_o$ and $R_p$ are independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ or $R_p$ is optionally substituted with one or more groups independently selected from OH, halo and $NR_sR_t$; wherein $R_s$ and $R_t$ are each independently H or ($C_1$-$C_6$)alkyl.

In one specific embodiment of the invention u is —C(=O)NH(CHR$_o$)$_2$—; wherein each $R_o$ is independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ is optionally substituted with one or more groups independently selected from OH, halo and $NR_sR_t$; wherein $R_s$ and $R_t$ are each independently H or ($C_1$-$C_6$)alkyl.

In one specific embodiment of the invention v is —C(=O)NH($CR_oR_p$)$_2$—; wherein each $R_o$ and $R_p$ are independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ or $R_p$ is optionally substituted with one or more groups independently selected from OH, halo and $NR_sR_t$; wherein $R_s$ and $R_t$ are each independently H or ($C_1$-$C_6$)alkyl.

In one specific embodiment of the invention v is —C(=O)NH(CHR$_o$)$_2$—; wherein each $R_o$ is independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ is optionally substituted with one or more groups independently selected from OH, halo and $NR_sR_t$; wherein $R_s$ and $R_t$ are each independently H or ($C_1$-$C_6$)alkyl.

In one specific embodiment of the invention both u and v are —C(=O)NHCR$_o$R$_p$—; wherein each $R_o$ and $R_p$ are independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ or $R_p$ is optionally substituted with one or more groups independently selected from OH, halo and $NR_sR_t$; wherein $R_s$ and $R_t$ are each independently H or ($C_1$-$C_6$)alkyl.

In one specific embodiment of the invention u is —C(=O)NHCR$_o$R$_p$— and v is —C(=O)NH($CR_oR_p$)$_2$—; wherein each $R_o$ and $R_p$ are independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ or $R_p$ is optionally substituted with one or more groups independently selected from OH, halo and $NR_sR_t$; wherein $R_s$ and $R_t$ are each independently H or ($C_1$-$C_6$)alkyl.

In one specific embodiment of the invention u is —C(=O)NH($CR_oR_p$)$_2$— and v is —C(=O)NHCR$_o$R$_p$—; wherein each $R_o$ and $R_p$ are independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ or $R_p$ is optionally substituted with one or more groups independently selected from OH, halo and $NR_sR_t$; wherein $R_s$ and $R_t$ are each independently H or ($C_1$-$C_6$)alkyl.

In one specific embodiment of the invention both u and v are —C(=O)NH($CR_oR_p$)$_2$—; wherein each $R_o$ and $R_p$ are independently selected from H, ($C_1$-$C_6$)alkyl, aryl and aryl($C_1$-$C_6$)alkyl; and wherein any ($C_1$-$C_6$)alkyl, aryl or aryl($C_1$-$C_6$)alkyl of $R_o$ or $R_p$ is optionally substituted with one or more groups independently selected from OH, halo and $NR_sR_t$; wherein $R_s$ and $R_t$ are each independently H or ($C_1$-$C_6$)alkyl.

In one specific embodiment of the invention each $R^1$ is independently H or ($C_1$-$C_6$)alkyl wherein any ($C_1$-$C_6$)alkyl of $R^1$ is optionally substituted with one or more groups independently selected from —$NR_{a1}R_{b1}$ and —$NR_{a1}$C(=O)—$R_{c1}$.

In one specific embodiment of the invention one or two $R^1$ groups are independently ($C_1$-$C_6$)alkyl wherein any ($C_1$-$C_6$)alkyl of $R^1$ is optionally substituted with one or more groups independently selected from —$NR_{a1}R_{b1}$ and —$NR_{a1}$C(=O)—$R_{c1}$; and the remaining $R^1$ groups are H.

In one specific embodiment of the invention each $R^1$ is independently H, —(CH$_2$)$_2$NHC(=O)OC(CH$_3$)$_3$ or —(CH$_2$)$_2$NH$_2$.

In one specific embodiment of the invention one or two $R^1$ groups are selected from —(CH$_2$)$_2$NHC(=O)OC(CH$_3$)$_3$ and —(CH$_2$)$_2$NH$_2$; and the remaining $R^1$ groups are H.

In one specific embodiment of the invention each $R^1$ is independently H, —(CH$_2$)$_2$NHC(=O)OC(CH$_3$)$_3$, —(CH$_2$)$_2$NH$_2$, —(CH$_2$)$_2$NHCH$_3$, —(CH$_2$)$_2$N(CH$_3$)$_2$, —CH$_2$CH(CH$_3$)NHC(=O)OC(CH$_3$)$_3$, CH$_2$CH(CH$_3$)NH$_2$, —(CH$_2$CH(CH$_3$)NHCH$_3$, —CH$_2$CH(CH$_3$)N(CH$_3$)$_2$, —CH$_2$C(CH$_3$)$_2$NHC(=O)OC(CH$_3$)$_3$, CH$_2$C(CH$_3$)$_2$NH$_2$, —CH$_2$C(CH$_3$)$_2$NHCH$_3$ and —CH$_2$C(CH$_3$)$_2$N(CH$_3$)$_2$.

In one specific embodiment of the invention one or two $R^1$ groups are selected from —(CH$_2$)$_2$NHC(=O)OC(CH$_3$)$_3$, —(CH$_2$)$_2$NH$_2$, —(CH$_2$)$_2$NHCH$_3$, —(CH$_2$)$_2$N(CH$_3$)$_2$, —CH$_2$CH(CH$_3$)NHC(=O)OC(CH$_3$)$_3$, CH$_2$CH(CH$_3$)NH$_2$, —(CH$_2$CH(CH$_3$)NHCH$_3$, —CH$_2$CH(CH$_3$)N(CH$_3$)$_2$, —CH$_2$C(CH$_3$)$_2$NHC(=O)OC(CH$_3$)$_3$, CH$_2$C(CH$_3$)$_2$NH$_2$, —CH$_2$C(CH$_3$)$_2$NHCH$_3$ and —CH$_2$C(CH$_3$)$_2$N(CH$_3$)$_2$; and the remaining $R^1$ groups are H.

In one specific embodiment of the invention each $R^1$ is H.

In one specific embodiment of the invention d comprises an aryl-diyl ring or a heteroaryl-diyl ring that is optionally substituted with one or more groups independently selected from ($C_1$-$C_6$)alkyl, ($C_2$-$C_6$)alkenyl, ($C_2$-$C_6$)alkynyl, hydroxy, halo, cyano, nitro, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_dR_e$, —C(=O)NR$_d$R$_e$, or —NR$_d$C(=O)—R$_f$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl is optionally substituted with one or more (e.g. 1, 2, 3, or 4) groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_dR_e$, —C(=O)NR$_d$R$_e$, and —NR$_d$C(=O)—R$_f$;

each $R_d$ and $R_e$ is independently H, ($C_1$-$C_6$)alkyl, ($C_1$-$C_6$)alkanoyl, or aryl($C_1$-$C_6$)alkyl; or $R_d$ and $R_e$ together with the nitrogen to which they are attached form an N-linked heterocycle ring that is optionally substituted with one or more oxo; and each $R_f$ is ($C_1$-$C_3$)alkyl.

In one specific embodiment of the invention d comprises a phenyl-diyl ring that is optionally substituted with one or more groups independently selected from ($C_1$-$C_6$)alkyl, ($C_2$-$C_6$)alkenyl, ($C_2$-$C_6$)alkynyl, hydroxy, halo, cyano, nitro, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_dR_e$, —C(=O)NR$_d$R$_e$, or —NR$_d$C(=O)—R$_f$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl is optionally substituted with one or more (e.g. 1, 2, 3, or 4) groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_dR_e$, —C(=O)NR$_d$R$_e$, and —NR$_d$C(=O)—R$_f$; wherein each $R_d$ and $R_e$ is independently H, ($C_1$-$C_6$)alkyl, ($C_1$-$C_6$)alkanoyl, or aryl($C_1$-$C_6$)alkyl; or $R_d$ and $R_e$ together with the nitrogen to which they are attached form an N-linked heterocycle that is optionally substituted with one or more oxo; and each $R_f$ is ($C_1$-$C_3$)alkyl.

In one specific embodiment of the invention d comprises a phenyl-1,3-diyl ring that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —$C(=O)NR_dR_e$, or —$NR_dC(=O)$—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —$C(=O)NR_dR_e$, and —$NR_dC(=O)$—$R_f$; wherein each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle that is optionally substituted with one or more oxo; and each $R_f$ is $(C_1-C_3)$alkyl.

In one specific embodiment of the invention d is a pyridin-diyl ring, a pyrimidin-diyl ring, or a pyrazin-diyl that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —$C(=O)NR_dR_e$, or —$NR_dC(=O)$—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —$C(=O)NR_dR_e$, and —$NR_dC(=O)$—$R_f$; wherein each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle that is optionally substituted with one or more oxo; and each $R_f$ is $(C_1-C_3)$alkyl.

In one specific embodiment of the invention d is a pyridin-2,6-diyl ring, a pyridin-2,4-diyl ring, or pyridin-3,5-diyl ring that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —$C(=O)NR_dR_e$, or —$NR_dC(=O)$—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —$C(=O)NR_dR_e$, and —$NR_dC(=O)$—$R_f$; wherein each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle that is optionally substituted with one or more oxo; and each $R_f$ is $(C_1-C_3)$alkyl.

In one specific embodiment of the invention d comprises an aryl-diyl or heteroaryl-diyl ring that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —$C(=O)NR_dR_e$, or —$NR_dC(=O)$—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —$C(=O)NR_dR_e$, and —$NR_dC(=O)$—$R_f$;

each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle ring that is optionally substituted with one or more oxo; and each $R_f$ is $(C_1-C_3)$haloalkyl, $(C_1-C_6)$alkoxy or aryl$(C_1-C_6)$alkoxy.

In one specific embodiment of the invention d comprises a phenyl-diyl ring that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —$C(=O)NR_dR_e$, or —$NR_dC(=O)$—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —$C(=O)NR_dR_e$, and —$NR_dC(=O)$—$R_f$; wherein each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle ring that is optionally substituted with one or more oxo; and each $R_f$ is $(C_1-C_3)$haloalkyl, $(C_1-C_6)$alkoxy or aryl$(C_1-C_6)$alkoxy.

In one specific embodiment of the invention d comprises a phenyl-1,3-diyl ring that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —$C(=O)NR_dR_e$, or —$NR_dC(=O)$—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —$C(=O)NR_dR_e$, and —$NR_dC(=O)$—$R_f$; wherein each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle ring that is optionally substituted with one or more oxo; and each $R_f$ is $(C_1-C_3)$haloalkyl, $(C_1-C_6)$alkoxy or aryl$(C_1-C_6)$alkoxy.

In one specific embodiment of the invention d is a pyridin-diyl ring, a pyrimidin-diyl ring, or a pyrazin-diyl that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —$C(=O)NR_dR_e$, or —$NR_dC(=O)$—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —$C(=O)NR_dR_e$, and —$NR_dC(=O)$—$R_f$; wherein each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle that is optionally substituted with one or more oxo; and each $R_f$ is $(C_1-C_3)$haloalkyl, $(C_1-C_6)$alkoxy or aryl$(C_1-C_6)$alkoxy.

In one specific embodiment of the invention d is a pyridin-2,6-diyl ring, a pyridin-2,4-diyl ring, or pyridin-3,5-diyl ring that is optionally substituted with one or more groups independently selected from $(C_1-C_6)$alkyl, $(C_2-C_6)$alkenyl, $(C_2-C_6)$alkynyl, hydroxy, halo, cyano, nitro, $(C_1-C_6)$alkoxy, $(C_1-C_6)$alkanoyl, $(C_1-C_6)$alkanoyloxy, $(C_1-C_6)$alkoxycarbonyl, —$NR_dR_e$, —C(=O)$NR_dR_e$, or —$NR_dC$(=O)—$R_f$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_dR_e$, —C(=O)$NR_dR_e$, and —$NR_dC$(=O)—$R_f$; wherein each $R_d$ and $R_e$ is independently H, $(C_1-C_6)$alkyl, $(C_1-C_6)$alkanoyl, or aryl$(C_1-C_6)$alkyl; or $R_d$ and $R_e$ together with the nitrogen to which they are attached form an N-linked heterocycle that is optionally substituted with one or more oxo; and each $R_f$ is $(C_1-C_3)$haloalkyl, $(C_1-C_6)$alkoxy or aryl$(C_1-C_6)$alkoxy.

In one specific embodiment of the invention d comprises an aryl-diyl or heteroaryl-diyl ring that is optionally substituted with $(C_1-C_6)$alkyl, which $(C_1-C_6)$alkyl is substituted with —$NR_dR_e$; wherein each $R_d$ and $R_e$ is independently H or $(C_1-C_6)$alkyl.

In one specific embodiment of the invention d is a phenyl-diyl ring that is optionally substituted with $(C_1-C_6)$alkyl, which $(C_1-C_6)$alkyl is substituted with —$NR_dR_e$; wherein each $R_d$ and $R_e$ is independently H or $(C_1-C_6)$alkyl.

In one specific embodiment of the invention d is a phenyl-1,3-diyl ring that is optionally substituted with $(C_1-C_6)$alkyl, which $(C_1-C_6)$alkyl is substituted with —$NR_dR_e$; wherein each $R_d$ and $R_e$ is independently H or $(C_1-C_6)$alkyl.

In one specific embodiment of the invention d is a pyridin-diyl ring, a pyrimidin-diyl ring, or a pyrazin-diyl that is optionally substituted with $(C_1-C_6)$alkyl, which $(C_1-C_6)$alkyl is substituted with —$NR_dR_e$; wherein each $R_d$ and $R_e$ is independently H or $(C_1-C_6)$alkyl.

In one specific embodiment of the invention d is a pyridin-2,6-diyl ring, a pyridin-2,4-diyl ring, or pyridin-3,5-diyl ring that is optionally substituted with $(C_1-C_6)$alkyl, which $(C_1-C_6)$alkyl is substituted with —$NR_dR_e$; wherein each $R_d$ and $R_e$ is independently H or $(C_1-C_6)$alkyl.

In one specific embodiment of the invention d is a aryl-diyl or heteroaryl-diyl ring that is substituted with a $(C_1-C_6)$alkyl that is substituted with one or two hydroxy groups.

In one specific embodiment of the invention d is a heteroaryl-diyl ring that is substituted with a $(C_1-C_6)$alkyl that is substituted with one hydroxy group.

In one specific embodiment of the invention d is a aryl-diyl or heteroaryl-diyl ring that is substituted with a $(C_1-C_6)$alkyl that is substituted with one or two groups independently selected from hydroxy, amino, piperazinyl, pyrrolidinyl, piperidinyl, morpholinyl, thiomorpholinyl, tetrahydropyranyl, tetrahydropyranyl, and 1,4-dioxanyl.

In one specific embodiment of the invention d is a aryl-diyl or heteroaryl-diyl ring that is substituted with a 3-hydroxypropyl or a 2-hydroxypropyl group.

In one specific embodiment of the invention the compound of formula I is a compound of formula Ia:

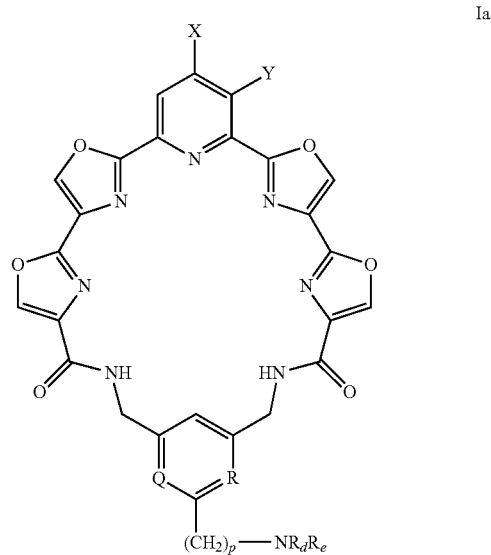

Ia wherein:

X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —$NR_aR_b$, —C(=O)$NR_aR_b$, or —$NR_aC$(=O)—$R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_aR_b$, —C(=O)$NR_aR_b$, and —$NR_aC$(=O)—$R_c$;

Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —$NR_aR_b$, —C(=O)$NR_aR_b$, or —$NR_aC$(=O)—$R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_aR_b$, —C(=O)$NR_aR_b$, and —$NR_aC$(=O)—$R_c$;

Q is CH or N;

R is CH or N;

p is 0, 1, 2, 3, or 4;

each $R_a$ and $R_b$ is independently H, $(C_1-C_6)$alkyl, $(C_1-C_6)$alkanoyl, or aryl$(C_1-C_6)$alkyl; or $R_a$ and $R_b$ together with the nitrogen to which they are attached form an N-linked heterocycle that is optionally substituted with one or more oxo;

each $R_c$ is $(C_1-C_3)$haloalkyl; and each $R_d$ and $R_e$ is independently H or $(C_1-C_6)$alkyl;

or a salt thereof.

In one specific embodiment of the invention the compound of formula I is a compound of formula Ib:

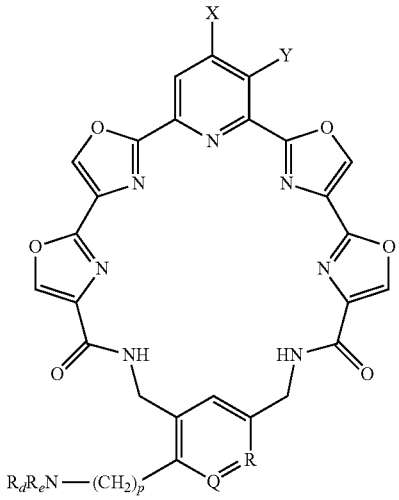

Ib wherein:

X is H, hydroxy, halo, cyano, nitro, (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, (C$_1$-C$_6$)alkoxycarbonyl, —NR$_a$R$_b$, —C(=O)NR$_a$R$_b$, or —NR$_a$C(=O)—R$_c$; wherein each (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, and (C$_1$-C$_6$)alkoxycarbonyl of X is optionally substituted with one or more (e.g. 1, 2, 3, or 4) groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_a$R$_b$, —C(=O)NR$_a$R$_b$, and —NR$_a$C(=O)—R$_c$;

Y is H, hydroxy, halo, cyano, nitro, (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, (C$_1$-C$_6$)alkoxycarbonyl, —NR$_a$R$_b$, —C(=O)NR$_a$R$_b$, or —NR$_a$C(=O)—R$_c$; wherein each (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, and (C$_1$-C$_6$)alkoxycarbonyl of Y is optionally substituted with one or more (e.g. 1, 2, 3, or 4) groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_a$R$_b$, —C(=O)NR$_a$R$_b$, and —NR$_a$C(=O)—R$_c$;

Q is CH or N;
R is CH or N;
p is 0, 1, 2, 3, or 4;
each R$_a$ and R$_b$ is independently H, (C$_1$-C$_6$)alkyl, (C$_1$-C$_6$)alkanoyl, or aryl(C$_1$-C$_6$)alkyl; or R$_a$ and R$_b$ together with the nitrogen to which they are attached form an N-linked heterocycle that is optionally substituted with one or more oxo;
each R$_c$ is (C$_1$-C$_3$)haloalkyl; and
each R$_d$ and R$_e$ is independently H or (C$_1$-C$_6$)alkyl;
or a salt thereof.

In one specific embodiment of the invention the compound of formula I is a compound of formula Ic:

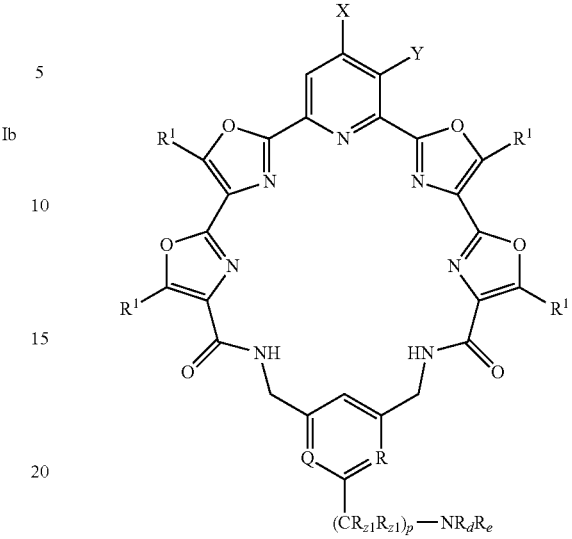

Ic wherein:

X is H, hydroxy, halo, cyano, nitro, (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, (C$_1$-C$_6$)alkoxycarbonyl, —NR$_a$R$_b$, —C(=O)NR$_a$R$_b$, or —NR$_a$C(=O)—R$_c$; wherein each (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, and (C$_1$-C$_6$)alkoxycarbonyl of X is optionally substituted with one or more (e.g. 1, 2, 3, or 4) groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_a$R$_b$, —C(=O)NR$_a$R$_b$, and —NR$_a$C(=O)—R$_c$;

Y is H, hydroxy, halo, cyano, nitro, (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, (C$_1$-C$_6$)alkoxycarbonyl, —NR$_a$R$_b$, —C(=O)NR$_a$R$_b$, or —NR$_a$C(=O)—R$_c$; wherein each (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, and (C$_1$-C$_6$)alkoxycarbonyl of Y is optionally substituted with one or more (e.g. 1, 2, 3, or 4) groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_a$R$_b$, —C(=O)NR$_a$R$_b$, and —NR$_a$C(=O)—R$_c$;

Q is CH or N;
R is CH or N;
p is 0, 1, 2, 3, or 4;
each R$^1$ is independently H or (C$_1$-C$_6$)alkyl wherein any (C$_1$-C$_6$)alkyl of R$^1$ is optionally is optionally substituted with one or more (e.g. 1, 2, 3, or 4) groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_{a1}$R$_{b1}$, —C(=O)NR$_{a1}$R$_{b1}$, and —NR$_{a1}$C(=O)—R$_{c1}$;
each R$_a$ and R$_b$ is independently H, (C$_1$-C$_6$)alkyl, (C$_1$-C$_6$)alkanoyl, or aryl(C$_1$-C$_6$)alkyl; or R$_a$ and R$_b$ together with the nitrogen to which they are attached form an N-linked heterocycle that is optionally substituted with one or more oxo;
each R$_c$ is (C$_1$-C$_3$)haloalkyl;
each R$_d$ and R$_e$ is independently H or (C$_1$-C$_6$)alkyl;
each R$_{a1}$ and R$_{b1}$ is independently H, (C$_1$-C$_6$)alkyl, (C$_1$-C$_6$)alkanoyl, or aryl(C$_1$-C$_6$)alkyl; or R$_{a1}$ and R$_{b1}$ together with the nitrogen to which they are attached form an N-linked heterocycle that is optionally substituted with one or more oxo;

each $R_{c1}$ is halo($C_1$-$C_6$)alkyl, ($C_1$-$C_6$)alkoxy or aryl($C_1$-$C_6$)alkoxy; and each $R_{z1}$ is independently H or ($C_1$-$C_3$)alkyl or a salt thereof.

In one specific embodiment of the invention the compound of formula I is a compound of formula Id:

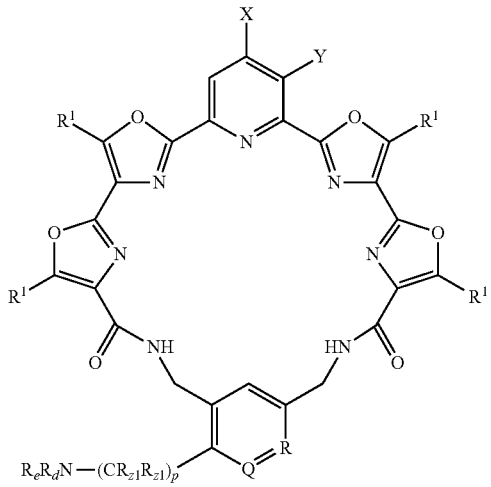

Id wherein:

X is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_aR_b$; —C(=O)$NR_a,R_b$, or —$NR_aC$(=O)—$R_c$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl of X is optionally substituted with one or more (e.g. 1, 2, 3, or 4) groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_aR_b$, —C(=O)$NR_a,R_b$, and —$NR_aC$(=O)—$R_c$;

Y is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_aR_b$; —C(=O)$NR_a,R_b$, or —$NR_aC$(=O)—$R_c$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl of Y is optionally substituted with one or more (e.g. 1, 2, 3, or 4) groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_aR_b$, —C(=O)$NR_a,R_b$, and —$NR_aC$(=O)—$R_c$;

Q is CH or N;

R is CH or N;

p is 0, 1, 2, 3, or 4;

each $R^1$ is independently H or ($C_1$-$C_6$)alkyl wherein any ($C_1$-$C_6$)alkyl of $R^1$ is optionally is optionally substituted with one or more (e.g. 1, 2, 3, or 4) groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_{a1}R_{b1}$, —C(=O)$NR_{a1}R_{b1}$, and —$NR_{a1}C$(=O)—$R_{c1}$;

each $R_a$ and $R_b$ is independently H, ($C_1$-$C_6$)alkyl, ($C_1$-$C_6$)alkanoyl, or aryl($C_1$-$C_6$)alkyl; or $R_a$ and $R_b$ together with the nitrogen to which they are attached form an N-linked heterocycle that is optionally substituted with one or more oxo;

each $R_c$ is ($C_1$-$C_3$)haloalkyl;

each $R_d$ and $R_e$ is independently H or ($C_1$-$C_6$)alkyl;

each $R_{a1}$ and $R_{b1}$ is independently H, ($C_1$-$C_6$)alkyl, ($C_1$-$C_6$)alkanoyl, or aryl($C_1$-$C_6$)alkyl; or $R_{a1}$ and $R_{b1}$ together with the nitrogen to which they are attached form an N-linked heterocycle that is optionally substituted with one or more oxo;

each $R_{c1}$ is halo($C_1$-$C_6$)alkyl, ($C_1$-$C_6$)alkoxy or aryl($C_1$-$C_6$)alkoxy; and each $R_{z1}$ is independently H or ($C_1$-$C_3$)alkyl or a salt thereof.

In one specific embodiment of the invention the compound of formula I is a compound of formula Ia:

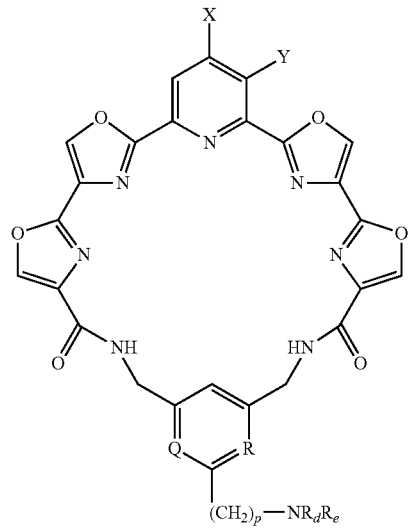

(Ia)

wherein:

X is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_aR_b$, —C(=O)$NR_a,R_b$, or —$NR_aC$(=O)—$R_c$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl of X is optionally substituted with one or more (e.g. 1, 2, 3, or 4) groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_aR_b$, —C(=O)$NR_a,R_b$, and —$NR_aC$(=O)—$R_c$;

Y is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_aR_b$, —C(=O)$NR_a,R_b$, or —$NR_aC$(=O)—$R_c$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl of Y is optionally substituted with one or more (e.g. 1, 2, 3, or 4) groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_aR_b$, —C(=O)$NR_a$—$R_b$, and —$NR_aC$(=O)—$R_c$;

Q is CH or N;

R is CH or N;

p is 0, 1, 2, 3, or 4; and each $R_d$ and $R_e$ is independently H or ($C_1$-$C_6$)alkyl;

or a salt thereof.

In one specific embodiment of the invention the compound of formula I is a compound of formula Ib:

(Ib)

wherein:
X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;

Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;

Q is CH or N;
R is CH or N;
p is 0, 1, 2, 3, or 4; and
each $R_d$ and $R_e$ is independently H or $(C_1-C_6)$alkyl;
or a salt thereof.

In one specific embodiment of the invention Q is CH
In one specific embodiment of the invention R is CH
In one specific embodiment of the invention Q is N
In one specific embodiment of the invention R is N
In one specific embodiment of the invention p is 2.
In one specific embodiment of the invention one or two $R_{z1}$ groups are $(C_1-C_3)$alkyl and the remaining $R_{z1}$ groups are H.
In one specific embodiment of the invention one or two $R_{z1}$ groups are methyl and the remaining $R_{z1}$ groups are H.
In one specific embodiment of the invention one $R_{z1}$ group is methyl and the remaining $R_{z1}$ groups are H.
In one specific embodiment of the invention each $R_{z1}$ groups is H.

In one specific embodiment of the invention d is a 1,3-phenyldiyl ring that is optionally substituted with one or more halo, hydroxyl, cyano, nitro, trifluoromethyl, trifluoromethoxy, amino, methylamino, or dimethylamino.

In one specific embodiment of the invention d is a pyridin-2,6-diyl ring, a pyridin-2,4-diyl ring, or pyridin-3,5-diyl ring that is optionally substituted with one or more halo, hydroxyl, cyano, nitro, trifluoromethyl, trifluoromethoxy, amino, methylamino, or dimethylamino.

In one specific embodiment of the invention X is H, halo, $(C_1-C_6)$alkyl or $(C_1-C_6)$alkoxy; wherein each $(C_1-C_6)$alkyl or $(C_1-C_6)$alkoxy of X is optionally substituted with one or more groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;

In one specific embodiment of the invention X is H, Cl, Br, or I.

In one specific embodiment of the invention X is H or Br.
In one specific embodiment of the invention X is H, halo or $(C_1-C_6)$alkoxy; wherein each $(C_1-C_6)$alkoxy of X is optionally substituted with one or more $-NR_aR_b$ groups.

In one specific embodiment of the invention X is H or halo.
In one specific embodiment of the invention X is selected from H, Br, In one specific embodiment of the invention Y is H.
In one specific embodiment of the invention W is O.
In one specific embodiment of the invention at least one W is O and at least one W is S.
In one specific embodiment of the invention each W is S.
In one specific embodiment of the invention Z is CH.
In one specific embodiment of the invention Z is N.
In one specific embodiment of the invention -u- comprises an organic radical that comprises a 1, 2, 3, or 4 membered chain that taken together with -d-v- comprises a 9 membered chain that taken together with the remainder of formula I forms a compound that comprises a 24 membered ring.

In one specific embodiment of the invention -d- comprises an organic radical that comprises a 1, 2, 3, or 4 membered chain that taken together with -u- and -v- comprises a 9 membered chain that taken together with the remainder of formula I forms a compound that comprises a 24 membered ring.

In one specific embodiment of the invention -v- comprises an organic radical that comprises a 1, 2, 3, or 4 membered chain that taken together with -u-d- comprises a 9 membered chain that taken together with the remainder of formula I forms a compound that comprises a 24 membered ring.

In one specific embodiment of the invention -d- comprises an organic radical that comprises a 1 membered chain; -u- comprises an organic radical that comprises a 4 membered chain; and -v- comprises an organic radical that comprises a 4 membered chain, such that when the -d- chain, the -u- chain, and the -v- chain are taken together with the remainder of formula I it forms a compound that comprises a 24 membered ring.

In one specific embodiment of the invention -d- comprises an organic radical that comprises a 3 membered chain; -u- comprises an organic radical that comprises a 3 membered chain; and -v- comprises an organic radical that comprises a 3 membered chain, such that when the -d- chain, the -u- chain, and the -v- chain are taken together with the remainder of formula I it forms a compound that comprises a 24 membered ring.

In one specific embodiment of the invention -u- comprises an organic radical that comprises a 3 membered chain; and -v- comprises an organic radical that comprises a 3 membered chain, such that when the -d- chain, the -u- chain, and the -v- chain are taken together with the remainder of formula I it forms a compound that comprises a 24 membered ring.

In one specific embodiment of the invention -u- comprises an organic radical that comprises a 3 membered chain and -v- comprises an organic radical that comprises a 4 membered chain such that when -d-, the -u- chain, and the -v- chain are taken together with the remainder of formula I it forms a compound that comprises a 24 membered ring.

In one specific embodiment of the invention -u- comprises an organic radical that -u- comprises an organic radical that comprises a 4 membered chain; and -v- comprises an organic radical that comprises a 3 membered chain; such that when -d-, the -u- chain, and the -v- chain are taken together with the remainder of formula I it forms a compound that comprises a 24 membered ring.

In one specific embodiment of the invention -u- comprises an organic radical that comprises a 4 membered chain; and -v- comprises an organic radical that comprises a 4 membered chain, such that when -d-, the -u- chain, and the -v- chain are taken together with the remainder of formula I it forms a compound that comprises a 24 membered ring.

In one specific embodiment of the invention -d- is $-NR_{20}-$, $-O-$, $-S-$, $-S(=O)-$, $-S(=O)_2-$, $-C(=O)-$, $-C(=S)-$, or $-CR_{21}R_{22}-$; $R_{20}$ is H, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $NH_2$, $NH((C_1-C_6)$alkyl or $N((C_1-C_6)$alkyl$)_2$ wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of $R_{20}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{23}R_{24}$, $-C(=O)NR_{23}R_{24}$, and $-NR_{23}C(=O)-R_{26}$;

$R_{21}$ is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_{23}R_{24}$, $-C(=O)NR_{23}R_{24}$, or $-NR_{23}C(=O)-R_{26}$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of $R_{21}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{23}R_{24}$, $-C(=O)NR_{23}R_{24}$, and $-NR_{23}C(=O)-R_{26}$;

$R_{22}$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $-C(=O)NR_{23}R_{24}$, or $-NR_{23}C(=O)-R_{26}$; wherein each $(C_1-C_6)$alkyl, $(C_2-C_6)$alkenyl, $(C_2-C_6)$alkynyl, $(C_1-C_6)$alkanoyl, and $(C_1-C_6)$alkoxycarbonyl of $R_{21}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{23}R_{24}$, $-C(=O)NR_{23}R_{24}$, and $-NR_{23}C(=O)-R_{26}$;

each $R_{23}$ and $R_{24}$ is independently H, $(C_1-C_6)$alkyl, $(C_1-C_6)$alkanoyl, or aryl$(C_1-C_6)$alkyl; or $R_{23}$ and $R_{24}$ together with the nitrogen to which they are attached form an pyrrolidino, piperidino, piperazino, morpholino, thiomorpholino, or azepino ring; and each $R_{26}$ is $(C_1-C_3)$alkyl.

In one specific embodiment of the invention -d- is $-NR_{20}-$, $-O-$, $-S-$, $-S(=O)-$, $-S(=O)_2-$, $-C(=S)-$, or $-CR_{21}R_{22}-$; $R_{20}$ is H, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, or $(C_1-C_6)$alkoxycarbonyl wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of $R_{20}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{23}R_{24}$, $-C(=O)NR_{23}R_{24}$, and $-NR_{23}C(=O)-R_{26}$;

$R_{21}$ is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_{23}R_{24}$, $-C(=O)NR_{23}R_{24}$, or $-NR_{23}C(=O)-R_{26}$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of $R_{21}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{23}R_{24}$, $-C(=O)NR_{23}R_{24}$, and $-NR_{23}C(=O)-R_{26}$; $R_{22}$ is H, $(C_1-C_6)$alkyl, $(C_2-C_6)$alkenyl, $(C_2-C_6)$alkynyl, $(C_1-C_6)$alkanoyl, $(C_1-C_6)$alkoxycarbonyl, $-C(=O)NR_{23}R_{24}$, or $-NR_{23}C(=O)-R_{26}$; wherein each $(C_1-C_6)$alkyl, $(C_2-C_6)$alkenyl, $(C_2-C_6)$alkynyl, $(C_1-C_6)$alkanoyl, and $(C_1-C_6)$alkoxycarbonyl of $R_{21}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{23}R_{24}$, $-C(=O)NR_{23}R_{24}$, and $-NR_{23}C(=O)-R_{26}$; each $R_{23}$ and $R_{24}$ is independently H, $(C_1-C_6)$alkyl, $(C_1-C_6)$alkanoyl, or aryl$(C_1-C_6)$alkyl; or $R_{23}$ and $R_{24}$ together with the nitrogen to which they are attached form an pyrrolidino, piperidino, piperazino, morpholino, thiomorpholino, or azepino ring; and each $R_{26}$ is $(C_1-C_3)$alkyl.

In one specific embodiment of the invention -d- is $-NR_{20}-$, $-O-$, $-S-$, $-S(=O)-$, $-S(=O)_2-$, $-C(=O)-$, $-C(=S)-$, or $-CR_{21}R_{22}-$; $R_{20}$ is H, or $(C_1-C_6)$alkyl, wherein each $(C_1-C_6)$alkyl of $R_{20}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, and $-NR_{23}R_{24}$; $R_{21}$ is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, or $(C_1-C_6)$alkanoyloxy; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, and $(C_1-C_6)$alkanoyloxy of $R_{21}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, and $-NR_{23}R_{24}$; and $R_{22}$ is H, $(C_1-C_6)$alkyl, $(C_2-C_6)$alkenyl, $(C_2-C_6)$alkynyl, or $(C_1-C_6)$alkanoyl; wherein each $(C_1-C_6)$alkyl, $(C_2-C_6)$alkenyl, $(C_2-C_6)$ alkynyl, and $(C_1-C_6)$alkanoyl of $R_{21}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, and $-NR_{23}R_{24}$.

In one specific embodiment of the invention -d- is $-NR_{20}-$, $-O-$, $-S-$, $-C(=O)-$, or $-CR_{21}R_{22}-$; $R_{20}$ is H, or $(C_1-C_6)$alkyl, wherein each $(C_1-C_6)$alkyl of $R_{20}$ is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, and $-NR_{23}R_{24}$; $R_{21}$ is H or $(C_1-C_3)$alkyl; and $R_{22}$ is H or $(C_1-C_3)$alkyl.

In one specific embodiment of the invention -u-d-v- is selected from:

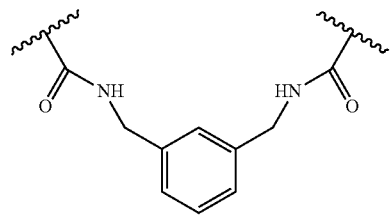

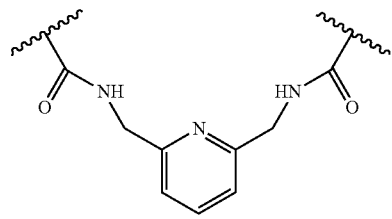

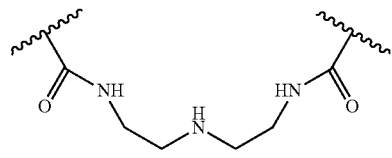

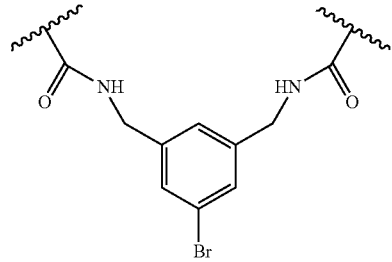

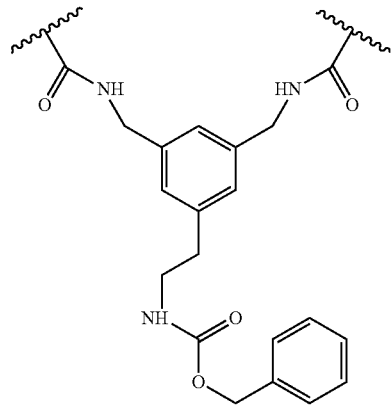

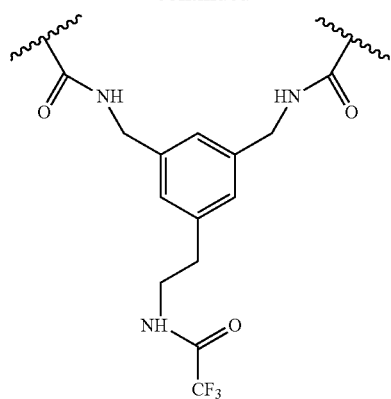

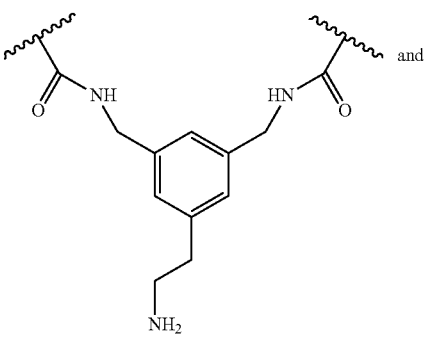

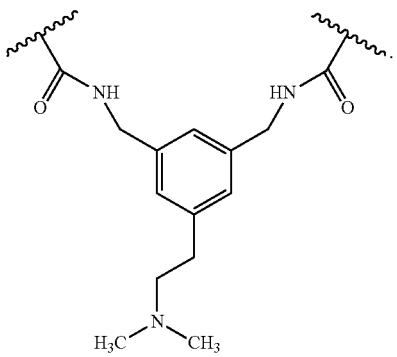

In one specific embodiment of the invention -u-d-v- is selected from:

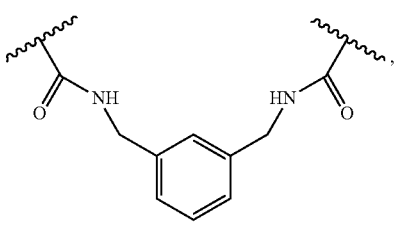

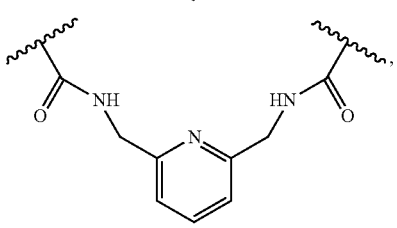

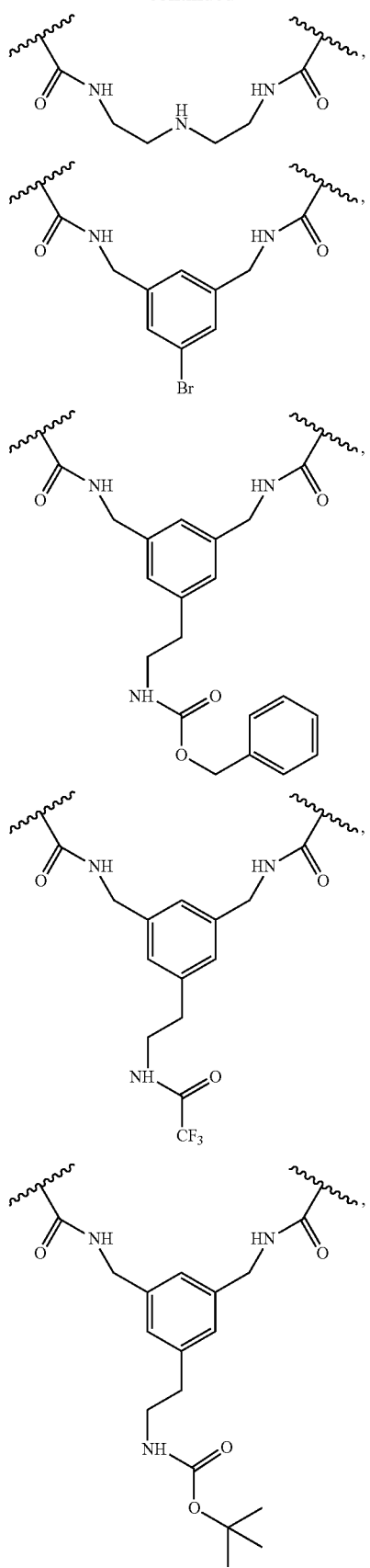
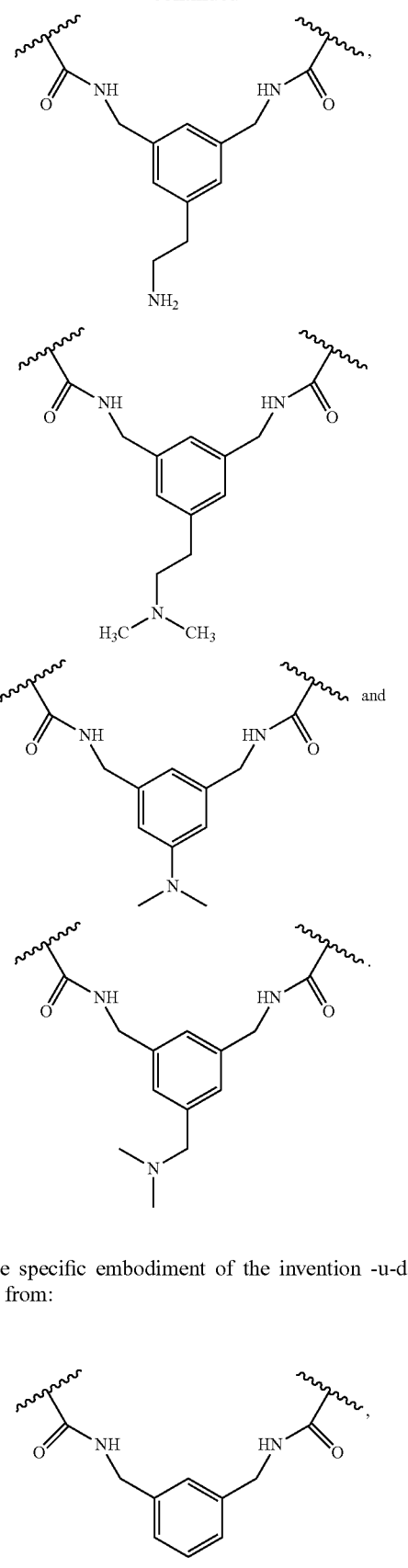
In one specific embodiment of the invention -u-d-v- is selected from:
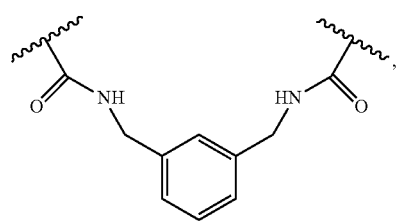

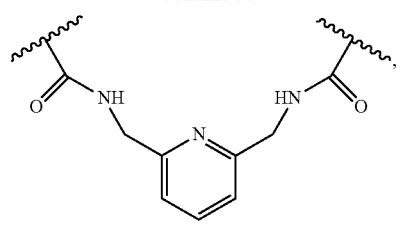
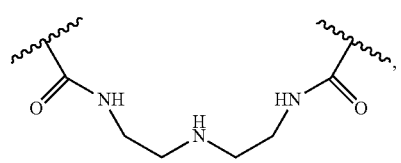
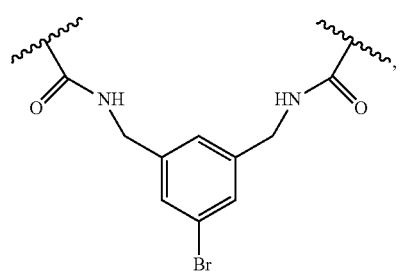
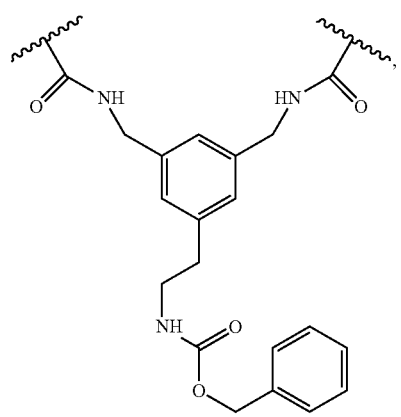
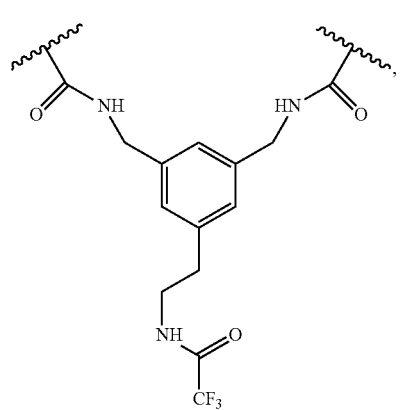
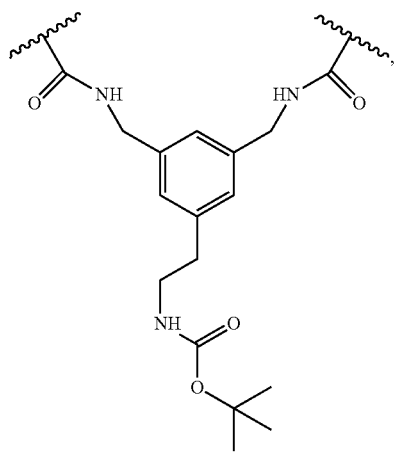
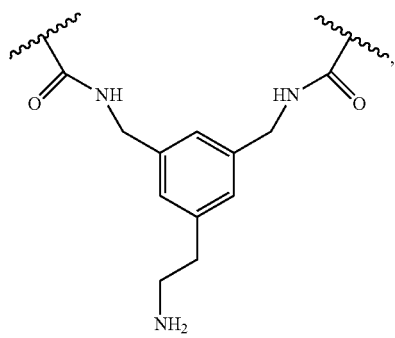
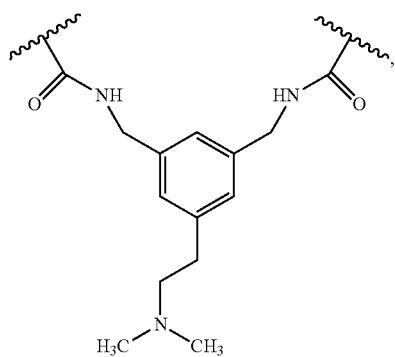
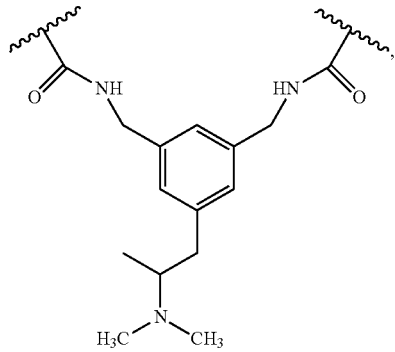

-continued
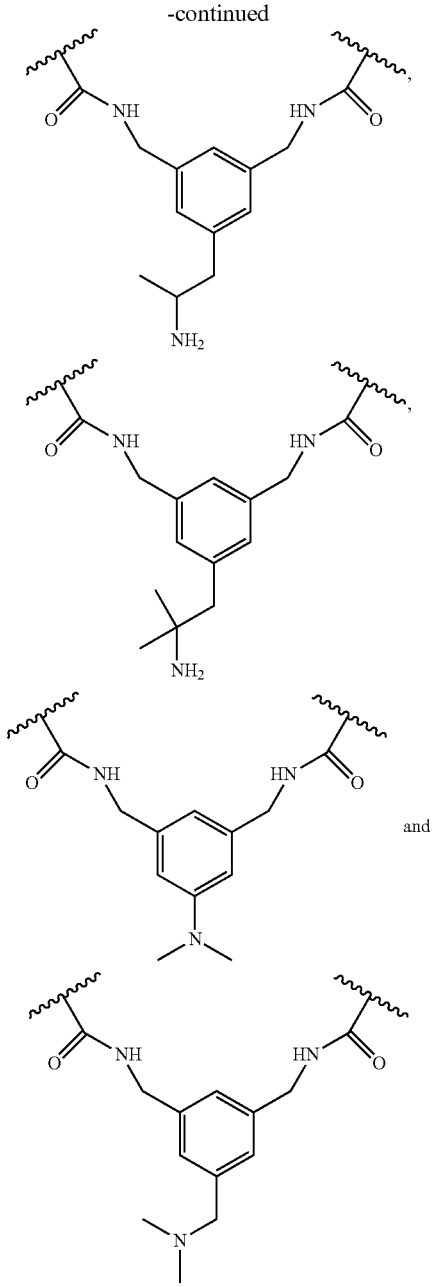
In one specific embodiment of the invention Z is N; Y is H; and X is selected from H, Br,
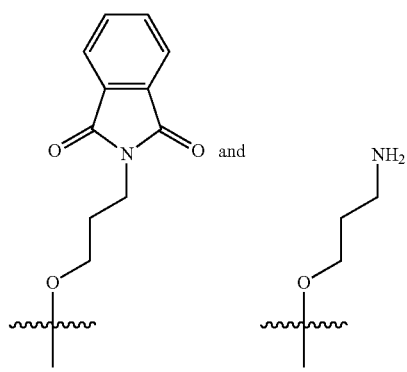 [SMILES: *OCCCN1C(=O)c2ccccc2C1=O ; "and" ; *OCCCN]
In one specific embodiment the invention provides a compound of formula I that is selected from:
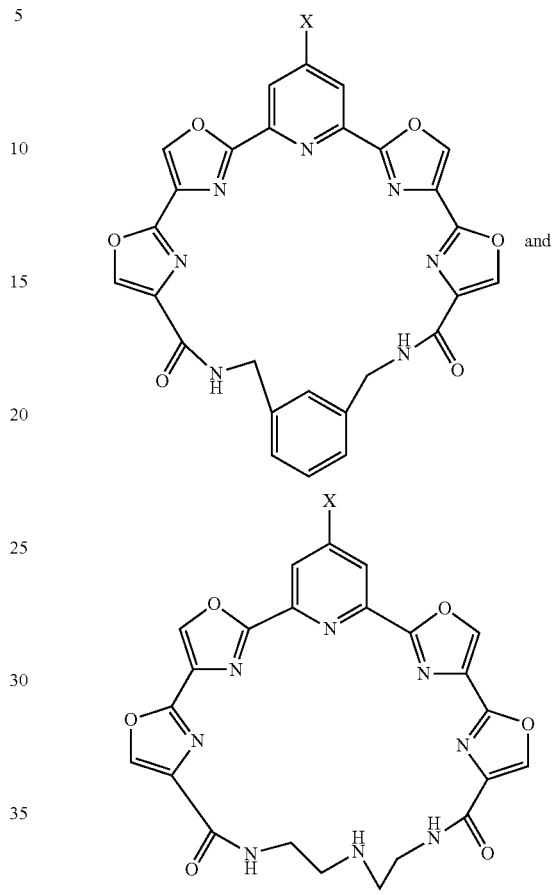
and salts thereof.
In one embodiment the invention provides a compound of formula I that is selected from:
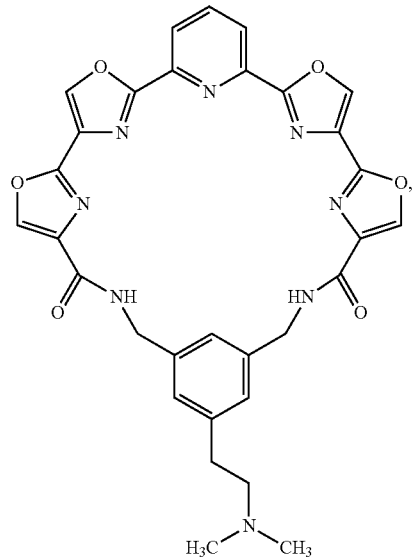

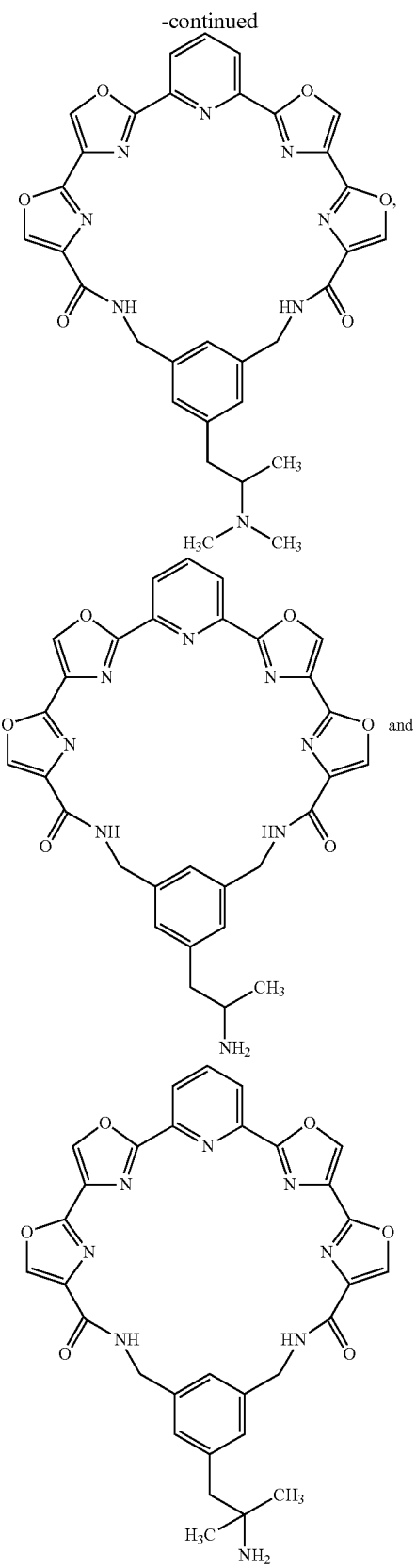

or a salt thereof.

In one embodiment of the invention the compound of formula I has a mass of less than about 895 amu.

In one specific embodiment of the invention -u-d-v- has a mass of less than about 550 amu. In another specific embodiment of the invention -u-d-v- has a mass of less than about 400 amu. In another specific embodiment of the invention -u-d-v- has a mass of less than about 300 amu.

In one specific embodiment the invention provides a compound of formula I as described in any one of the Examples herein; or a salt thereof.

In one embodiment the compound of formula I excludes a compound of formula (II):

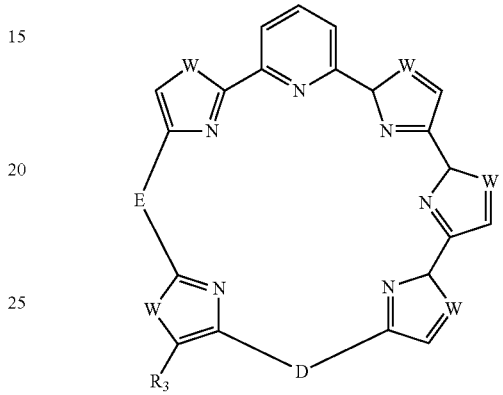

(II)

wherein:
each D and E is independently —C(=O)NH—CH($R_g$)—, —C(=O)—NH—C(=O)—, or a group of the formula:

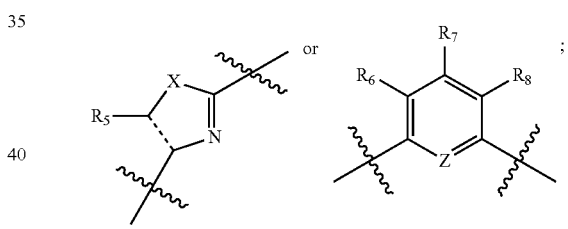

each $R_3$ and $R_5$ is independently H, ($C_1$-$C_6$)alkyl, or ($C_1$-$C_6$)alkoxy, wherein each ($C_1$-$C_6$)alkyl and ($C_1$-$C_6$)alkoxy is optionally substituted with OH, ($C_1$-$C_6$)alkoxy, ($C_1$-$C_6$)alkylthio, aryl, $NR_hR_k$, or —C(=O)$NR_hR_k$;

each $R_6$, $R_7$, and $R_8$ is independently H; or each $R_6$ and $R_7$ together with the atoms to which they are attached form a benzo ring and $R_8$ is H; or $R_6$ is H and $R_7$ and $R_8$ together with the atoms to which they are attached form a benzo ring;

each W is independently NH, S, or O;

each Z is independently N or CH;

the bond represented by ----- is a single or a double bond;

each $R_g$ is independently H, aryl, or ($C_1$-$C_6$)alkyl that is optionally substituted with OH, ($C_1$-$C_6$)alkoxy, ($C_1$-$C_6$)alkylthio, aryl, $NR_mR_n$, or —C(=O)$NR_mR_n$;

each $R_h$ and $R_k$ is independently H or ($C_1$-$C_6$)alkyl; or $R_h$ and $R_k$ together with the nitrogen to which they are attached form a pyrrolidino, piperidino, piperazino, morpholino, thiomorpholino, or azepino ring; and each $R_m$ and $R_n$ is independently H or ($C_1$-$C_6$)alkyl; or $R_m$ and $R_n$ together with the nitrogen to which they are attached form a pyrrolidino, piperidino, piperazino, morpholino, thiomorpholino, or azepino ring;

and salts thereof.

In another embodiment the compound of formula I excludes compounds wherein: u and v are each independently —C(=O)NH—CH(R$_{a1}$)—, —C(=O)—NH—C(=O)—, or a group of the formula:

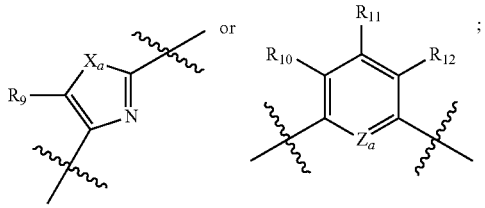

each R$_9$ is independently H, (C$_1$-C$_6$)alkyl, or (C$_1$-C$_6$)alkoxy, wherein each (C$_1$-C$_6$)alkyl and (C$_1$-C$_6$)alkoxy is optionally substituted with OH, (C$_1$-C$_6$)alkoxy, (C$_1$-C$_6$)alkylthio, aryl, NR$_{c1}$R$_{d1}$, or —C(=O)NR$_{c1}$R$_{d1}$;

each R$_{10}$, R$_{11}$, and R$_{12}$ is independently H; or each R$_{10}$ and R$_{11}$ together with the atoms to which they are attached form a benzo ring and R$_{12}$ is H; or R$_{10}$ is H and R$_{11}$ and R$_{12}$ together with the atoms to which they are attached form a benzo ring;

each X$_a$ is independently NH, S, or O;

each Z$_a$ is independently N or CH;

the bond represented by ----- is a single or a double bond;

each R$_{a1}$ is independently H, aryl, or (C$_1$-C$_6$)alkyl that is optionally substituted with OH, (C$_1$-C$_6$)alkoxy, (C$_1$-C$_6$)alkylthio, aryl, NR$_{e1}$R$_{f1}$, or —C(=O)NR$_{e1}$R$_{f1}$;

each R$_{c1}$ and R$_{d1}$ is independently H or (C$_1$-C$_6$)alkyl; or R$_{c1}$ and R$_{d1}$ together with the nitrogen to which they are attached form a pyrrolidino, piperidino, piperazino, morpholino, thiomorpholino, or azepino ring;

each R$_{e1}$ and R$_{f1}$ is independently H or (C$_1$-C$_6$)alkyl; or R$_{e1}$ and R$_{f1}$ together with the nitrogen to which they are attached form a pyrrolidino, piperidino, piperazino, morpholino, thiomorpholino, or azepino ring;

d is a ring of formula:

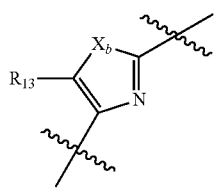

X$_b$ is independently NH, S, or O;

R$_{13}$ is H, (C$_1$-C$_6$)alkyl, or (C$_1$-C$_6$)alkoxy, wherein each (C$_1$-C$_6$)alkyl and (C$_1$-C$_6$)alkoxy is optionally substituted with OH, (C$_1$-C$_6$)alkoxy, (C$_1$-C$_6$)alkylthio, aryl, NR$_{c2}$R$_{d2}$, or —C(=O)NR$_{c2}$R$_{d2}$; and each R$_{c2}$ and R$_{d2}$ is independently H or (C$_1$-C$_6$)alkyl; or R$_{c2}$ and R$_{d2}$ together with the nitrogen to which they are attached form a pyrrolidino, piperidino, piperazino, morpholino, thiomorpholino, or azepino ring;

or a salt thereof.

In another embodiment the compound of formula I excludes compounds wherein -u-d-v- comprises an oxazol-1,5-diyl ring; and salts thereof.

In another embodiment the compound of formula I excludes compounds wherein d comprises an oxazol-1,5-diyl ring; and salts thereof.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, phosphate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), a vegetable oil, a nontoxic glyceryl ester, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Accordingly, in one embodiment the invention also provides a composition comprising a compound of formula (I), or a pharmaceutically acceptable salt thereof, at least one other therapeutic agent, and a pharmaceutically acceptable diluent or carrier. The invention also provides a kit comprising a compound of formula (I), or a pharmaceutically acceptable salt thereof, at least one other therapeutic agent, packaging material, and instructions for administering the compound of formula I or the pharmaceutically acceptable salt thereof and the other therapeutic agent or agents to an animal to treat cancer.

Compounds of the invention may be useful in limiting (e.g. inhibiting, decreasing) the synthesis of pathological proteins in a mammal (e.g., a human male or female). Such pathological proteins include proteins that are undesirable and/or proteins that are overexpressed and may lead to disease. Accordingly, in one embodiment the invention provides a method to limit the synthesis of a pathological protein in a mammal comprising administering to the mammal a compound of formula I or a pharmaceutically acceptable salt thereof. In another embodiment the invention provides a method to limit the synthesis of a pathological protein comprising contacting a G-quadruplex DNA or RNA with a compound of formula I, or a salt thereof.

The compounds of formula I can conveniently be grouped as types A, B, and C below wherein -u-d-v- taken together is an organic radical that comprises nine (9) consecutive atoms that when taken together with the remainder of Formula I can form a 24 membered ring.

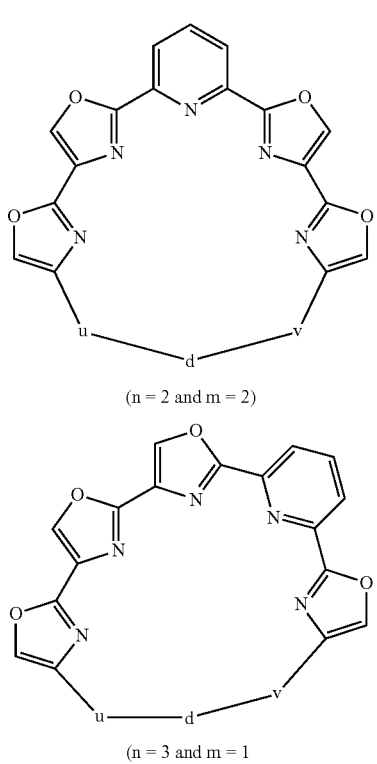

Type A (n = 2 and m = 2)

Type B (n = 3 and m = 1)

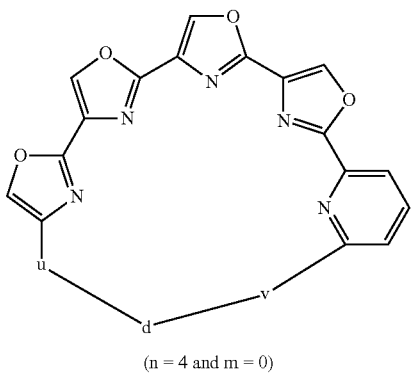

Type C (n = 4 and m = 0)

—u—d—v— comprises a 9-membered chain

The preparation of an intermediate compounds that can be used to prepare compounds of type A (or related molecules wherein n=2 and m=2) of formula I is illustrated in Schemes 1, 2 and 3. Compounds wherein the oxazoles are independently replaced with thiazole or imidazole rings can be prepared following similar procedures.

Scheme 1

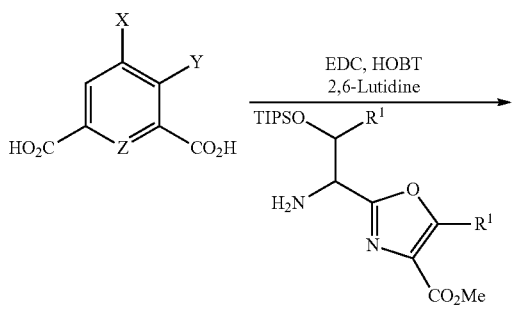

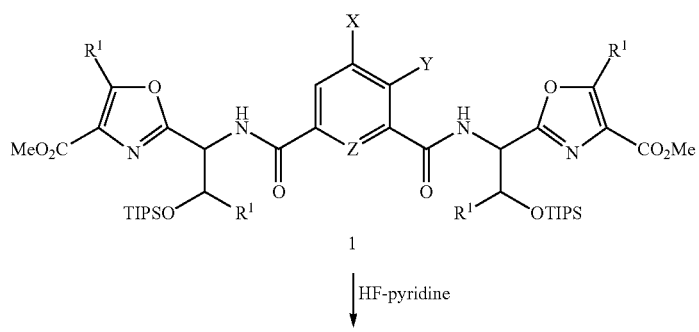

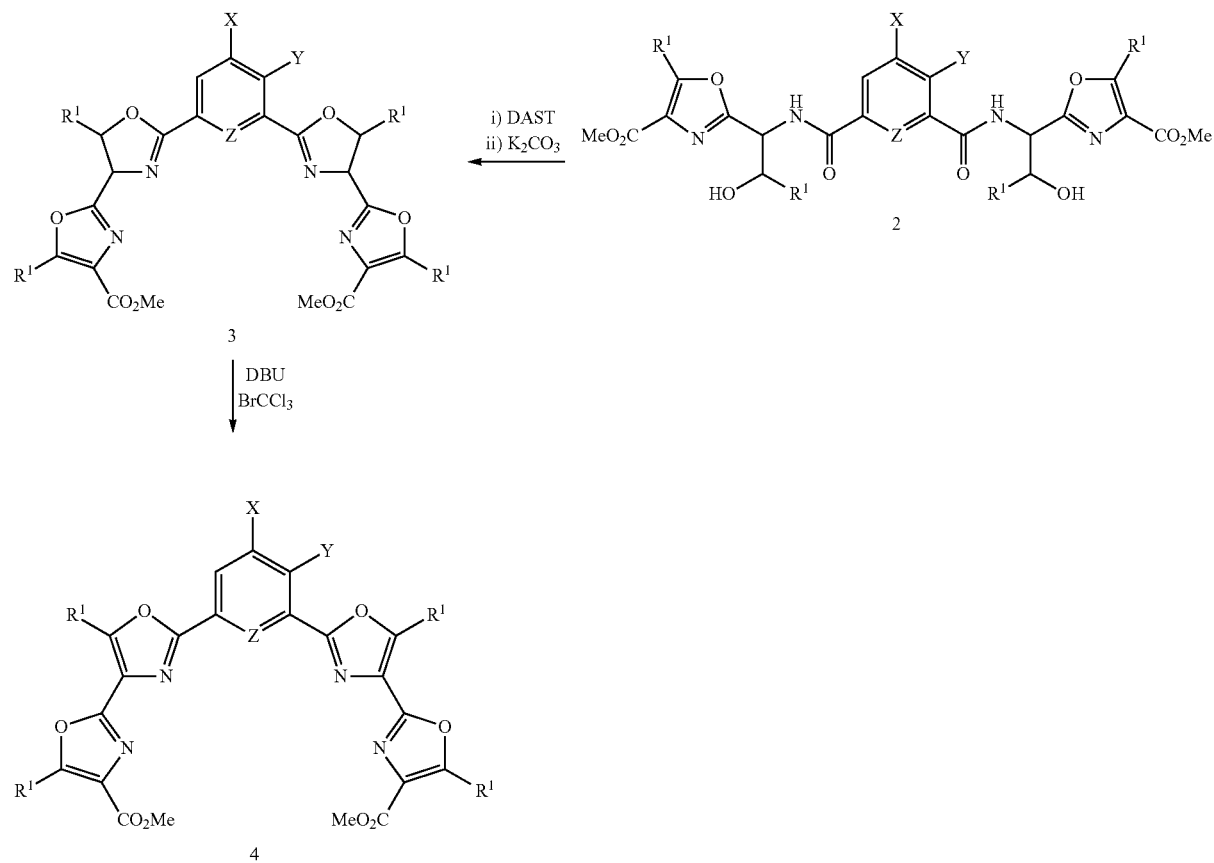
Scheme 2
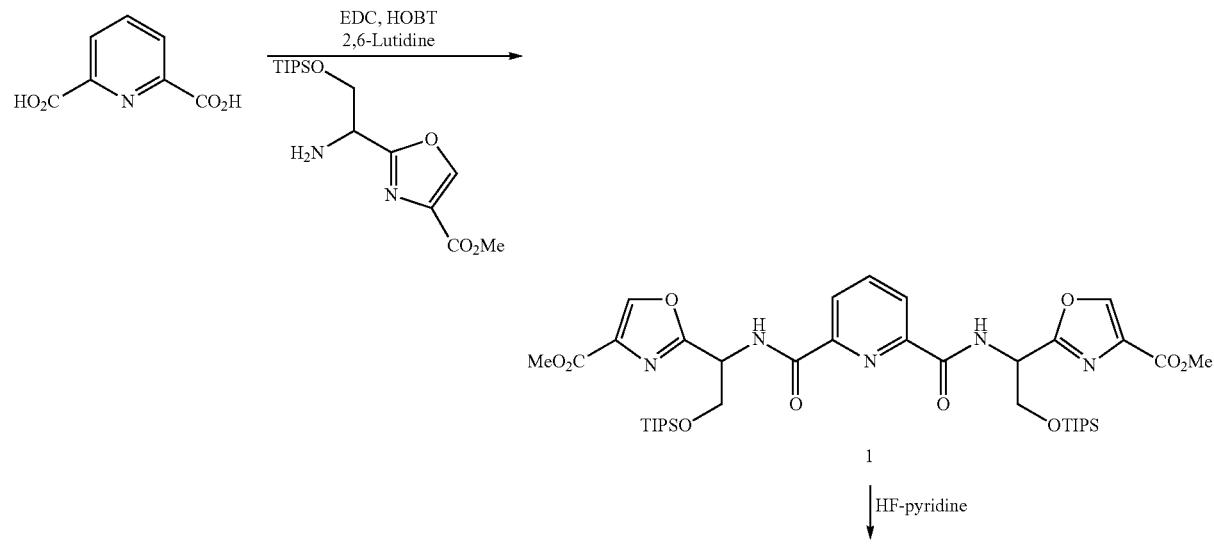

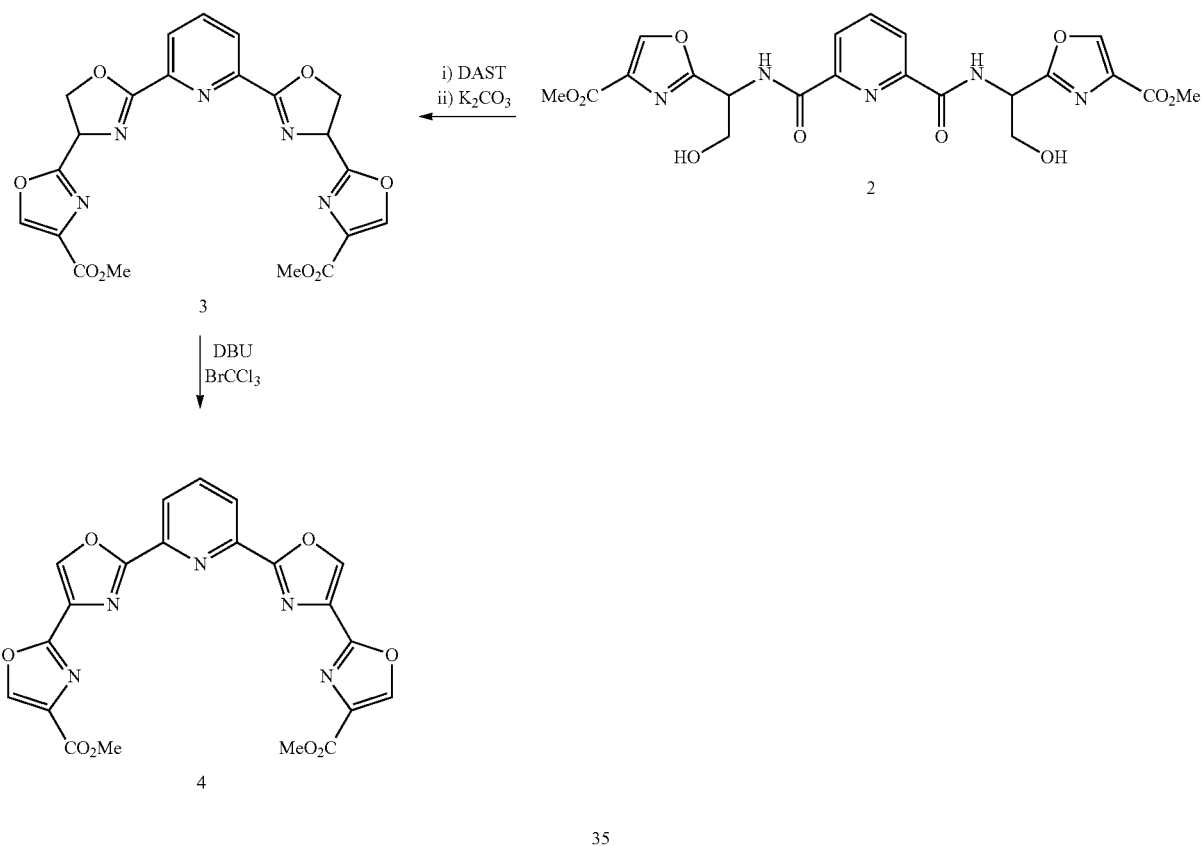
Scheme 3
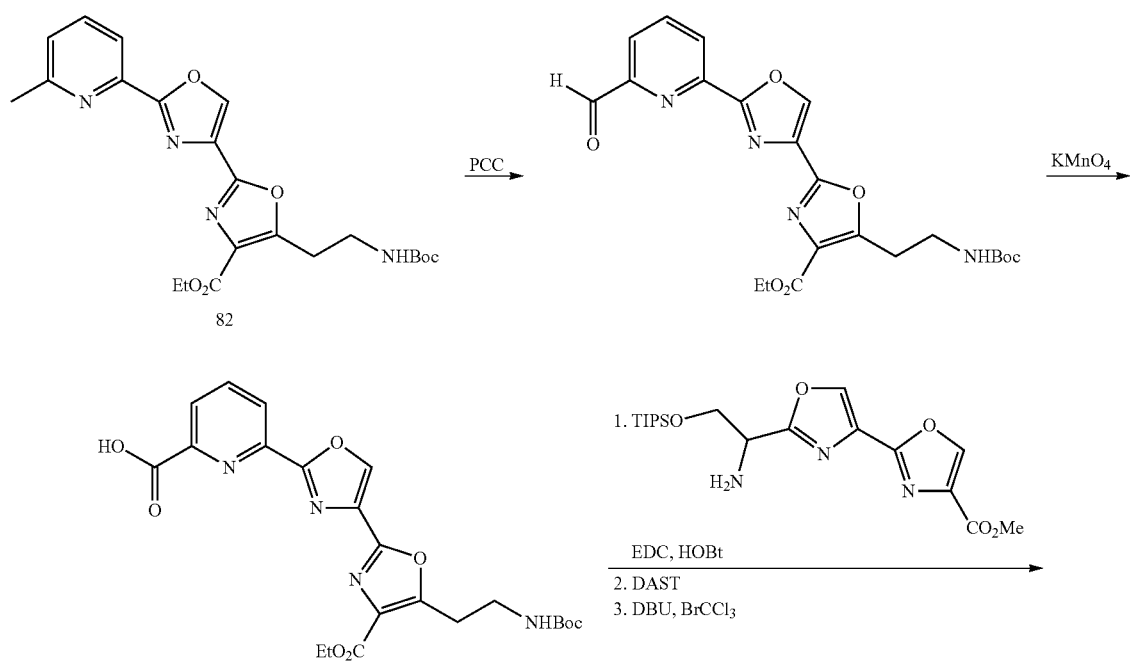

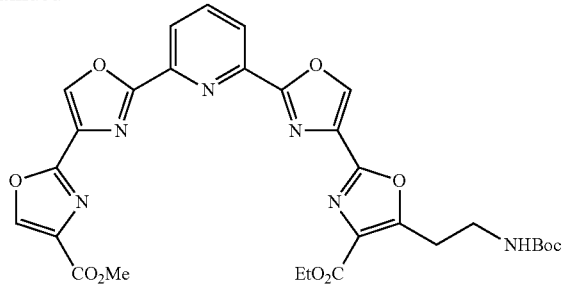
The preparation of intermediate compounds that can be used to prepare compounds of type B (or related molecules wherein n=3 and m=1) of formula I is illustrated in Schemes 4 and 5. Compounds wherein the oxazoles are independently replaced with thiazole or imidazole rings can be prepared following similar procedures.
Scheme 4
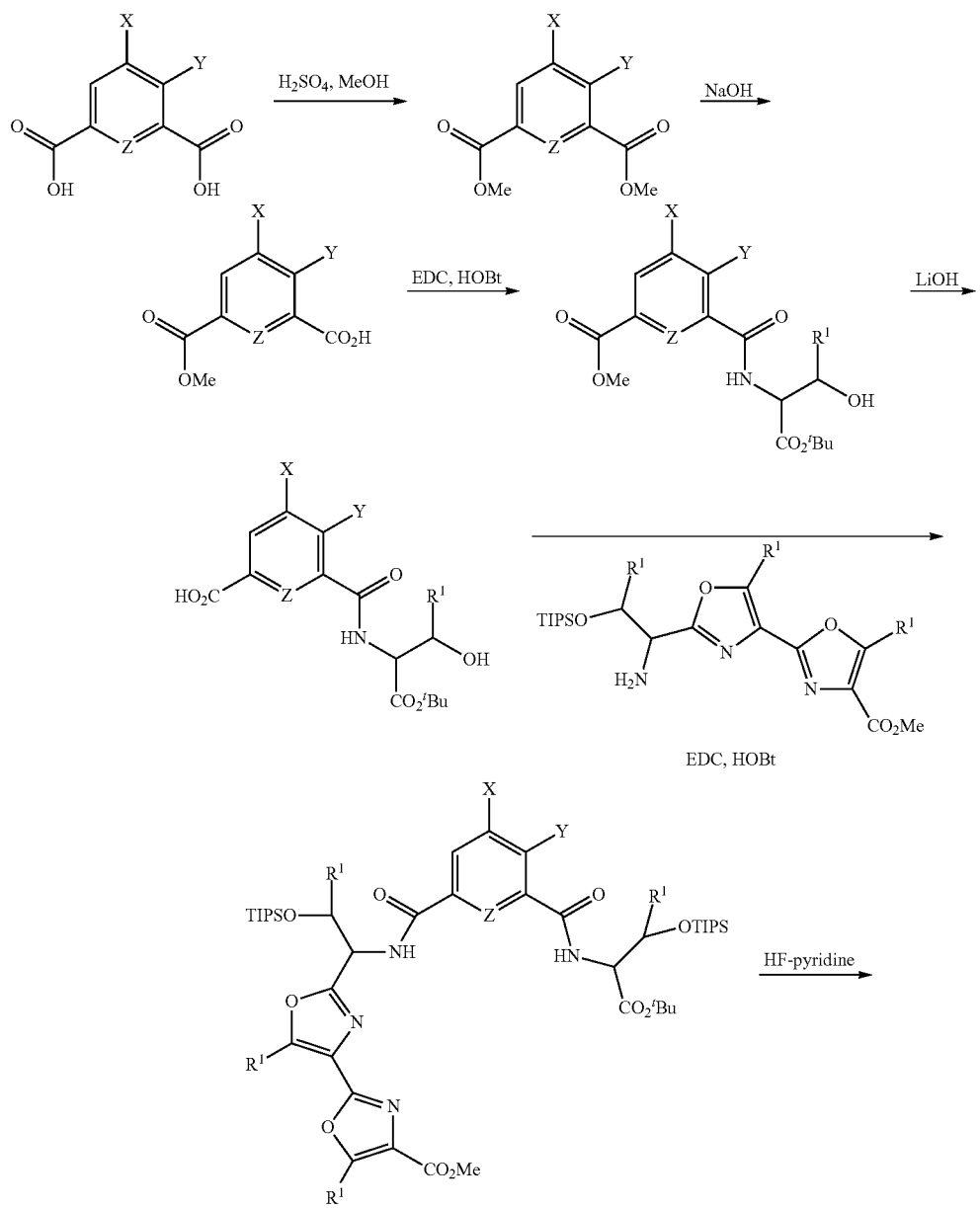

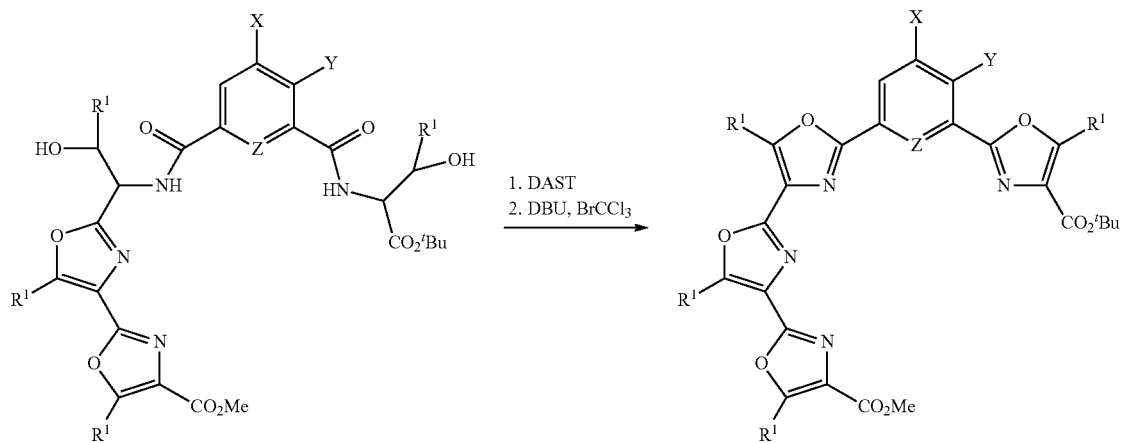
Scheme 5
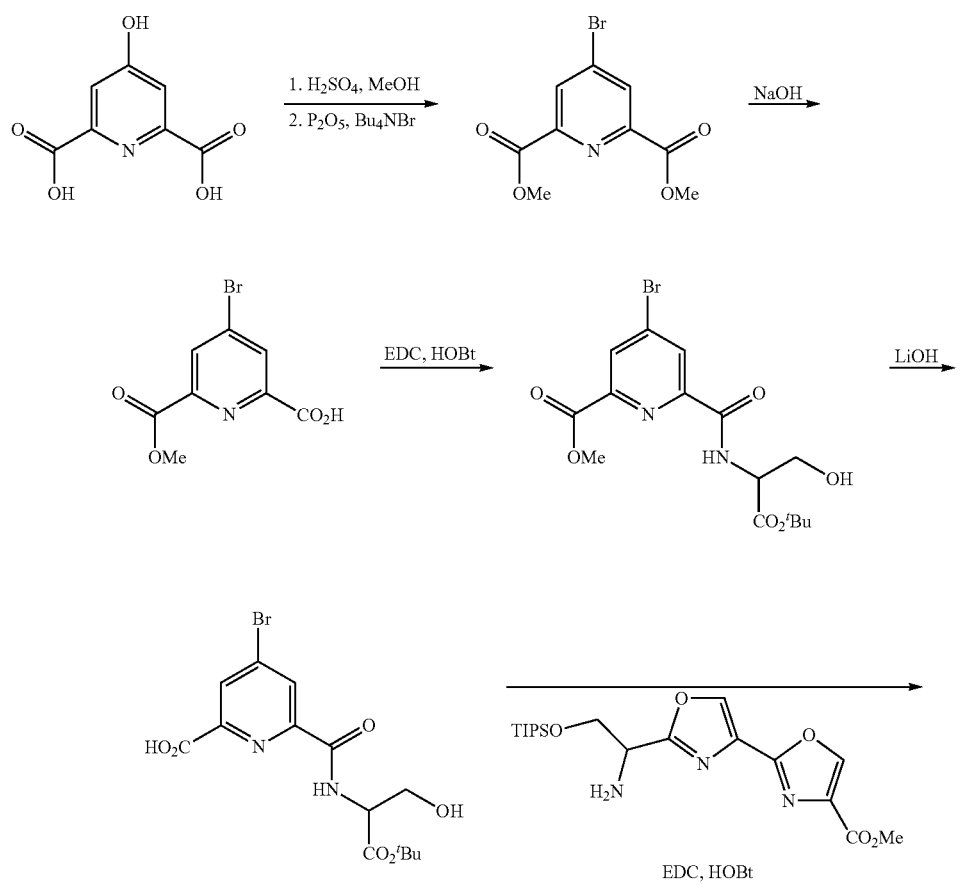

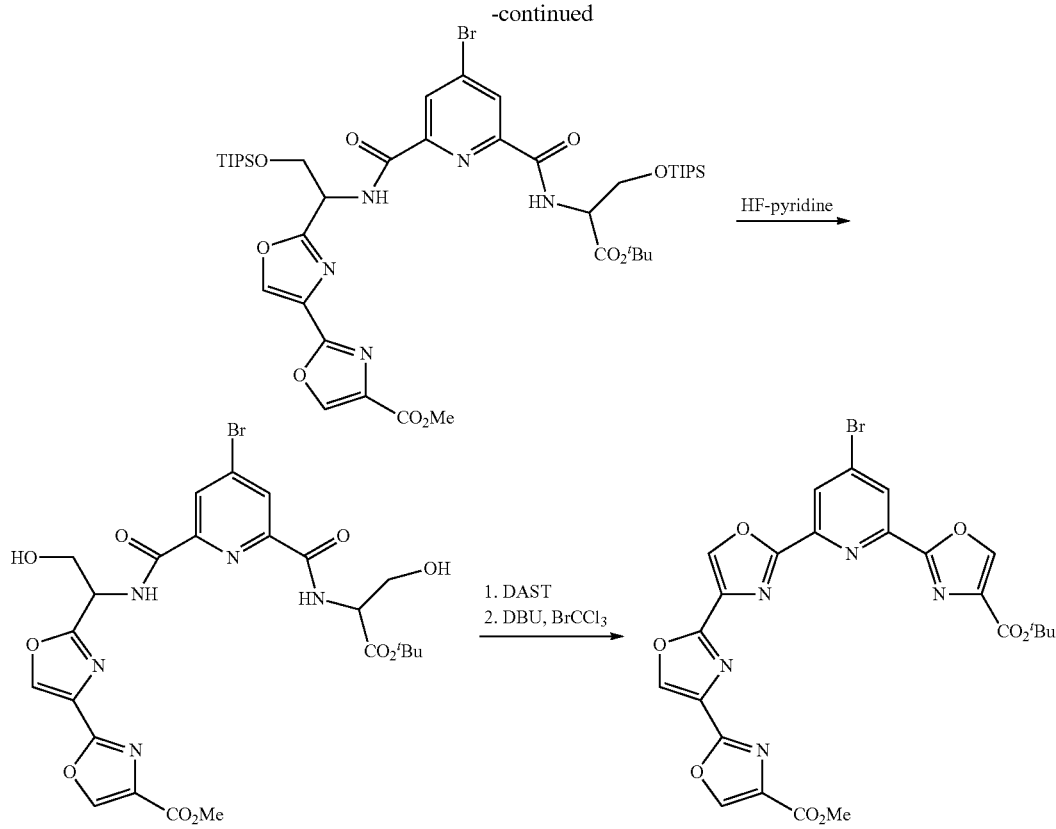
The preparation of an intermediate compound that can be used to prepare compounds of type C (or related molecules wherein n=4 and m=0) of formula I is illustrated in Schemes 6 and 7. Compounds wherein the oxazoles are independently replaced with thiazole or imidazole rings can be prepared following similar procedures.
Scheme 6
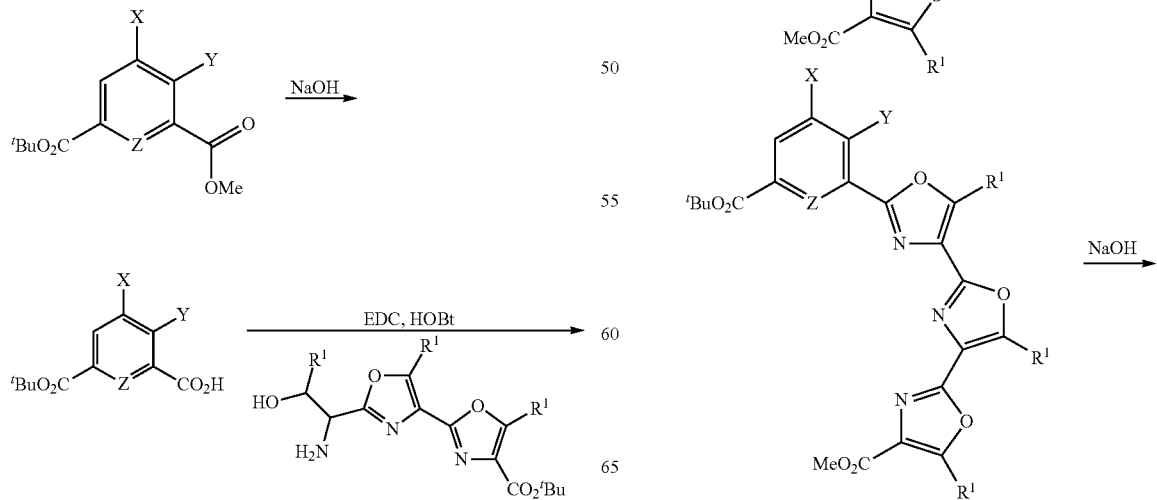
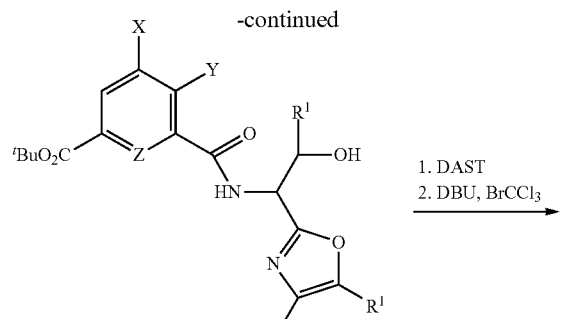

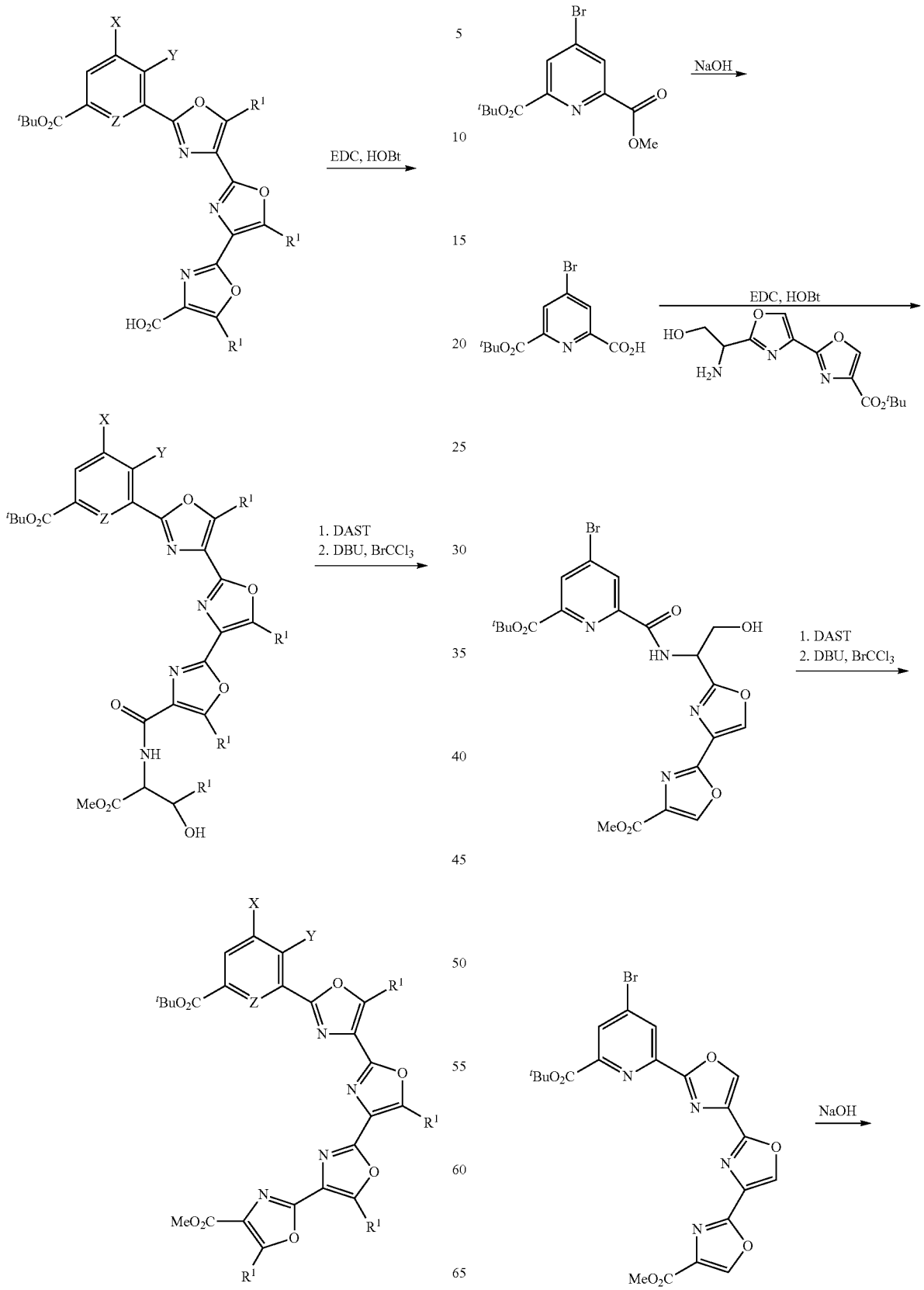

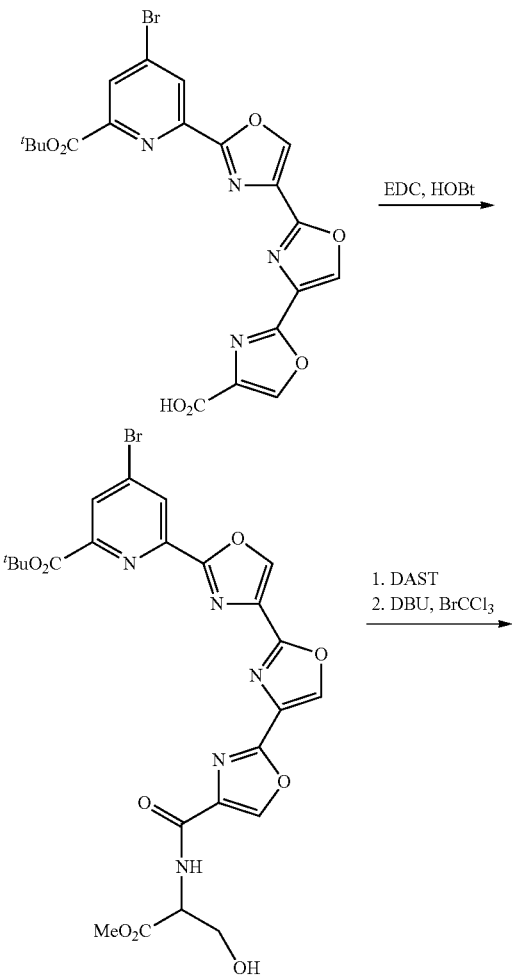

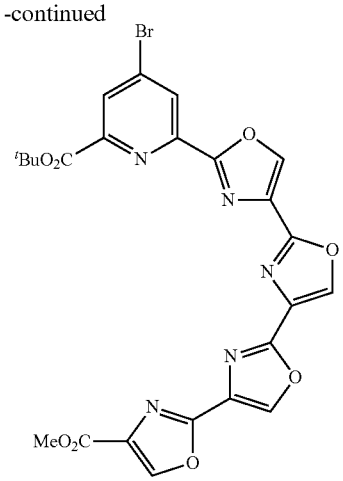

Improved Macrocyclization Procedure

The intermolecular condensation reaction between one acid moiety of the diacid 5 and 1,3-bis(aminomethyl)benzene derivatives followed by intramolecular cyclization (e.g. macrocyclyzation) generally proceeds in only moderate yield due to several factors including the need for the ring-precursor (e.g. diacid 5) to assume a favorable conformation for reaction with the diamine and competing intermolecular reactions. While intermolecular reactions can be minimized by conducting the reaction under high dilution (≤2 mM) conditions, this does not address the problem of reaction conformation. It has been discovered that metal salts can be used to complex the ring-precursor (e.g. diacid 5) in a favorable conformation (e.g. a ring-precursor metal complex) that provides the macrocyclic ring (e.g. 24 membered ring) in higher yield. The use of metal ions of an appropriate size that can bind to the lone-pair electrons on the pyridine ring as well as the lone-pair electrons on the oxazole rings have the potential to orient the diacid into a conformation that is more favorable towards macrocyclic lactam formation. Such a process is shown in Scheme 8.

Scheme 8
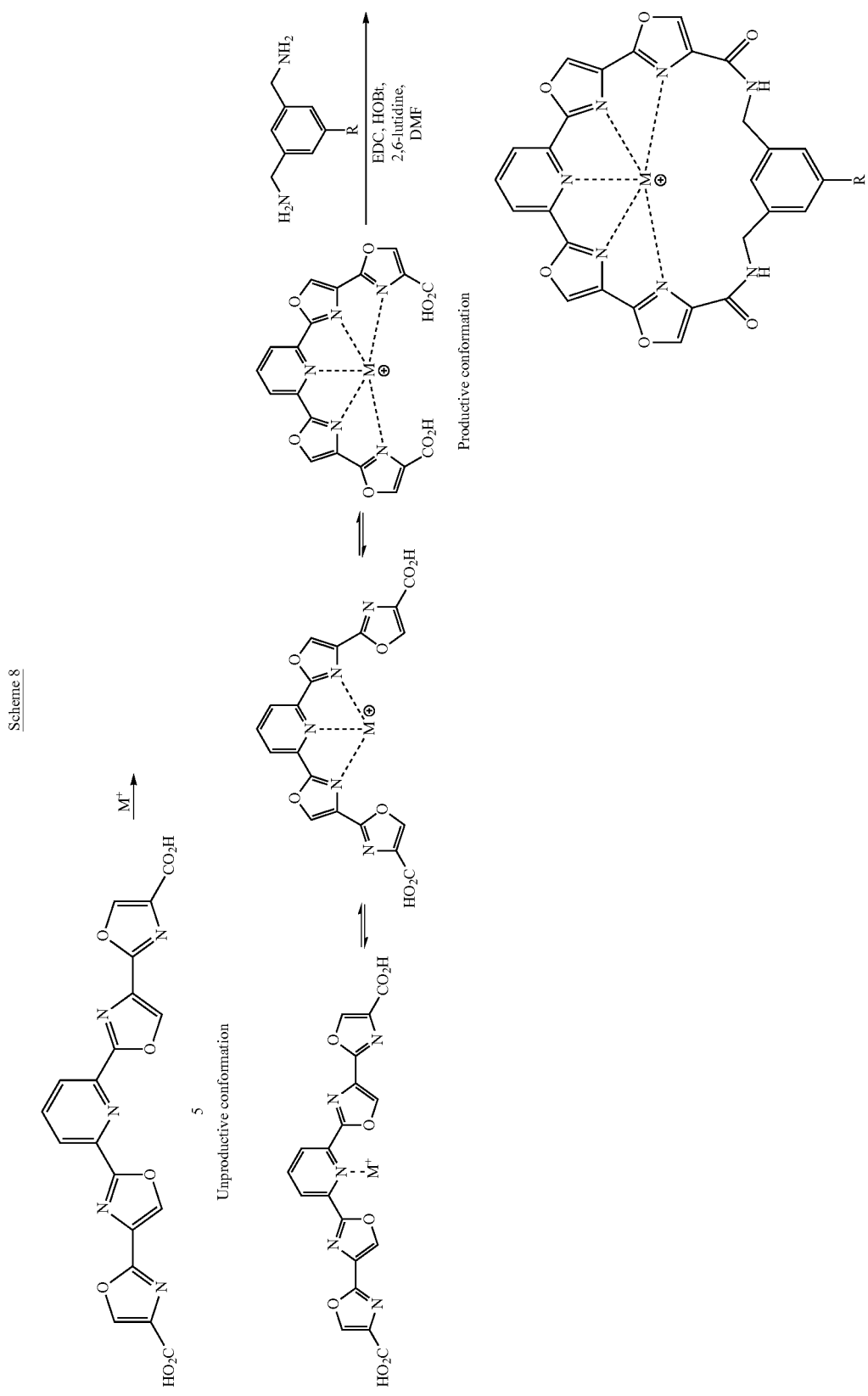

The effectiveness of a variety of metal salts to serve as templates for such a macrocyclization reaction was evaluated for the reaction between the ring precursor 5 and tert-butyl 3,5-bis(aminomethyl)phenethylcarbamate. Complexation between 5 and the metal salts was performed in DMF solution by stirring at 65° C. for 5 minutes (to achieve solution homogeneity). The solution was then allowed to cool to room temperature at which point EDC, HOBt, and 2,6-lutidine were added, followed by the diamine, which was added dropwise as a solution in DMF. The solution (2 mM in DMF) was stirred at room temperature for 48 h.

When the reaction was run in the absence of added metal ion the yield for the macrocyclization was 20%. For the series $R^{6+}$ (61 pm), $Sc^{3+}$ (83 pm), and $Mn^{2+}$ (91 pm) there was a positive correlation between increasing ionic radius and reaction yield with $Mn^{2+}$ giving the greatest yield. For manganese (II) the yield increased when the number of equivalents of the metal increased from 2 to 5 but then decreased upon going to 10 and 50 equivalents. Five equivalents of $Mn^{2+}$ allowed for a homogeneous solution, while 20 and 50 equivalents of the metal did not. A change in solvent to acetonitrile also resulted in a severe drop in yield. The use of an external template, phthalocyanine, either alone or together with $MnSO_4$ did not offer an improvement over metal ion internal templates, and complicated the reaction work-up. The results of this study are summarized in Table 1.

TABLE 1

| Metal Salt | Number of Equivalents | Macrocyclization Yield (%) |
|---|---|---|
| — | — | 20 |
| Sc(OTf)$_3$ | 2 | 26 |
| Re(CO)$_5$Br | 2 | 18 |
| MnSO$_4$ | 2 | 34 |
| MnSO$_4$ | 5 | 42 |
| MnSO$_4$ | 5 | 21[a] |
| MnSO$_4$ | 5 | 8[b] |
| MnSO$_4$ | 10 | 22 |
| MnSO$_4$ | 50 | 14 |
| CoCl$_2$ | 5 | 24 |
| Cr$_2$(SO$_4$)$_3$ | 5 | 27 |
| FeSO$_4$ | 2 | ~0 |
| CuI | 5 | 14 |
| Cu(OTf)$_2$ | 2 | 17 |
| Phthalocyanine[c] | 1 | 29 |
| Phthalocyanine[c] | 1 + 2 eq MnSO$_4$ | 28 |
| Phthalocyanine[c] | 2 + 10 eq MnSO$_4$ | 34 |

[a]Reaction stirred at 65° C. for 48 h
[b]CH$_3$CN was used as the solvent in place of DMF
[c]Phthalocyanine was employed as an external template As used herein the term "metal salt" includes metal salts that when contacted with a ring-precursor form an association between the metal of the metal salt and one or more heteroatoms of the ring-precursor. Such associations can include interactions of the metal with the lone pair of electrons of the ring-precursor heteroatoms. The term "metal salt" includes a suitable metal in combination with an appropriate counterion or ligand. Metals (e.g. metal ions) of the "metal salt" include but are not limited to Sc, Re, Mn, Co, Cr, Fe, Zn and Cu. Counter ions or ligands of the metal salt include but are not limited to halo, carbonyl, sulfate, acetate, triflate and phthalocyanine. Metal salts include but are not limited to Sc (OTf)$_3$, Re(CO)$_5$Br, MnSO$_4$, CoCl$_2$, Cr$_2$(SO$_4$)$_3$, FeSO$_4$, CuI, Cu(OTf)$_2$, Zn(OAc)$_2$ and Mn(phthalocyanine). Metal salts also include metal salts that are prepared in situ by combining a metal salt (e.g. MnSO$_4$) with one or more ligands (e.g. phthalocyanine) to yield an alternative metal salt.

As used herein the term "ring-precursor" includes compounds that when reacted under appropriate conditions form a ring. In one embodiment the ring is a 18-26 membered ring. In another embodiment the ring is a 24 membered ring Accordingly, in one embodiment the invention provides a method comprising preparing an 18-26 membered ring from a ring-precursor comprising:

a. contacting the ring-precursor with a metal salt to form a ring-precursor metal complex; and b. reacting the ring-precursor metal complex under conditions suitable to provide the 18-26 membered ring.

In another embodiment the invention provides a method comprising preparing an 24 membered ring from a ring-precursor comprising:

a. contacting the ring-precursor with a metal salt to form a ring-precursor metal complex; and b. reacting the ring-precursor metal complex under conditions suitable to provide the 24 membered ring.

In one embodiment the ring-precursor comprises one or more heteroatoms selected from N, O and S.

In one embodiment the ring-precursor comprises four or more heteroatoms selected from N, O and S.

In one embodiment the ring-precursor comprises five or more heteroatoms selected from N, O and S.

In one embodiment the ring-precursor comprises one or more groups independently selected from pyridine, phenyl, oxazole, thiazole and imidazole.

In one embodiment the ring-precursor comprises one or more groups independently selected from pyridin-2,6-diyl, 1,3-phenyldiyl, oxazol-2,4-diyl, thiazol-2,4-diyl and imidazol-2,4-diyl.

In one embodiment the ring-precursor comprises 5 groups independently selected from pyridine, phenyl, oxazole, thiazole and imidazole.

In one embodiment the ring-precursor comprises 5 groups independently selected from pyridin-2,6-diyl, 1,3-phenyldiyl, oxazol-2,4-diyl, thiazol-2,4-diyl and imidazol-2,4-diyl.

In one embodiment the ring-precursor comprises 1 group selected from pyridine or phenyl; and 4 groups independently selected from oxazole, thiazole and imidazole.

In one embodiment the ring-precursor comprises one or more groups independently selected from pyridine, phenyl, oxazole, thiazole, imidazole and carboxy.

In one embodiment the ring-precursor comprises one or more groups independently selected from pyridin-2,6-diyl, 1,3-phenyldiyl, oxazol-2,4-diyl, thiazol-2,4-diyl, imidazol-2,4-diyl and carboxy.

In one embodiment the ring-precursor comprises 7 groups independently selected from pyridine, phenyl, oxazole, thiazole, imidazole and carboxy.

In one embodiment the ring-precursor comprises 7 groups independently selected from pyridin-2,6-diyl, 1,3-phenyldiyl, oxazol-2,4-diyl, thiazol-2,4-diyl, imidazol-2,4-diyl and carboxy.

In one embodiment the ring-precursor comprises 1 group selected from pyridine and phenyl; 4 groups independently selected from oxazole, thiazole and imidazole; and 2 carboxy groups.

In one embodiment the ring-precursor is a compound of formula III:

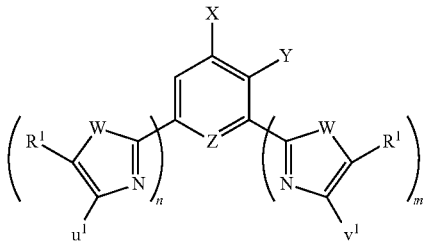

III wherein:
Z is CH or N;
each W is independently NH, S, or O;
n is 1 and m is 3; or n is 2 and m is 2; or n is 3 and m is 1; or n is 4 and m is 0;
X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;
Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;
each $R^1$ is independently H or $(C_1-C_6)$alkyl wherein any $(C_1-C_6)$alkyl of $R^1$ is optionally is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_{a1}R_{b1}$, $-C(=O)NR_{a1}R_{b1}$, and $-NR_{a1}C(=O)-R_{c1}$;
each $R_a$ and $R_b$ is independently H, $(C_1-C_6)$alkyl, $(C_1-C_6)$alkanoyl, or aryl$(C_1-C_6)$alkyl; or $R_a$ and $R_b$ together with the nitrogen to which they are attached form an N-linked heterocycle that is optionally substituted with one or more oxo;
each $R_1$ is $(C_1-C_3)$haloalkyl;
each $R_{a1}$ and $R_{b1}$ is independently H, $(C_1-C_6)$alkyl, $(C_1-C_6)$alkanoyl, or aryl$(C_1-C_6)$alkyl; or $R_{a1}$ and $R_{b1}$ together with the nitrogen to which they are attached form an N-linked heterocycle that is optionally substituted with one or more oxo;
each $R_{c1}$ is halo$(C_1-C_6)$alkyl, $(C_1-C_6)$alkoxy or aryl$(C_1-C_6)$alkoxy; and
-$u^1$ and $v^1$- are each independently $-CO_2H$ or $NH_2$;
or a salt thereof.
In one embodiment -$u^1$ and $v^1$- are each $-CO_2H$.
In one embodiment the 24 membered ring comprises one or more groups independently selected from pyridine, phenyl, oxazole, thiazole and imidazole.

In one embodiment the 24 membered ring comprises one or more groups independently selected from pyridin-2,6-diyl, 1,3-phenyldiyl, oxazol-2,4-diyl, thiazol-2,4-diyl and imidazol-2,4-diyl.
In one embodiment the 24 membered ring comprises 5 groups independently selected from pyridine, phenyl, oxazole, thiazole and imidazole.
In one embodiment the 24 membered ring comprises 5 groups independently selected from pyridin-2,6-diyl, 1,3-phenyldiyl, oxazol-2,4-diyl, thiazol-2,4-diyl and imidazol-2,4-diyl.
In one embodiment the 24 membered ring comprises one or more groups independently selected from pyridine, phenyl, oxazole, thiazole, imidazole and amide.
In one embodiment the 24 membered ring comprises one or more groups independently selected from pyridin-2,6-diyl, 1,3-phenyldiyl, oxazol-2,4-diyl, thiazol-2,4-diyl, imidazol-2,4-diyl and amide.
In one embodiment the 24 membered ring comprises 7 groups independently selected from pyridine, phenyl, oxazole, thiazole, imidazole and amide.
In one embodiment the 24 membered ring comprises 7 groups independently selected from pyridin-2,6-diyl, 1,3-phenyldiyl, oxazol-2,4-diyl, thiazol-2,4-diyl, imidazol-2,4-diyl and amide.
In one embodiment the 24 membered ring comprises a compound of formula (I):

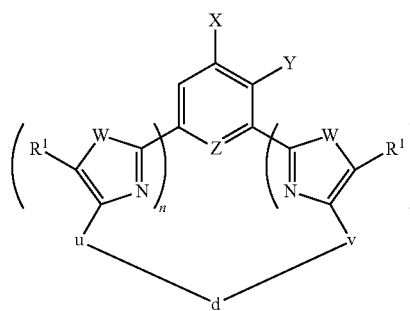

I wherein:
Z is CH or N;
each W is independently NH, S, or O;
n is 1 and m is 3; or n is 2 and m is 2; or n is 3 and m is 1; or n is 4 and m is 0;
X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;
Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_aR_b$, —C(=O)$NR_aR_b$, and —$NR_aC$(=O)—$R_c$;

each $R^1$ is independently H or $(C_1-C_6)$alkyl wherein any $(C_1-C_6)$alkyl of $R^1$ is optionally is optionally substituted with one or more (e.g. 1, 2, 3, or 4) groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —$NR_{a1}R_{b1}$, —C(=O)$NR_{a1},R_{b1}$, and —$NR_{a1}C$(=O)—$R_{c1}$;

each $R_a$ and $R_b$ is independently H, $(C_1-C_6)$alkyl, $(C_1-C_6)$alkanoyl, or aryl$(C_1-C_6)$alkyl; or $R_a$ and $R_b$ together with the nitrogen to which they are attached form an N-linked heterocycle that is optionally substituted with one or more oxo;

each $R_c$ is $(C_1-C_3)$haloalkyl;

each $R_{a1}$ and $R_{b1}$ is independently H, $(C_1-C_6)$alkyl, $(C_1-C_6)$alkanoyl, or aryl$(C_1-C_6)$alkyl; or $R_{a1}$ and $R_{b1}$ together with the nitrogen to which they are attached form an N-linked heterocycle that is optionally substituted with one or more oxo;

each $R_{c1}$ is halo$(C_1-C_6)$alkyl, $(C_1-C_6)$alkoxy or aryl$(C_1-C_6)$alkoxy; and -u-d-v- taken together form an organic radical that comprises a 9 membered chain that taken together with the remainder of formula I forms a compound that comprises a 24 membered ring;

or a salt thereof.

In one embodiment the metal salt is $MnSO_4$.

The ability of a compound of the invention to stabilize G-quadruplex DNA may be determined using pharmacological models which are well known to the art, or using Test A described below.

Test A. Selective Stabilization of G-Quadruplex DNA

Analyses can be performed to determine the ability of the compounds to selectively bind and thermally stabilize quadruplex relative to duplex DNA. Toward this end, the UV absorbances of the DNA molecules are monitored as a function of temperature in the absence and presence of compound. The melting of duplex DNA is generally associated with a hyperchromic shift at 260 nm, while the melting of quadruplex DNA is associated with a hypochromic shift at 295 nm. Thus, the temperature-dependent absorbances of duplex DNA are monitored at 260 nm, with the corresponding quadruplex absorbances being monitored at 295 nm. Salmon testes DNA can be used as a representative model of duplex DNA and $d(T_2AG_3)_4$ can be used as a representative model of quadruplex DNA. All UV melting studies are conducted at physiological pH (7.4) in the presence of potassium ions at physiologically relevant concentrations.

Representative compounds of formula I (compounds 6, 32, and 33) were evaluated for their abilities to selectively bind and stabilize G-quadruplex relative to duplex DNA. The results of these evaluations are summarized in Table 2. Note that all three compounds significantly enhance the thermal stability of the DNA quadruplex ($\Delta T_m$=20.5° C. for 6, $\Delta T_m$=29.5° C. for 32, and $\Delta T_m$=31.5° C. for 33). By contrast, none of the compounds exert any impact on the thermal stability of the DNA duplex ($\Delta T_m$=0° C. for all three compounds). These results indicate that all three compounds bind and stabilize quadruplex DNA with a high degree of specificity relative to duplex DNA.

TABLE 2

Thermal Stabilization of G-Quadruplex Relative to Duplex DNA

| Compound | Human Telomeric G-Quadruplex DNA $\Delta T_m$ (° C.) | Salmon Testes Duplex DNA $\Delta T_m$ (° C.) |
|---|---|---|
| 6 | 20.5 | 0 |
| 32 | 29.5 | 0 |
| 33 | 31.5 | 0 |

Melting experiments were conducted at pH 7.5 in the presence of 50 mM $K^+$. $\Delta T_m$ is defined as the melting temperature ($T_m$) of the drug-DNA complex minus that of the DNA alone.

The anti-proliferative activity of a compound of the invention may be determined using pharmacological models which are well known to the art, or using Test B described below.

Test B. Evaluation of G-Quadruplex Stabilizers using the MTT Assay.

Cell lines are selected based upon one or more factors including data on their relative telomerase activity, varied organ sites, available comparative data, and their ability to form solid tumors in athymic nude mice. The advantage of an MTT assay is that the cytotoxic/cytostatic activities can be readily determined. Cells are cultured for 4 days at 37° C. followed by addition of MTT (3-[4,5-dimethylthiozol-2-yl]-2,5-diphenyltetrazolium bromide (Sigma) (0.1 mg/ml). Cells are treated with MTT for 3 hrs and then dissolved in 100 µl 100% DMSO. Absorbance is measured at $OD_{570}$ using a microplate reader (Model 3550 UV from BIO-RAD). The MTT value is normalized to $OD_{570}$ of cells treated with Cellfectin alone. Stock solutions of each compound are prepared. MTT assays are performed using spectrometric analysis and 96 well plates. The data summarized in Table 3 indicates that all of the compounds listed with the exception of 43 exhibited potent cytotoxicity against the human lymphoblastoma cell line RPMI 8402 ($IC_{50}$ values ranging from 0.09-1.0 µM). All of the compounds in Table 2, which are representative of compounds of formula I, were also cytotoxic against KB3-1 human epidermoid carcinoma tumor cells with $IC_{50}$ values ranging from 0.03 to 1.2 µM.

TABLE 3

Cytotoxicity Data

| | $IC_{50}$ (µM) | |
|---|---|---|
| Compound | RPMI 8402 | KB3-1 |
| 6 | 1.05 | 1.2 |
| 7 | >5 | >5 |
| 8 | >10 | 4 |
| 14 | 1.0 | 0.26 |
| 22 | >10 | >10 |
| 28 | 0.3 | 0.15 |
| 29 | 0.3 | 0.06 |
| 30 | 0.12 | 0.12 |
| 31 | 0.17 | 0.07 |
| 32 | 0.09 | 0.03 |
| 33 | 0.18 | 0.04 |
| 34 | >10 | >10 |
| 35 | 1.0 | 0.6 |
| 36 | >10 | 4 |
| 43 | 4.5 | 0.4 |
| 44 | 1.0 | 1.0 |
| 45 | >10 | >10 |
| 46 | 5 | 3 |
| 47 | >10 | 10 |
| 48 | 0.06 | 0.03 |
| 59 | 3.6 | 3.1 |
| 60 | 9.0 | 7.0 |
| 61 | 2.0 | 0.4 |
| 78 | 0.2 | 0.1 |

The in vivo efficacy with regard to anti-tumor activity can be assessed in athymic nude mice that have human tumor xenografts as described in Test C below.

Test C. Evaluation of G-Quadruplex Stabilizers in the Human Tumor Xenograft Athymic Nude Mouse Model.

Compound 33 inhibited the growth of MDA-MD-435 human tumor xenografts (developed from human melanoma cells) in vivo by more than 50% when administered by ip injection. Bioassays were performed using female NCR/NU NU mice of approximately 9 weeks of age as obtained from Taconic Farms, Inc. (Germantown, N.Y., USA). Mice were housed 4 per cage in laminar flow HEPA filtered microisolator caging (Allentown Caging Equipment Co., Allentown, N.J., USA). Mice were fed Purina autoclavable breeder chow #5021 and given drinking water, purified by reverse-osmosis, ad libitum. Five days after arrival within the animal facility, the mice were inoculated on the right flank with $1.5\times10^6$ MDA-MB-435 tumor cells in 0.1 mL of RPMI 1640 Media by sc injection (25 gauge needle×⅝"). The MDA-MB-435 cells were grown in 75 cm$^2$ flasks using RPMI 1640 Media and 10% fetal bovine serum. Tumors were of sufficient size at 19-20 days after inoculation. Tumor-bearing mice were evenly matched in each experimental group based on tumor volume. Tumor volume was calculated by measuring the tumor with a microcaliper. The length (l) is the maximum two dimensional distance of the tumor and the width (w) is the maximum distance perpendicular to this length measured in mm. Tumor volume was calculated using the formula $(l*w^2)/2$.

The following non-limiting examples illustrate the preparation of representative compounds of formula (I) as well as synthetic intermediates and processes that are useful for preparing compounds of formula (I) and salts thereof.

EXAMPLES

Example 1

Preparation of Representative Compound of the Invention (6)

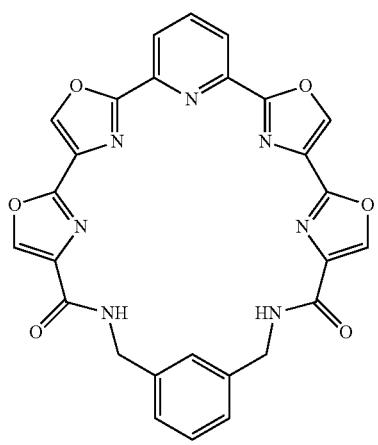

6

Compound 5 (28 mg, 0.065 mmol), EDC (50 mg, 0.26 mmol) and HOBT (35 mg, 0.26 mmol) were partially dissolved in anhydrous DMF (120 mL) and placed under argon. This was cooled to 0° C. and 2,6-lutidine (45 μL, 0.39 mmol) was added followed by m-xylylenediamine (8.5 μL, 0.065 mmol). The reaction stirred at room temperature for 2 days after which the solvent was removed by Kugel-rhor distillation (50° C., 5 mmHg). Water and ethyl acetate was added to the resulting residue and a pale yellow solid precipitated. This was filtered and the solid was dissolved in 10% methanol/CH$_2$Cl$_2$. The solution was passed through basic alumina with 20% methanol/CH$_2$Cl$_2$. This was concentrated to give 10 mg of Compound 6 as a white solid, 30%. Melting point 320-324° C. (decomposed); $^1$H NMR (CDCl$_3$+CD$_3$OD) δ 8.34 (d, 4H, J=5), 8.11, (s, 3H), 7.58 (s, 1H), 7.33 (m, 3H), 4.62 (s, 4H); $^{13}$C NMR (CDCl$_3$+CD$_3$OD) δ 159.8, 159.3, 153.3, 144.1, 140.5, 138.5, 138.0, 136.8, 136.6, 130.7, 129.3, 128.5, 128.1, 121.9, 42.8; IR (thin film NaCl) 3385, 2964, 2921, 2855, 1732, 1666, 1592, 1503, 1439, 1370, 1324, 1288, 1266, 1184, 1100, 986, 918, 822, 778, 734, 708 cm$^{-1}$; HRMS (ESI) m/z calcd for C$_{27}$H$_{17}$N$_7$O$_6$Na (M+Na) 558.1138; found 558.1118

The intermediate compound 5 was prepared as follows.

a. Preparation of Compound 1

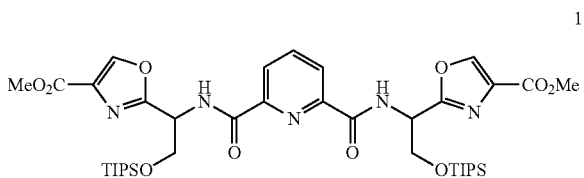

1

2.6-pyridinedicarboxylic acid (418 mg, 2.5 mmol), methyl 2-(1-amino-2-(triisopropylsilyloxy)ethyl)oxazole-4-carboxylate (1.71 g, 5 mmol), EDC (1.92 g, 10 mmol) and HOBT (1.35 g, 10 mmol) were dissolved in anhydrous DMF (100 mL). 2,6-Lutidine (2.9 mL, 25 mmol) was added and the reaction mixture was placed under argon prior to cooling to 0° C. The reaction mixture warmed to room temperature overnight and then the solvent was removed via Kugel-rhor distillation (50° C., 5 mmHg). The resulting residue was taken up in a mixture of ethyl acetate and water and the layers were separated. The organic layer was washed with water and brine. This was then dried with Na$_2$SO$_4$ and concentrated to yellow oil that was flash chromatographed on SiO$_2$ with 15-50% ethyl acetate/hexane. Compound 1 was isolated as a pale yellow oil weighing 1.6 g, 80%. $^1$H NMR (CDCl$_3$) δ 8.54 (d, 2H, J=8), 8.38 (d, 2H, J=8), 8.24 (s, 2H), 8.04 (t, 1H, J=7), 5.62 (dt, 2H, J=6, 9), 4.26 (d, 4H, J=7), 3.90 (s, 6H), 0.96 (m, 42H); $^{13}$C NMR (CDCl$_3$) δ 162.6, 162.4, 147.7, 143.2, 138.1, 132.6, 124.9, 122.4, 63.6, 51.2, 49.3, 16.9, 10.9; IR (thin film, NaCl) 3501, 3304, 3166, 3107, 2945, 2891, 2867, 2362, 2251, 1740, 1681, 1583, 1526, 1463, 1440, 1385, 1367, 1343, 1323, 1248, 1201, 1114, 1071, 1000, 918, 883, 845, 802, 734, 684, 646 cm$^{-1}$; HRMS (ESI) m/z calcd for C$_{39}$H$_{61}$N$_5$O$_{10}$Si$_2$Na (M+Na) 838.3855; found 838.3859.

b. Preparation of Compound 2

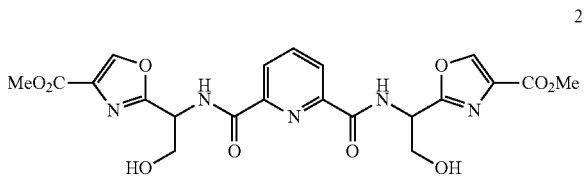 [SMILES: COC(=O)c1coc(C(CO)NC(=O)c2cccc(C(=O)NC(CO)c3nc(C(=O)OC)co3)n2)n1]

2

Compound 1 (750 mg, 0.92 mmol) was dissolved in a mixture of anhydrous THF (20 mL) and pyridine (2 mL) followed by the addition of HF-pyridine complex (0.5 mL) The reaction stirred under a drying tube overnight at room temperature and a white solid precipitated. A saturated solution of NaHCO$_3$ was added forming a white precipitate which was filtered and washed with water. The solid was collected and the aqueous filtrate was extracted with $CH_2Cl_2$. The organic solution was dried with $Na_2SO_4$ and concentrated in vacuo to a white solid. This was combined with the filtered solid to give 463 mg of Compound 2 as a white solid, 100%. Melting point 218-220° C.; $^1$H NMR (DMSO) δ 9.58 (d, 2H, J=8), 8.84 (s, 2H), 8.24 (m, 3H), 5.29 (m, 2H), 4.04 (m, 4H), 3.79 (s, 6H); $^{13}$C NMR (DMSO) δ 163.3, 162.7, 160.9, 148.2, 145.4, 132.1, 125.1, 60.8, 51.6, 50.0; IR (Nujol) 3500, 3364, 3287, 3131, 1732, 1679, 1576, 1537, 1456, 1377, 1329, 1256, 1199, 1147, 1108, 1080, 1043, 993, 957, 870, 829, 799, 720, 679 cm$^{-1}$ HRMS (ESI) m/z calcd for $C_{21}H_{21}N_5O_{10}Na$ (M+Na) 526.1186; found 526.1191.

c. Preparation of Compound 3

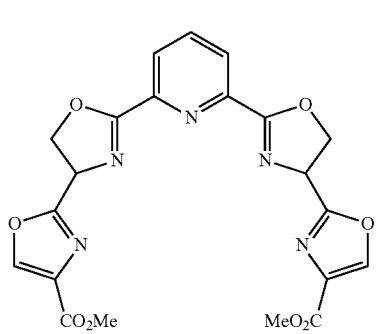

3

Compound 2 (463 mg, 0.92 mmol) was suspended in anhydrous $CH_2Cl_2$ (30 mL) and placed under argon. After cooling to −78° C., DAST (0.3 mL, 2.3 mmol) was added and the reaction stirred for 4 hours at low temperature. Then $K_2CO_3$ (317 mg, 2.3 mmol) was added and the reaction mixture warmed to room temperature. This was poured into a solution of saturated $NaHCO_3$ and extracted with $CH_2Cl_2$. The combined organic extracts were dried with $Na_2SO_4$ and concentrated to give Compound 3 as a white solid weighing 428 mg, 100%.

Melting point 214-217° C.; $^1$H NMR (CD$_3$OD) δ 8.36 (s, 2H), 8.26 (d, 2H, J=8), 8.01 (t, 1H, J=8), 5.67 (t, 2H, J=9), 4.97 (d, 4H, J=8), 4.28 (s, 6H); $^{13}$C NMR (CD$_3$OD) δ 165.5, 163.1, 161.5, 146.0, 145.1, 138.0, 133.3, 126.9, 71.4, 63.7, 52.1; IR (Nujol) 3115, 1725, 1631, 1587, 1574, 1461, 1436, 1384, 1365, 1330, 1317, 1244, 1204, 1141, 1121, 1109, 1072, 995, 977, 938, 913, 845, 810, 774, 737 cm$^{-1}$; HRMS (ESI) m/z calcd for $C_{21}H_{17}N_5O_8Na$ (M+Na) 490.0975; found 490.0984.

d. Preparation of Compound 4

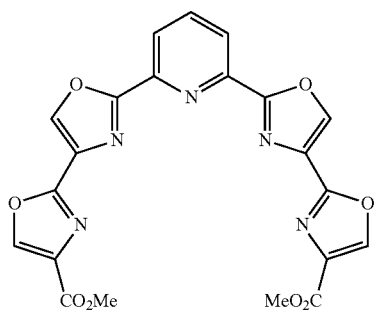

4

Compound 3 (428 mg, 0.92 mmol) was suspended in anhydrous $CH_3CN$ (40 mL) and placed under argon. This was cooled to 0° C. and treated dropwise with DBU (0.55 mL, 3.68 mmol) and BrCCl$_3$ (0.44 mL, 4.42 mmol). The reaction warmed to room temperature overnight and a white precipitate formed. This was filtered and washed with $CH_2Cl_2$ to give Compound 4 as a white solid weighing 341 mg, 80%. Melting point 220° C. (decomposed); $^1$H NMR (CDCl$_3$) δ 8.59 (s, 2H), 8.44 (d, 2H, J=8), 8.37 (s, 2H), 8.08 (t, 1H, J=8), 3.98 (s, 6H); IR (thin film NaCl) 3124, 2359, 1727, 1647, 1568, 1523, 1439, 1367, 1325, 1313, 1281, 1258, 1199, 1151, 1116, 1094, 1074, 997, 970, 928, 913, 839, 817, 809, 773, 734, 714 cm$^{-1}$; HRMS (ESI) m/z calcd for $C_{21}H_{13}N_5O_8Na$ (M+Na) 486.0662; found 486.0673.

e. Preparation of Compound 5

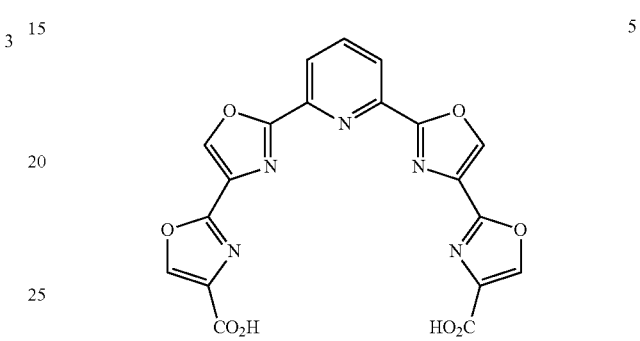

5

Compound 4 (150 mg, 0.32 mmol) was suspended in a mixture of THF (50 mL) and water (15 mL) and LiOH (30 mg, 0.71 mmol) was added. This was refluxed overnight followed by partial concentration in vacuo to remove THF. The resulting white precipitate was treated with 5% HCl, filtered and washed with water. This produced 140 mg of Compound 5 as a white solid, 100%. Melting point 315-318° C. (decomposed); IR (Nujol) 2367, 2334, 1727, 1455, 1376, 1326, 1315, 1156, 1115, 1074, 1003, 975, 915, 822, 773, 740, 718 cm$^{-1}$; HRMS (ESI) m/z calcd for $C_{19}H_9N_5O_8Na$ (M+Na) 458.0349; found 458.0353.

Example 2

Preparation of Representative Compound of the Invention (7)

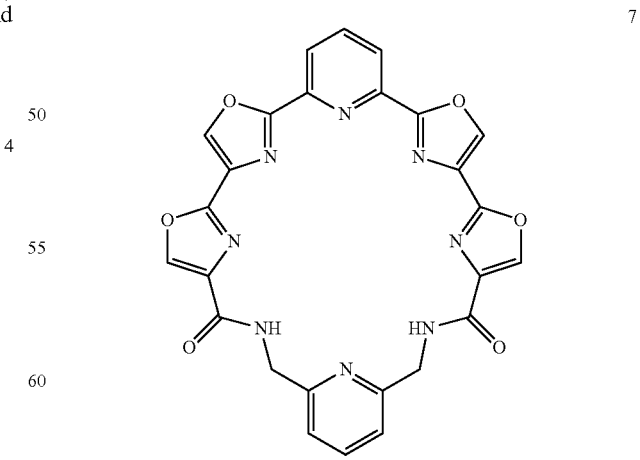

7

Compound 5 (40 mg, 0.092 mmol), EDC (71 mg, 0.37 mmol) and HOBT (50 mg, 0.37 mmol) were partially dissolved in anhydrous DMF (120 mL) and placed under argon. This was cooled to 0° C. and 2,6-lutidine (64 μL, 0.55 mmol)

was added followed by a solution of pyridine-2,6-diylmethanamine (13 µL, 0.092 mmol) in 1 mL of DMF over 1 hour. The reaction then stirred at room temperature for 2 days after which the solvent was removed by Kugel-rhor distillation (50° C., 5 mmHg). Water and ethyl acetate was added to the resulting residue and a pale yellow solid precipitated. This was filtered and the solid was dissolved in 10% methanol/CH$_2$Cl$_2$. The solution was passed through basic alumina with 20% methanol/CH$_2$Cl$_2$. This was concentrated to give 11 mg of Compound 7 as a white solid, 22%. Melting point 330° C. (decomposed); $^1$H NMR (CDCl$_3$+CD$_3$OD) δ 8.33 (s, 4H), 8.09 (s, 3H), 7.72 (t, 1H, J=8), 7.40 (d, 2H, J=8), 4.76 (s, 4H); $^{13}$C NMR (CDCl$_3$+CD$_3$OD) δ 159.8, 159.5, 144.3, 140.4, 138.3, 137.8, 137.4, 136.4, 130.8, 122.5, 121.7, 71.2; IR (thin film NaCl) 3384, 2920, 2855, 1732, 1647, 1600, 1523, 1441, 1370, 1332, 1178, 1101, 975, 921, 827, 734, 712 cm$^{-1}$; HRMS (ESI) m/z calcd for C$_{26}$H$_{16}$N$_8$O$_6$Na (M+Na) 559.1091; found 559.1071.

Example 3

Preparation of Representative Compound of the Invention (8)

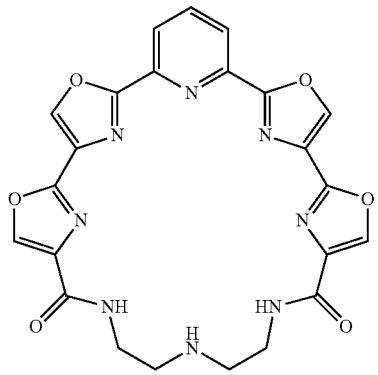

8

Compound 5 (23 mg, 0.053 mmol) and copper (II) triflate (19 mg, 0.053 mmol) were partially dissolved in anhydrous DMF (100 mL) and placed under argon. This stirred at room temperature for 3 hours after which EDC (41 mg, 0.21 mmol) and HOBT (29 mg, 0.21 mmol) were added. The solution immediately became bright yellow. This was cooled to 0° C. and 2,6-lutidine (37 µL, 0.32 mmol) was added followed by a solution of diethylenetriamine (6 µL, 0.053 mmol) in 0.5 mL of DMF over 30 minutes. The reaction then stirred at room temperature for 2 days and the solution became pale blue. The solvent was removed by Kugel-rhor distillation (50° C., 5 mmHg). Water and ethyl acetate was added to the resulting residue and a pale yellow solid precipitated. This was filtered and the solid material was flash chromatographed on SiO$_2$ with 0.5-30% methanol/CH$_2$Cl$_2$ with 1% Et$_3$N. After concentration, the solid was dissolved in 25% methanol CH$_2$Cl$_2$ and treated with IRA-400 to remove triethylammonium generated by chromatography. The resin was filtered off and the liquid was concentrated to give 4 mg of Compound 8 as a white solid, 15%. Melting point 276° C. (decomposed); $^1$H NMR (CDCl$_3$+CD$_3$OD) δ 8.47 (s, 2H), 8.37 (s, 2H), 8.19 (s, 3H), 3.98 (m, 4H) 3.35 (m, 4H); IR (thin film NaCl) 3383, 2959, 2921, 2855, 2362, 1732, 1651, 1595, 1523, 1436, 1375, 1321, 1260, 1173, 1110, 981, 916, 816, 734, 718 cm$^{-1}$; HRMS (ESI) m/z calcd for C$_{23}$H$_{18}$N$_8$O$_6$Na (M+Na) 525.1247; found 525.1228.

Example 4

Preparation of Representative Compound of the Invention (14)

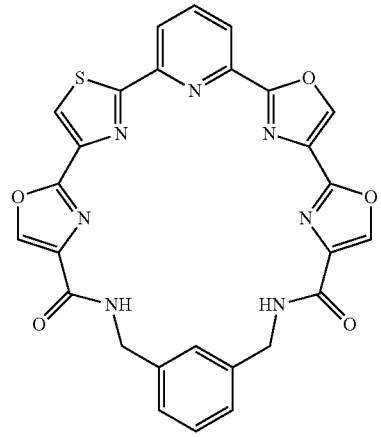

14

Compound 13 (23 mg, 0.051 mmol) and copper (II) triflate (18 mg, 0.051 mmol) were partially dissolved in anhydrous DMF (100 mL) and placed under argon. This stirred at room temperature for 3 hours after which EDC (40 mg, 0.20 mmol) and HOBT (28 mg, 0.20 mmol) were added. The solution immediately became bright yellow. This was cooled to 0° C. and 2,6-lutidine (36 µL, 0.31 mmol) was added followed by a solution of m-xylylenediamine (7 µL, 0.051 mmol) in 0.5 mL of DMF over 30 minutes. The reaction then stirred at room temperature for 2 days and the solution became pale blue. The solvent was removed by Kugel-rhor distillation (50° C., 5 mmHg). Water and ethyl acetate was added to the resulting residue and a pale yellow solid precipitated. This was filtered and the solid collected. The remaining filtrate was extracted with ethyl acetate and dried with Na$_2$SO$_4$. After concentration this was combined with the filtered solid and chromatographed on SiO$_2$ with 0.5-30% methanol/CHCl$_3$ with 1% Et$_3$N. After concentration, the solid was dissolved in 25% methanol CH$_2$Cl$_2$ and treated with IRA-400 to remove triethylammonium generated by chromatography. The resin was filtered off and the liquid was concentrated to give 9 mg of Compound 14 as a white solid, 33%. Melting point 274-275° C. (decomposed); $^1$H NMR (CDCl$_3$) δ 8.31 (s, 1H), 8.28 (s, 1H), 8.26 (s, 1H), 8.00 (m, 4H), 7.37 (m, 4H), 4.62, (m, 4H); $^{13}$C NMR (CDCl$_3$) δ 140.0, 139.7, 138.4, 137.9, 136.7, 128.8, 128.3, 127.8, 127.4 123.1, 121.9, 120.6, 113.4, 42.9, 42.3; IR (thin film NaCl) 3384, 1659, 1593, 1500, 1447, 1364, 1315, 1282, 1260, 1178, 1111, 981, 921, 816, 729, 709 cm$^{-1}$.

The intermediate Compound 13 was prepared as follows.
a. Preparation of Compound 9

9

Compound 1 (100 mg, 0.12 mmol) was dissolved in toluene (10 mL) and placed under argon. Then Lawesson's reagent (50 mg, 0.12 mmol) was added and the reaction mixture was heated to 80° C. for 4 hours. After cooling to room temperature, the solvent was removed in vacuo and the residue was flash chromatographed on SiO$_2$ with 5-25% ethyl acetate/hexane to give 54 mg of Compound 9 as pale yellow oil, 53%. $^1$H NMR (CDCl$_3$) δ 10.46 (d, 1H, J=8), 8.82, (dd, 1H, J=1, 9), 8.62 (d, 1H, J=8), 8.36 (dd, 1H, J=1, 8), 8.31 (s, 1H), 8.23 (s, 1H), 8.00 (t, 1H, J=6), 6.19 (dt, 1H, J=3, 5), 5.61 (dt, 1H, J=2, 6), 4.38 (d, 2H, J=5), 4.26 (d, 2H, 6), 3.88 (s, 6H), 0.95 (m, 42H); $^{13}$C NMR (CDCl$_3$) δ 190.7, 170.3, 162.7, 162.6, 161.6, 160.4, 146.5, 143.5, 143.2, 137.7, 133.0, 127.5, 124.6, 62.6, 54.7, 51.2, 49.4; IR (thin film, NaCl) 3485, 3414, 3268, 3166, 3107, 2944, 2899, 2866, 2767, 2726, 2564, 2360, 2340, 2247, 1940, 1743, 1682, 1583, 1519, 1463, 1442, 1323, 1266, 1201, 1114, 1071, 999, 921, 883, 838, 801, 766, 740, 685, 611 cm$^{-1}$; HRMS (ESI) m/z calcd for C$_{39}$H$_{61}$N$_5$O$_9$SSi$_2$Na (M+Na) 854.3626; found 854.3612.

b. Preparation of Compound 10

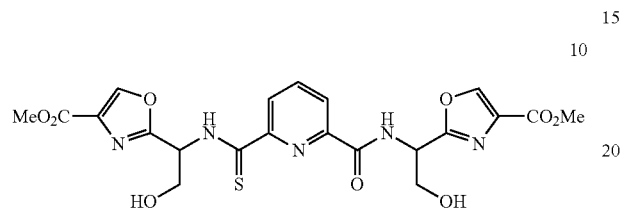

10

Compound 9 (138 mg, 0.17 mmol) was dissolved in a mixture of anhydrous THF (8 mL) and pyridine (0.5 mL) followed by the addition of HF-pyridine complex (0.3 mL). The reaction stirred under a drying tube overnight at room temperature before being poured into a saturated solution of NaHCO$_3$. This was extracted with CH$_2$Cl$_2$ and the organic solution was dried with Na$_2$SO$_4$. Concentration in vacuo resulted in a pale yellow solid weighing 81 mg, 94%. Melting point 169-171° C.; $^1$H NMR (CDCl$_3$+CD$_3$OD) δ 11.06 (d, 1H, J=8), 9.39 (d, 1H, J=9), 8.84 (d, 1H, J=8), 8.33 (m, 4H), 8.07 (t, 1H, J=8), 6.16 (m, 1H), 5.56 (dt, 1H, J=4, 8), 4.22 (m, 4H), 3.88 (s, 6H); $^{13}$C NMR (CDCl$_3$+CD$_3$OD) δ 190.7, 163.0, 162.5, 161.6, 160.5, 149.4, 146.1, 143.7, 137.9, 132.1, 131.9, 127.3, 124.2, 62.1, 61.2, 54.4, 51.3, 49.2; IR (thin film, NaCl) 3289, 3129, 2953, 2592, 2356, 1716, 1668, 1589, 1519, 1441, 1321, 1216, 1189, 1136, 1112, 1069, 793 cm$^{-1}$ c. Preparation of Compound 11

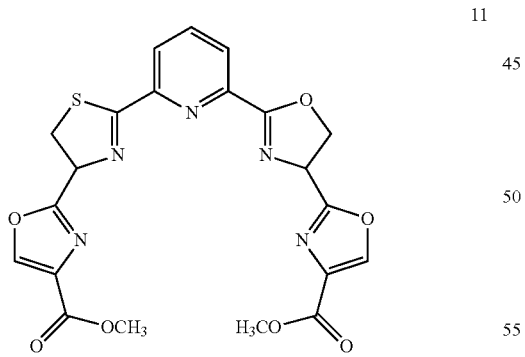

11

Compound 10 (80 mg, 0.15 mmol) was suspended in anhydrous CH$_2$Cl$_2$ (10 mL) and placed under argon. After cooling to −78° C., DAST (0.51 µL, 0.39 mmol) was added and the reaction stirred for 4 hours at low temperature. Then K$_2$CO$_3$ (54 mg, 0.39 mmol) was added and the reaction mixture warmed to room temperature. This was poured into a solution of saturated NaHCO$_3$ and extracted with CH$_2$Cl$_2$. The combined organic extracts were dried with Na$_2$SO$_4$ and concentrated to give Compound 10 as a white solid weighing 75 mg, 100%. Melting point 195-197° C.; $^1$H NMR (CDCl$_3$) δ 8.24 (m, 4H), 7.90 (t, 1H, J=8), 5.92 (t, 1H, J=10), 5.66 (m, 1H), 4.95 (m, 2H), 3.86 (m, 8H); $^{13}$C NMR (CDCl$_3$) δ 172.6, 164.3, 162.3, 162.2, 160.5, 149.7, 144.9, 144.0, 143.8, 136.6, 132.6, 125.9, 123.3, 73.2, 70.4, 63.1, 51.4, 34.8; IR (thin film, NaCl) 3162, 3113, 2954, 2359, 2334, 1722, 1636, 1580, 1450, 1435, 1375, 1322, 1241, 1220, 1200, 1181, 1143, 1110, 1081, 1036, 1004, 953, 933, 853, 827, 807, 763, 736, 698, 643 cm$^{-1}$ d. Preparation of Compound 12

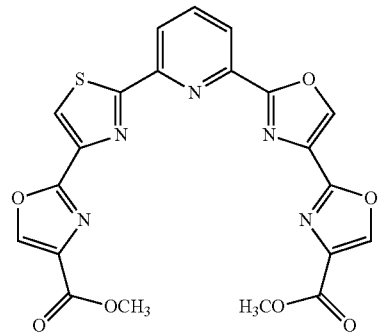

12

Compound 11 (75 mg, 0.16 mmol) was suspended in anhydrous CH$_3$CN (8 mL) and placed under argon. This was cooled to 0° C. and treated dropwise with DBU (0.93 µL, 0.62 mmol) and BrCCl$_3$ (0.74 µL, 0.75 mmol). The reaction warmed to room temperature overnight and a white precipitate formed. This was filtered and washed with CH$_3$CN to give Compound 12 as a white solid weighing 57 mg, 77%. Melting point 215° C. (decomposed) 305-310° C. (melted); $^1$H NMR (CDCl$_3$+CD$_3$OD) δ 8.62 (s, 1H), 8.49 (d, 1H, J=7), 8.35 (m, 4H), 8.06 (m, 1H), 3.98 (s, 6H); IR (thin film NaCl) 3414, 3156, 3112, 2964, 2855, 1724, 1635, 1573, 1521, 1441, 1325, 1223, 1192, 1111, 1024, 996, 970, 767, 726 cm$^{-1}$.

e. Preparation of Compound 13

13

Compound 12 (57 mg, 0.12 mmol) was suspended in a mixture of THF (10 mL) and water (3 mL) and LiOH (11 mg, 0.26 mmol) was added. This was refluxed overnight followed by partial concentration in vacuo to remove THF. This resulted in a white precipitate that was treated with 5% HCl, filtered and washed with water. This gave 42 mg of Compound 13 as a white solid, 78%. Melting point 274-276° C. (decomposed); $^1$H NMR (CD$_3$OD) δ 8.84 (s, 1H), 8.71 (m, 4H), 8.40 (m, 2H); IR (thin film NaCl) 1726, 1572, 1474, 1441, 1327, 1156, 1111, 1022, 970, 818, 785, 725 cm$^{-1}$.

Example 5

Preparation of Representative Compound of the Invention (22)

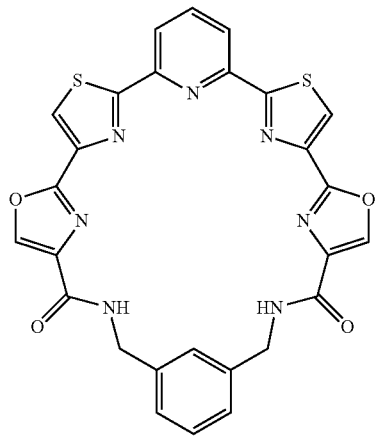

22

Compound 21 (20 mg, 0.025 mmol), EDC (10 mg, 0.05 mmol) and HOBT (7 mg, 0.05 mmol) were dissolved in anhydrous DMF (35 mL) and placed under argon. Then 2,6-lutidine (20 µL, 0.17 mmol) was added and the reaction stirred at room temperature overnight. The solvent was removed by Kugel-rhor distillation (50° C., 5 mmHg) and water and ethyl acetate were added to the resulting residue. A white solid precipitated and was filtered while the resulting filtrate was extracted with ethyl acetate. The organic extract was dried with $Na_2SO_4$ and added to the filtered solid. Concentration in vacuo resulted in a yellow solid which was chromatographed on $SiO_2$ with 2-25% methanol/$CHCl_3$ with 0.5% $Et_3N$. After concentration, the solid was dissolved in 25% methanol $CH_2Cl_2$ and treated with IRA-400 to remove triethylammonium generated by chromatography. The resin was filtered off and the liquid was concentrated to give 6 mg of product as a white solid, 43%. Melting point 245° C.; $^1H$ NMR ($CDCl_3$+$CD_3OD$) δ 8.38 (m, 4H), 8.42 (s, 2H), 7.97 (m, 2H), 7.30 (m, 3H), 4.63 (d, 4H, J=6) $^{13}C$ NMR ($CDCl_3$+ $CD_3OD$) δ 140.7, 137.4, 136.0, 128.4, 126.6, 126.5, 123.2, 120.5, 42.6 IR (thin film NaCl) 3261, 1703, 1653, 1595, 1567, 1518, 1436, 1364, 1310, 1216, 1184, 1156, 1112, 1001, 899, 822, 789, 739 cm$^{-1}$; HRMS (ESI) m/z calcd for $C_{27}H_{18}N_7O_4S_2$ (M+H): 568.08625; found: 568.0864.

The intermediate Compound 21 was prepared as follows.

a. Preparation of Compound 15

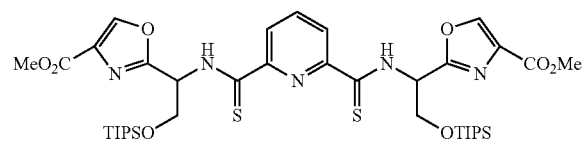

15

Compound 1 (100 mg, 0.12 mmol) was dissolved in toluene (10 mL) and placed under argon. Then Lawesson's reagent (150 mg, 0.37 mmol) was added and the reaction mixture was heated to 80° C. for 4 hours. After cooling to room temperature, the solvent was removed in vacuo and the residue was flash chromatographed on $SiO_2$ with 5-25% ethyl acetate/hexane to give 91 mg of Compound 15 as yellow oil, 88%. $^1H$ NMR ($CDCl_3$) δ 10.26 (d, 2H, J=8), 8.79 (d, 2H, J=8), 8.29 (s, 2H), 7.97 (t, 1H, J=8), 6.18 (dt, 2H, J=3, 6), 4.37 (m, 4H), 3.88 (s, 6H), 1.00 (m, 42H); $^{13}C$ NMR ($CDCl_3$) δ 190.9, 161.5, 160.3, 148.7, 143.5, 137.4, 132.6, 127.1, 62.6, 54.7, 51.2, 16.8, 10.9.

b. Preparation of Compound 16

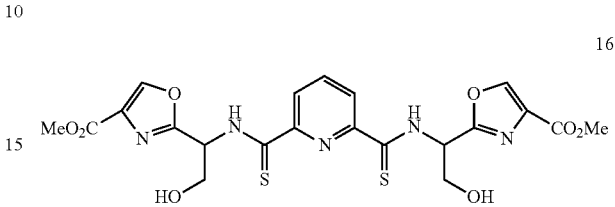

16

Compound 15 (125 mg, 0.15 mmol) was dissolved in a mixture of anhydrous THF (5 mL) and pyridine (0.4 mL) followed by the addition of HF-pyridine complex (0.3 mL). The reaction stirred under a drying tube overnight at room temperature before being poured into a saturated solution of $NaHCO_3$. This was extracted with $CH_2Cl_2$ and the organic solution was dried with $Na_2SO_4$. Concentration in vacuo provided Compound 16 as a yellow solid weighing 79 mg, 100%. Melting point 136-139° C.; $^1H$ NMR ($CDCl_3$) δ 10.99 (d, 2H, J=7), 7.34 (d, 2H, J=8), 8.23 (s, 2H), 8.01 (t, 1H, J=8), 6.19 (d, 2H, J=10), 4.33 (m, 4H), 3.89 (s, 6H) IR (thin film NaCl) 3319, 2964, 1731, 1677, 1589, 1514, 1353, 1326, 1211, 1111, 1079, 1003, 921, 833, 773, 734 cm$^{-1}$; HRMS (ESI) m/z calcd for $C_{21}H_{21}N_5O_8S_2Na$ (M+Na) 558.0729; found 558.0715.

c. Preparation of Compound 17

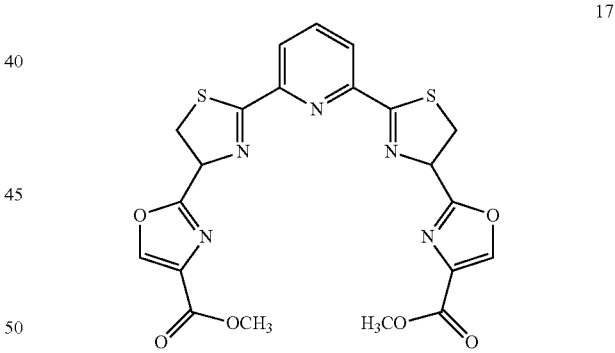

17

Compound 16 (79 mg, 0.15 mmol) was suspended in anhydrous $CH_2Cl_2$ (8 mL) and placed under argon. After cooling to −78° C., DAST (0.51 µL, 0.39 mmol) was added and the reaction stirred for 4 hours at low temperature. Then $K_2CO_3$ (54 mg, 0.39 mmol) was added and the reaction mixture warmed to room temperature. This was poured into a solution of saturated $NaHCO_3$ and extracted with $CH_2Cl_2$. The combined organic extracts were dried with $Na_2SO_4$ and concentrated to give Compound 17 as an orange solid weighing 62 mg, 81%. Melting point 260° C. (decomposed); $^1H$ NMR ($CDCl_3$) δ 8.28 (s, 2H), 8.22 (d, 2H, J=8), 7.87 (t, 1H, J=8), 5.94 (t, 2H, J=10), 3.93 (s, 6H), 3.81 (dd, 4H, J=3, 10); $^{13}C$ NMR ($CDCl_3$) δ 172.5, 162.4, 160.5, 149.1, 143.8, 136.5, 132.7, 122.9, 73.3, 51.4, 34.6; IR (thin film, NaCl) 3424, 2950, 2084, 1722, 1642, 1601, 1579, 1439, 1316, 1288, 1263, 1239, 1200, 1144, 1111, 998, 948, 917, 736 cm$^{-1}$ HRMS (ESI) m/z calcd for $C_{21}H_{17}N_5O_6S_2Na$ (M+Na) 522.0518; found 522.0497.

d. Preparation of Compound 18

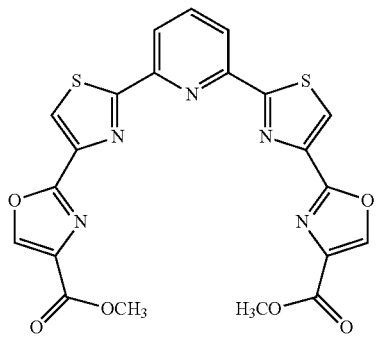

Compound 17 (62 mg, 0.12 mmol) was suspended in anhydrous $CH_3CN$ (8 mL) and placed under argon. This was cooled to 0° C. and treated dropwise with DBU (0.74 μL, 0.5 mmol) and $BrCCl_3$ (0.59 μL, 0.6 mmol). The reaction warmed to room temperature overnight and a white precipitate formed. This was filtered and washed with $CH_3CN$ to give Compound 18 as a white solid weighing 60 mg, 98%. Melting point 330-333° C. (decomposed); IR (thin film NaCl) 3147, 3111, 3009, 2959, 1724, 1585, 1571, 1475, 1438, 1327, 1302, 1224, 1192, 1150, 1113, 1006, 947, 891, 816, 787, 778, 765, 725, 653, 641 cm$^{-1}$; HRMS (ESI) m/z calcd for $C_{21}H_{13}N_5O_6S_2Na$ (M+Na) 518.0205; found 518.0184.

e. Preparation of Compound 19

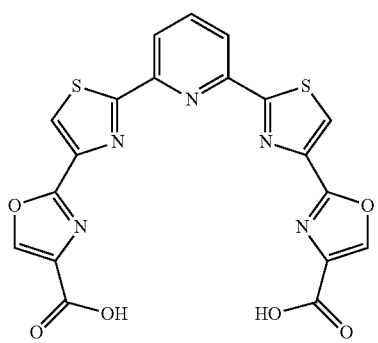

Compound 18 (52 mg, 0.11 mmol) was suspended in a mixture of THF (10 mL) and water (3 mL) and LiOH (10 mg, 0.23 mmol) was added. This was refluxed overnight followed by partial concentration in vacuo to remove THF. This resulted in a white precipitate that was treated with 5% HCl, filtered and washed with water. This resulted in 49 mg of Compound 19 as a white solid, 100%. Melting point 275-277° C. (decomposed); IR (Nujol) 1713, 1160, 1568, 1456, 1375, 1293, 1216, 1162, 1114, 1000, 816, 725 cm$^{-1}$; HRMS (ESI) m/z calcd for $C_{19}H_9N_5O_6S_2Na$ (M+Na) 489.9892; found 489.9874.

f. Preparation of Compound 20

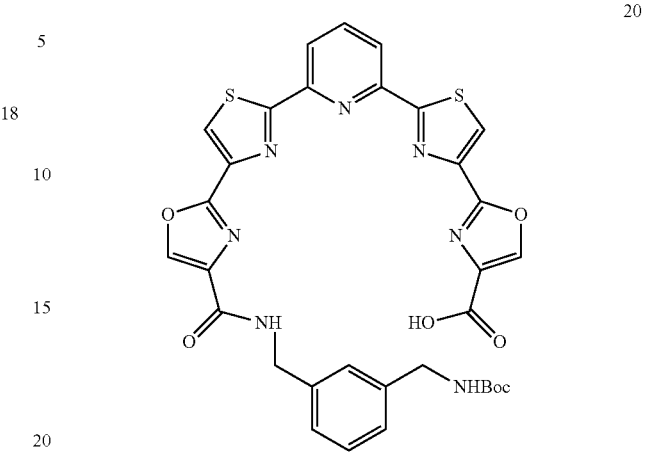

Compound 19 (21 mg, 0.045 mmol), EDC (17 mg, 0.09 mmol) and HOBT (12 mg, 0.09 mmol) were dissolved in anhydrous DMF (30 mL) and placed under argon. This was cooled to 0° C. and 2,6-lutidine (26 μL, 0.23 mmol) was added followed by 1-(N-Boc-aminomethyl)-3-(aminomethyl)benzene (11 μL, 0.045 mmol). The reaction warmed to room temperature overnight after which the solvent was removed by Kugel-rhor distillation (50° C., 5 mmHg). Water and ethyl acetate was added to the resulting residue and a white solid precipitated. This was filtered and the remaining filtrate was extracted with ethyl acetate and dried with $Na_2SO_4$. After concentration this was combined with the filtered solid to give 34 mg of Compound 20 as a white solid. Melting point 111-114° C.; $^1H$ NMR ($CDCl_3+CD_3OD$) δ 8.37 (m, 3H), 8.16 (s, 2H), 7.98 (t, 1H, J=8), 7.26 (m, 4H), 4.63 (d, 2H, J=4), 4.31 (s, 2H); $^{13}C$ NMR ($CDCl_3+CD_3OD$) δ 169.0, 159.6, 156.0, 155.1, 149.2, 143.0, 140.6, 138.6, 137.8, 137.1, 136.1, 128.2, 126.1, 125.8, 125.4, 123.1, 120.6, 116.2, 110.2, 78.8, 43.5, 42.2, 27.5; IR (thin film NaCl) 3330, 3112, 2976, 2932, 1672, 1593, 1566, 1513, 1446, 1365, 1252, 1165, 1107, 1001, 818, 780, 739 cm$^{-1}$ g. Preparation of Compound 21

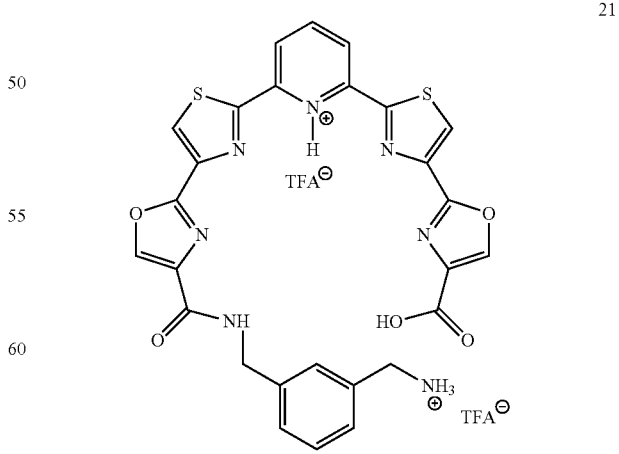

Compound 20 (34 mg crude) was partially dissolved in dry $CH_2Cl_2$ (3 mL) and cooled to 0° C. before being treated with TFA (3 mL). This stirred at 0° C. for 2 hours, then the solvent was removed in vacuo. The resulting solid was azeotroped twice with benzene and washed with CH₂Cl₂. This gave 25 mg of product as a white solid, 68% yield over 2 steps. Melting point 234° C. (decomposed); IR (thin film NaCl) 3390, 1668, 1584, 1518, 1441, 1200, 1178, 1113, 1003, 915, 822, 734, 712 cm$^{-1}$.

Example 6

Preparation of Representative Compound of the Invention (28)

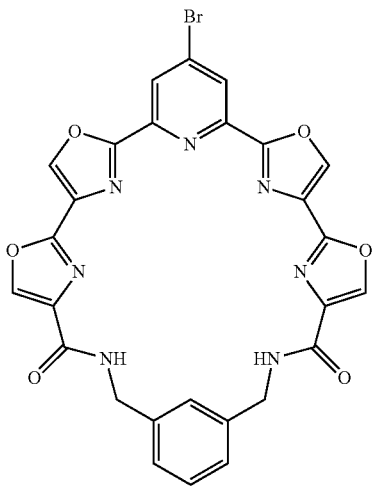

28

Compound 27 (43 mg, 0.1 mmol), EDC (77 mg, 0.4 mmol) and HOBT (54 mg, 0.4 mmol) were dissolved in anhydrous DMF (50 mL) and placed under argon. Then 2,6-lutidine (93 μL, 0.8 mmol) was added followed by a solution of m-xylenediamine (13 μL 0.1 mmol) in DMF (0.5 mL). The reaction stirred at room temperature for 2 days and then concentrated under vacuum. The resulting residue was washed with water and the white precipitate was filtered and collected. The solid was flash chromatographed on SiO₂ with 1-5% MeOH/CH₂Cl₂ to give the product as a white solid weighing 18 mg, 35%. Melting Point 211-213° C.; ¹H NMR (CDCl₃+CD₃OD) δ 8.37 (s, 2H), 8.32 (m, 2H), 8.26 (s, 2H), 7.36 (s, 3H), 4.61 (s, 4H); ¹³C NMR (CDCl₃+CD₃OD) δ 160.2, 159.7, 154.2, 146.1, 141.5, 139.8, 137.7, 137.4, 132.0, 130.2, 129.7, 129.4, 126.1, 108.0, 43.9; HRMS (ESI) m/z calcd for C₂₇H₁₇BrN₇O₆ (M+H): 614.0424; found: 614.0420.

The intermediate Compound 27 was prepared as follows.

a. Preparation of Compound 23

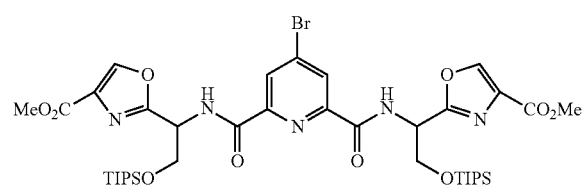

23

4-bromopyridine-2,6-dicarboxylic acid (112 mg, 0.46 mmol), methyl 2-(1-amino-2-(triisopropylsilyloxy)ethyl)oxazole-4-carboxylate (311 mg, 0.91 mmol), EDC (349 mg, 1.82 mmol) and HOBT (246 mg, 1.82 mmol) were dissolved in anhydrous DMF (30 mL) 2,6-Lutidine (211 μL, 1.82 mmol) was added and the reaction mixture was placed under argon before cooling to 0° C. The reaction mixture warmed to room temperature overnight and then the solvent was removed by Kugel-rhor distillation (50° C., 5 mmHg). The resulting residue was taken up in a mixture of ethyl acetate and water and the layers were separated. The organic layer was washed with water and brine. This was then dried with Na₂SO₄ and concentrated to a yellow oil weighing 410 mg, 100%. ¹H NMR (CDCl₃) δ 8.50 (m, 4H), 8.24 (s, 2H), 5.59 (dt, 2H, J=3, 6), 4.25 (d, 4H, J=6), 3.85 (s, 6H), 0.90 (m, 42H); ¹³C NMR (CDCl₃) δ 162.1, 161.5, 156.2, 148.6, 143.3, 135.3, 132.6, 128.3, 63.4, 51.2, 49.4, 16.9, 11.0; IR (thin film NaCl) 3299, 2944, 2866, 2129, 1743, 1674, 1655, 1582, 1526, 1464, 1441, 1383, 1343, 1322, 1259, 1200, 1114, 1069, 997, 920, 883, 847, 802, 737, 683, 660 cm$^{-1}$.

b. Preparation of Compound 24

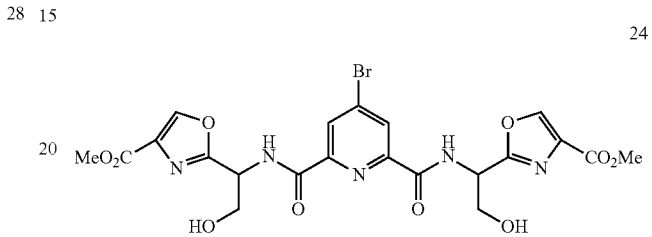

24

Compound 23 (410 mg, 0.46 mmol) was dissolved in a mixture of anhydrous THF (5 mL) and pyridine (0.4 mL) followed by the addition of HF-pyridine complex (0.3 mL) The reaction stirred under a drying tube overnight at room temperature. A saturated solution of NaHCO₃ was added and the resulting white precipitate was filtered and washed with water. The solid was collected and the aqueous filtrate was extracted with CH₂Cl₂. The organic solution was dried with Na₂SO₄ and concentrated in vacuo to a white solid. This was combined with the filtered solid to give 67 mg of Compound 24 as a white solid, 25%. Melting point 173-175° C. ¹H NMR (DMSO) δ 9.64 (d, 2H, J=8), 8.84 (s, 2H), 8.37 (s, 2H), 5.28 (m, 2H), 4.05 (m, 4H), 3.79 (s, 6H).

c. Preparation of Compound 25

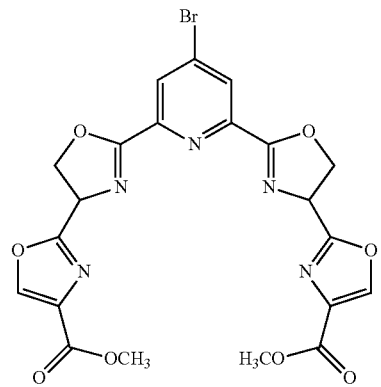

25

Compound 24 (67 mg, 0.11 mmol) was suspended in anhydrous CH₂Cl₂ (10 mL) and placed under argon. After cooling to −78° C., DAST (0.38 μL, 0.3 mmol) was added and the reaction stirred for 4 hours at low temperature. Then K₂CO₃ (41 mg, 0.3 mmol) was added and the reaction mixture warmed to room temperature. This was poured into a solution of saturated NaHCO₃ and extracted with CH₂Cl₂. The combined organic extracts were dried with Na₂SO₄ and concentrated to give Compound 25 as a white solid weighing 50 mg, 79%.

¹H NMR (CDCl₃) δ 8.43 (s, 2H), 8.27 (s, 2H), 5.65 (t, 2H, J=8), 4.94 (m, 4H), 3.92 (s, 6H) ¹³C NMR (CDCl₃) δ 163.3, 161.8, 160.4, 146.1, 144.0, 133.3, 132.7, 129.1, 70.7, 63.1, 51.4 IR (thin film NaCl) 3156, 2954, 2246, 1740, 1638, 1583, 1562, 1437, 1383, 1344, 1321, 1271, 1234, 1203, 1144, 1112, 994, 917, 805, 732 cm$^{-1}$.

d. Preparation of Compound 26

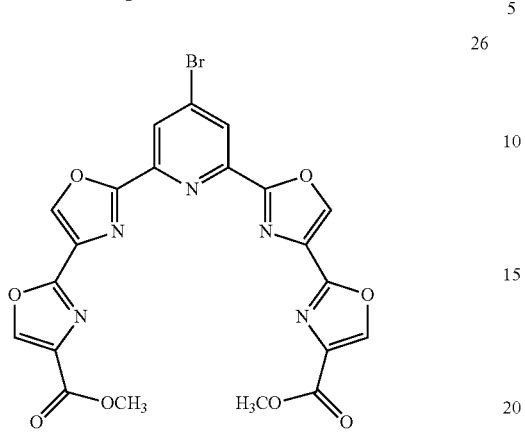

26

Compound 25 (50 mg, 0.09 mmol) was suspended in anhydrous CH$_3$CN (10 mL) and placed under argon. This was cooled to 0° C. and treated dropwise with DBU (0.54 μL, 0.36 mmol) and BrCCl$_3$ (43 μL, 0.44 mmol). The reaction warmed to room temperature overnight and a white precipitate formed. This was filtered and washed with CH$_3$CN to give Compound 26 as a white solid weighing 25 mg, 50%. Melting point 280-282° C. (decomposed); $^1$H NMR (CDCl$_3$) δ 8.63 (s, 2H), 8.60 (s, 2H), 8.37 (s, 2H), 3.83 (s, 6H); IR (thin film NaCl) 3426, 3140, 3109, 3064, 3014, 2959, 2359, 2334, 1729, 1637, 1581, 1563, 1543, 1519, 1443, 1425, 1340, 1319, 1259, 1199, 1160, 1115, 1002, 972, 938, 918, 877, 797, 765, 733, 709 cm$^{-1}$.

e. Preparation of Compound 27

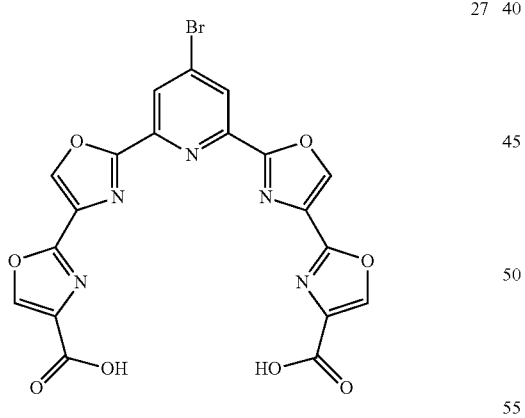

27

Compound 26 (25 mg, 0.046 mmol) and LiBr (20 mg, 0.23 mmol) were suspended in a mixture of THF (10 mL) and water (0.5 mL) The reaction mixture was placed under argon and DBU (14 μL, 0.09 mmol) was added. This stirred at room temperature overnight and then refluxed for 3 days. The reaction mixture was cooled to room temperature and concentrated in vacuo. The resulting solid was suspended in water and filtered. This gave compound 27 10 mg of product as a white solid, 43%. IR (thin film NaCl) 1727, 1693, 1655, 1567, 1523, 1438, 1323, 1237, 1153, 1118, 1062, 1003, 921, 762, 732, 707 cm$^{-1}$.

Example 7

Preparation of Representative Compound of the Invention (29)

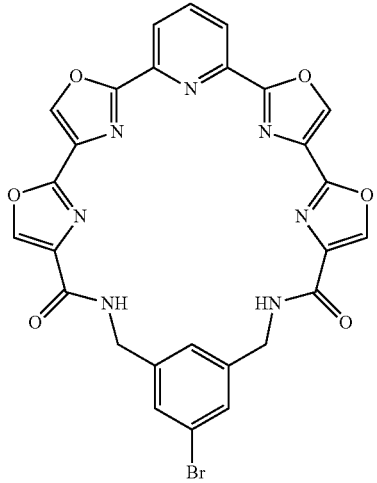

29

Compound 5 (43 mg, 0.1 mmol), EDC (77 mg, 0.4 mmol) and HOBT (54 mg, 0.4 mmol) were dissolved in anhydrous DMF (50 mL) and placed under argon. Then 2,6-lutidine (93 μL, 0.8 mmol) was added followed by a solution of (5-bromo-1,3-phenylene)dimethanamine (21 mg 0.1 mmol) in DMF (2 mL). The reaction stirred at room temperature for 2 days and then concentrated under vacuum. The resulting residue was washed with water and the white precipitate was filtered and collected. The solid was flash chromatographed on SiO$_2$ with 1-5% MeOH/CH$_2$Cl$_2$ to give compound 29 as a white solid (26 mg, 43%). Melting Point 248-250° C.; $^1$H NMR (CDCl$_3$) δ 8.28 (s, 2H), 8.25 (s, 2H), 8.08 (m, 3H), 7.51 (m, 3H), 7.29 (m, 2H), 4.56 (d, 4H, J=5); $^{13}$C NMR (CDCl$_3$) δ 159.9, 159.3, 153.0, 144.3, 140.1, 138.5, 138.0, 136.7, 136.6, 130.7, 128.3, 126.0, 122.5, 42.9; HRMS (ESI) m/z calcd for C$_{27}$H$_{17}$BrN$_7$O$_6$ (M+H): 614.0418; found: 614.0418.

Example 8

Preparation of Representative Compound of the Invention (30)

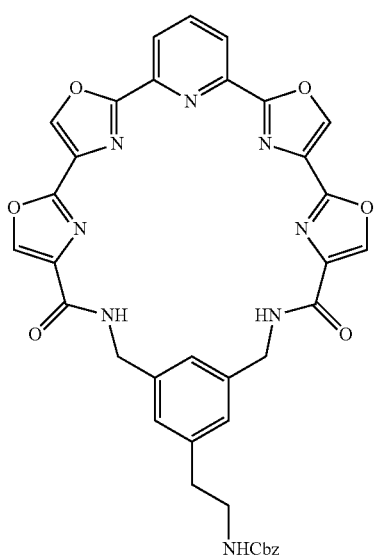

30

Compound 5 (50 mg, 0.11 mmol), EDC (87 mg, 0.44 mmol), HOBT (59 mg, 0.44 mmol) and benzyl 3,5-bis(aminomethyl)phenethylcarbamate (36 mg, 0.11 mmol) were dissolved in anhydrous DMF (35 mL) Then 2,6-lutidine (102 µL, 0.88 mmol) was added and the reaction was placed under argon. The reaction stirred at room temperature for 1.5 days and then concentrated under vacuum. The resulting residue was washed with water and the white precipitate was filtered and collected. The solid was flash chromatographed on $SiO_2$ with 1-5% $MeOH/CH_2Cl_2$ to give Compound 30 as a white solid (33 mg, 42%). Melting Point 196-198° C.; $^1H$ NMR ($CDCl_3+CD_3OD$) δ 8.41 (d, 2H, J=), 8.34 (s, 2H), 8.32 (s, 2H), 8.10 (s, 3H), 7.42 (s, 1H), 7.30 (m, 5H), 7.18 (s, 2H), 5.37 (s, 1H), 5.04 (s, 2H), 4.59 (d, 4H, J=) 3.41 (m, 4H); $^{13}C$ NMR ($CDCl_3+CD_3OD$) δ 160.9, 160.4, 156.8, 156.7, 154.3, 145.1, 141.5, 140.4, 139.5, 139.0, 138.1, 137.6, 136.8, 131.7, 129.6, 128.5, 128.2, 128.0, 127.9, 122.9, 66.6, 42.2, 35.9; HRMS (ESI) m/z calcd for $C_{37}H_{29}N_8O_8$ (M+H): 713.2108; found: 713.2091.

Example 9

Preparation of Representative Compound of the Invention (31)

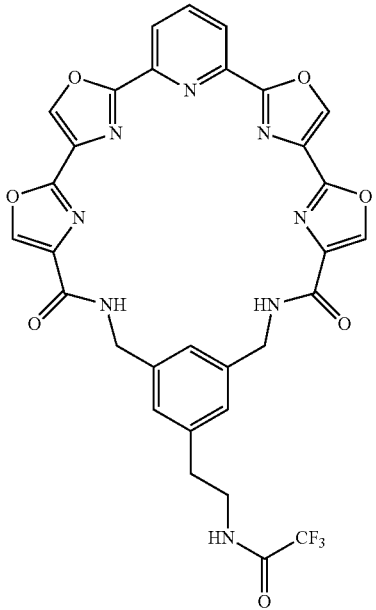

31

Compound 5 (44 mg, 0.10 mmol), EDC (78 mg, 0.40 mmol), and HOBT (55 mg, 0.40 mmol) were dissolved in anhydrous DMF (40 mL). The reaction was placed under argon and 2,6-lutidine (116 µL, 1.0 mmol) was added. Then a solution of N-(3,5-Bis(aminomethyl)phenethyl-2,2,2-trifluoroacetamide (51 mg, 0.10 mmol) in DMF (10 mL) was added dropwise. The reaction stirred at room temperature for 1.5 days and then concentrated under vacuum. The resulting residue was washed with water and the white precipitate was filtered and collected. The solid was flash chromatographed on $SiO_2$ with 1-5% $MeOH/CH_2Cl_2$ to give Compound 31 as a white solid (21 mg, 31%). Melting Point 290° C. (dec.); $^1H$ NMR ($CDCl_3+CD_3OD$) δ 8.38 (s, 2H), 8.37 (s, 2H), 8.12 (s, 2H) 7.60 (s, 1H), 7.47 (s, 1H), 7.19 (s, 2H), 4.60 (s, 4H), 4.07 (m, 2H), 3.40 (m, 2H); $^{13}C$ NMR ($CDCl_3+CD_3OD$) δ 160.9, 154.1, 145.0, 141.6, 140.0, 139.5, 138.2, 137.6, 131.6, 130.0, 128.6, 122.9, 43.7, 38.8, 34.1; HRMS (ESI) m/z calcd for $C_{31}H_{22}F_3N_8O_7$ (M+H): 675.1564; found: 675.1546.

Example 10

Preparation of Representative Compound of the Invention (32)

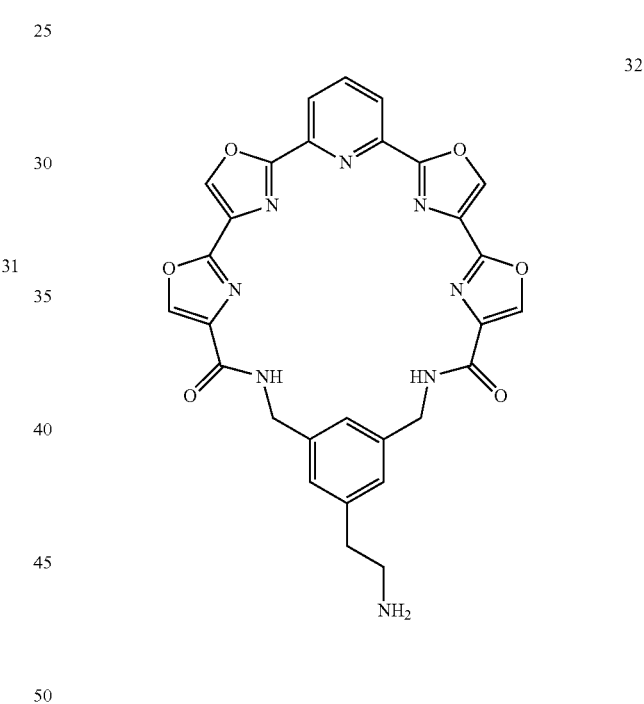

32

A suspension of Compound 31 (15 mg, 0.02 mmol) and $K_2CO_3$ (17 mg, 0.12 mmol) in MeOH (10 mL) was heated at reflux for 4.75 h. After cooling to room temperature solvent was removed under reduced pressure and the residue was partitioned between water and $CH_2Cl_2$. The organic layer was separated and dried over $Na_2SO_4$, filtered, and evaporated to give Compound 32 as a white solid (0.5 mg, 81% yield); Melting Point 277-280° C. (dec.); $^1H$ NMR ($CDCl_3+CD_3OD$) δ 8.42 (s, 2H), 8.40 (s, 2H), 8.13 (s, 3H), 7.45 (s, 1H), 7.19 (s, 2H), 4.60 (s, 4H) 2.92 (m, 2H), 2.75 (m, 2H); $^{13}C$ NMR ($CDCl_3+CD_3OD$) δ 161.0, 160.5, 154.4, 145.1, 141.7, 140.9, 139.7, 139.2, 138.1, 137.6, 131.7, 129.5, 129.2, 128.9, 123.0, 43.8, 43.0, 39.4; HRMS (ESI) m/z calcd for $C_{29}H_{23}N_8O_6$ (M+H): 579.1741; found: 579.1723.

Example 11

Preparation of Representative Compound of the Invention (33)

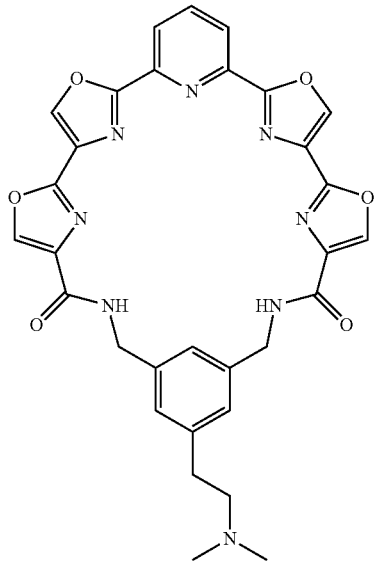

Compound 32 (6 mg, 0.01 mmol) was dissolved in 1:4 MeOH/CH$_2$Cl$_2$ (5 mL) and placed under argon. A solution of 37% aqueous formaldehyde (0.25 mL) was added the reaction mixture was allowed to stir at room temperature for 10 min. At that point sodium triacetoxyborohydride (15 mg, 0.07 mmol) was added and stirring continued for 16 h. The reaction was not complete by TLC and additional formaldehyde solution (0.25 mL) and NaBH(OAc)$_3$ (15 mg) was added. After 6 h TLC showed the reaction to be complete and it was poured into saturated NaHCO$_3$ and extracted with CH$_2$Cl$_2$. After concentrating, flash chromatography (1-15% MeOH/CH$_2$Cl$_2$ afforded Compound 33 as a white solid (6 mg, 100% yield); Melting Point 295° C. (dec.); $^1$H NMR (CDCl$_3$+CD$_3$OD) δ 8.34 (s, 2H), 8.33 (s, 2H), 8.10 (s, 3H), 7.41 (s, 1H), 7.19 (s, 2H), 4.59 (s, 4H), 2.79 (m, 2H), 2.61 (m, 2H) 2.30 (s, 6H) $^{13}$C NMR (CDCl$_3$+CD$_3$OD) δ 160.8, 160.3, 154.2, 145.1, 141.5, 139.4, 139.0, 137.9, 131.7, 129.4, 128.1, 122.8, 45.0, 43.8; HRMS (ESI) m/z calcd for C$_{31}$H$_{27}$N$_8$O$_6$ (M+H): 607.2054; found: 607.2029.

Example 12

Preparation of Representative Compound of the Invention (34)

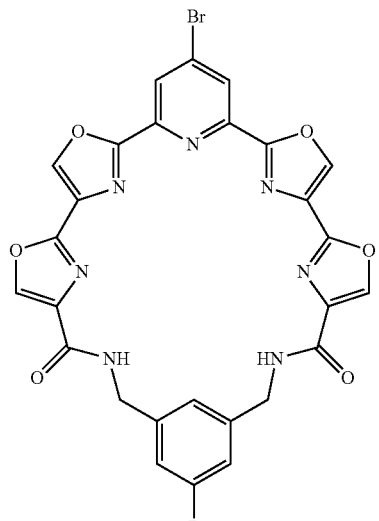

Compound 27 (17 mg, 0.033 mmol), EDC (26 mg, 0.13 mmol), HOBT (18 mg, 0.13 mmol) and (5-bromo-1,3-phenylene)dimethanamine (10 mg, 0.033 mmol) were dissolved in anhydrous DMF (15 mL) Then 2,6-lutidine (39 µL, 0.33 mmol) was added and the reaction was placed under argon. The reaction stirred at room temperature for 1.5 days and then concentrated under vacuum. The resulting residue was washed with water and the white precipitate was filtered and collected. The solid was flash chromatographed on SiO$_2$ with 1-5% MeOH/CH$_2$Cl$_2$ to give Compound 34 as a white solid (5 mg, 22%). Melting Point 250° C. (dec); $^1$H NMR (CDCl$_3$+CD$_3$OD) δ 8.28 (s, 2H), 8.22 (s, 2H), 8.15 (s, 2H), 7.39 (s, 3H), 4.46 (s, 4H); $^{13}$C NMR (CDCl$_3$+CD$_3$OD) δ 160.3, 159.6, 145.7, 141.6, 139.8, 139.7, 131.7, 131.6, 128.4, 125.9, 122.7, 43.0

Example 13

Preparation of Representative Compound of the Invention (35)

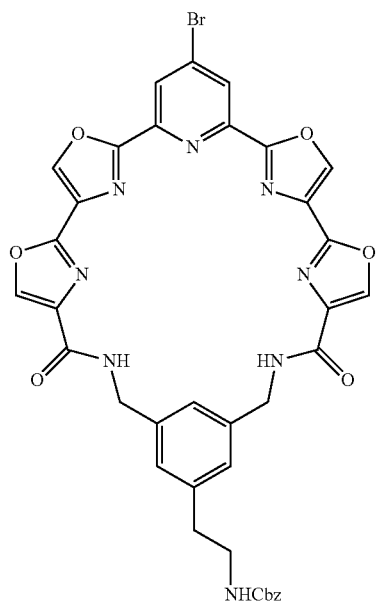

Compound 27 (20 mg, 0.039 mmol), EDC (31 mg, 0.16 mmol), HOBT (21 mg, 0.16 mmol) and benzyl 3,5-bis(aminomethyl)phenethylcarbamate (12 mg, 0.039 mmol) were dissolved in anhydrous DMF (20 mL). Then 2,6-lutidine (36 µL, 0.31 mmol) was added and the reaction was placed under argon. The reaction stirred at room temperature for 1.5 days and then concentrated under vacuum. The resulting residue was washed with water and the white precipitate was filtered and collected. The solid was flash chromatographed on $SiO_2$ with 1-5% $MeOH/CH_2Cl_2$ to give Compound 35 as a white solid (13 mg, 42%) Melting Point 204-205° C.; $^1$H NMR ($CDCl_3$) δ 8.24 (m, 5H), 7.65 (s, 2H), 7.56 (m, 2H), 7.3 (m, 5H), 7.17 (s, 2H), 5.06 (s, 2H), 4.91 (s, 1H), 4.56 (s, 2H), 3.44 (m, 2H), 2.80 (m, 2H); $^{13}$C NMR ($CDCl_3$) δ 159.6, 159.4, 159.4, 156.3, 154.0, 153.9, 147.6, 146.2, 140.8, 139.4, 138.1, 137.5, 136.7, 134.9, 132.1, 132.0, 130.0, 129.9, 128.5, 128.4, 128.3, 127.9, 127.7, 125.9, 125.9, 121.1, 108.2, 107.8, 66.5, 43.8, 42.2, 35.9; HRMS (ESI) m/z calcd for $C_{37}H_{28}BrN_8O_8$ (M+H): 791.1213; found: 791.1199.

Example 14

Preparation of Representative Compound of the Invention (36)

36

Compound 27 (33 mg, 0.064 mmol), EDC (51 mg, 0.26 mmol), and HOBT (35 mg, 0.260 mmol) were dissolved in anhydrous DMF (30 mL). The reaction was placed under argon and 2,6-lutidine (75 µL, 0.64 mmol) was added. Then a solution of N-(3,5-Bis(aminomethyl)phenethyl-2,2,2-trifluoroacetamide (32 mg, 0.064 mmol) in DMF (2 mL) was added dropwise. The reaction stirred at room temperature for 1.5 days and then concentrated under vacuum. The resulting residue was washed with water and the white precipitate was filtered and collected. The solid was flash chromatographed on $SiO_2$ with 1-5% $MeOH/CH_2Cl_2$ to give Compound 36 as a white solid (12 mg, 25%). Melting Point 305-307° C. (dec.); $^1$H NMR ($CDCl_3$+$CD_3OD$) δ 8.38 (s, 2H), 8.37 (s, 2H), 8.27 (s, 2H), 7.41 (s, 1H), 7.17 (s, 2H), 4.59 (s, 4H), 3.53 (m, 2H), 3.00 (m, 2H); $^{13}$C NMR δ 160.4, 159.7, 154.1, 141.6, 139.8, 137.6, 135.5, 131.9, 129.6, 43.7, 41.1, 34.7; HRMS (ESI) m/z calcd for $C_{31}H_{21}BrF_3N_8O_7$ (M+H): 753.0669; found: 753.0651.

Example 15

Preparation of Representative Compound of the Invention (43)

43

Compound 42 (50 mg, 0.078 mmol), EDC (62 mg, 0.33 mmol) and HOBT (42 mg, 0.33 mmol) were dissolved in anhydrous DMF (35 mL) and placed under argon. Then 2,6-lutidine (73 µL, 0.62 mmol) was added followed by a solution of m-xylenediamine (10 µL, 0.078 mmol) in DMF (0.5 mL) The reaction stirred at room temperature for 2 days and then concentrated under vacuum. The resulting residue was washed with water and the white precipitate was filtered and collected. The solid was flash chromatographed on $SiO_2$ with 1-5% $MeOH/CH_2Cl_2$ to give Compound 43 as a white solid (19 mg, 33%). Melting Point 249-252° C. (dec.); $^1$H NMR ($CDCl_3$) δ 8.24 (s, 2H), 8.23 (s, 2H), 7.85 (dd, 2H, J=3, 5), 7.72 (dd, 2H, J=3, 5), 7.49 (m, 4H), 7.37 (m, 4H), 4.59 (d, 4H, J=5), 4.27 (t, 2H, J=6), 3.97 (t, 2H, J=6), 2.30 (dt, 2H, J=6, 12); $^{13}$C NMR ($CDCl_3$) δ 168.4, 166.7, 160.5, 159.7, 154.3, 146.8, 140.5, 138.8, 137.8, 137.5, 134.1, 132.1, 131.9, 129.9, 129.9, 129.5, 123.4, 109.4, 66.7, 43.9, 35.1, 28.0 IR (thin film NaCl) 3401, 3147, 2926, 1770, 1711, 1667, 1593, 1553, 1511, 1447, 1397, 1367, 1312, 1260, 1214, 1166, 1109, 1036, 916, 796, 724 cm$^{-1}$; HRMS (ESI) m/z calcd for $C_{38}H_{27}N_8O_9$ (M+H): 739.1896; found: 739.1891.

The intermediate compound 42 was prepared as follows.

a. Preparation of Compound 37

37

Chelidamic acid (230 mg, 1.26 mmol), methyl 2-(1-amino-2-(triisopropylsilyloxy)ethyl)oxazole-4-carboxylate (860 mg, 2.51 mmol), EDC (966 mg, 5.04 mmol) and HOBT (681 mg, 5.04 mmol) were dissolved in anhydrous DMF (50 mL). 2,6-Lutidine (1.2 mL, 10.1 mmol) was added and the reaction mixture was placed under argon before cooling to 0° C. The reaction mixture warmed to room temperature overnight and then the solvent was removed by Kugel-rhor distillation (50° C., 5 mmHg). The resulting residue was taken up in a mixture of ethyl acetate and water and the layers were separated. The organic layer was washed with brine, 5% HCl, water and brine. This was then dried with $Na_2SO_4$ and concentrated to a yellow oil (900 mg, 86%). $^1$H NMR ($CDCl_3$) δ 10.62 (s, 1H), 8.70 (d, 2H, J=9), 8.25 (s, 2H), 7.82 (s, 2H), 5.57 (m, 2H), 4.24 (d, 4H, J=6), 3.90 (s, 6H), 0.96 (m, 42H) $^{13}$C NMR ($CDCl_3$) δ 165.9, 163.0, 162.0, 160.4, 149.2, 143.2, 132.4, 112.6, 63.5, 51.2, 49.2, 16.8, 10.9; IR (thin film NaCl) 3292, 3166, 2944, 2867, 2250, 1741, 1669, 1608, 1582, 1525, 1464, 1438, 1387, 1347, 1323, 1277, 1251, 1201, 1114, 1070, 998, 916, 883, 802, 733, 686, 664, 647 $cm^{-1}$; HRMS (ESI) m/z calcd for $C_{39}H_{62}N_5O_{11}Si_2$ (M+H): 832.3979; found: 832.3971.

b. Preparation of Compound 38

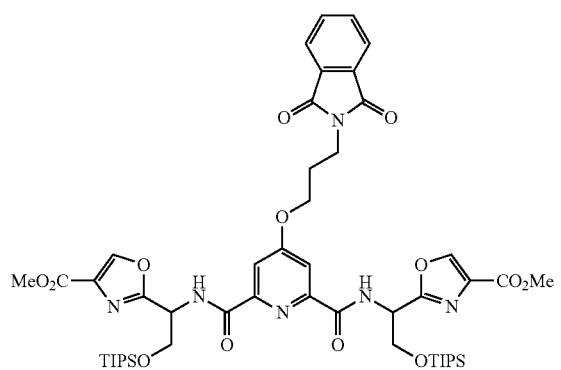

38

Compound 37 (642 mg, 0.77 mmol) and N-(3-bromopropyl)phthalimide (227 mg, 0.85 mmol) were dissolved in anhydrous DMF (10 mL) and placed under argon. Then DBU (127 μL 0.85 mmol) was added and the reaction was warmed to 60° C. for 6 hours. After cooling to room temperature, the reaction mixture was poured into water and extracted with ethyl acetate. The combined organic layers were washed with 5% HCl and brine. This was then dried with $Na_2SO_4$ and concentrated in vacuo to an oil that was flash chromatographed on $SiO_2$ with 1-4% $MeOH/CH_2Cl_2$. Compound 38 was isolated as a colorless oil weighing 727 mg, 92%. $^1$H NMR ($CDCl_3$) δ 8.61 (d, 2H, J=9), 8.24 (s, 2H), 7.84 (m, 2H), 7.73 (m, 4H), 5.59 (m, 2H), 4.23 (m, 6H), 3.93 (m, 8H), 2.25 (m, 2H), 1.03 (m, 42H); $^{13}$C NMR ($CDCl_3$) δ 167.4, 166.4, 162.5, 162.3, 160.5, 149.5, 143.3, 133.2, 132.6, 131.2, 122.5, 111.1, 65.7, 63.5, 51.2, 49.3, 34.2, 27.0, 16.9, 10.9; IR (thin film NaCl) 3330, 2944, 2866, 1715, 1683, 1583, 1522, 1466, 1439, 1395, 1344, 1201, 1114, 1000, 918, 882, 801, 723, 685 $cm^{-1}$; HRMS (ESI) m/z calcd for $C_{50}H_{71}N_6O_{13}Si_2$ (M+H): 1019.4612; found: 1019.4607 c. Preparation of Compound 39

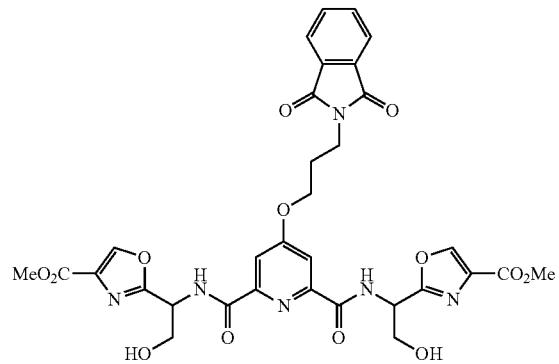

39

Compound 38 (1.05 mg, 1.03 mmol) was dissolved in a mixture of anhydrous THF (20 mL) and pyridine (1 mL) followed by the addition of HF-pyridine complex (0.5 mL). The reaction stirred under a drying tube overnight at room temperature. A saturated solution of $NaHCO_3$ was added and the resulting white precipitate was filtered and washed with water. The solid was collected and the aqueous filtrate was extracted with $CH_2Cl_2$. The organic solution was dried with $Na_2SO_4$ and concentrated in vacuo to a white solid. This was combined with the filtered solid to give 730 mg of Compound 39 as a white solid, 100%.

d. Preparation of Compound 40

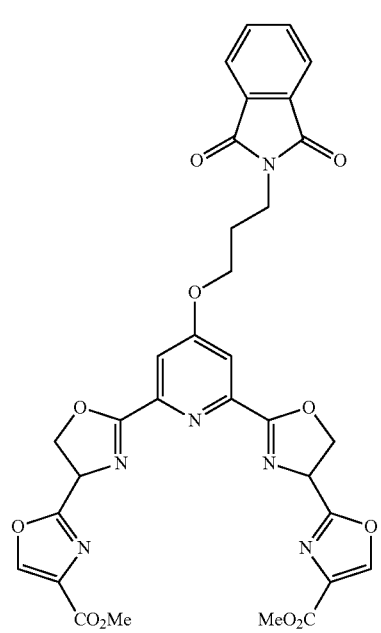

40

Compound 39 (730 mg, 1.03 mmol) was suspended in anhydrous $CH_2Cl_2$ (30 mL) and placed under argon. After cooling to −78° C., DAST (0.35 mL, 2.66 mmol) was added and the reaction stirred for 4 hours at low temperature. Then K$_2$CO$_3$ (367 mg, 2.66 mmol) was added and the reaction mixture warmed to room temperature. This was poured into a solution of saturated NaHCO$_3$ and extracted with CH$_2$Cl$_2$. The combined organic extracts were dried with Na$_2$SO$_4$ and concentrated to give Compound 40 as a white solid weighing 690 mg, 100%. $^1$H NMR (CDCl$_3$) δ 8.26 (s, 2H), 7.82 (m, 2H), 7.72 (m, 2H), 7.64 (s, 2H), 5.62 (dd, 2H, J=9, 11), 4.90 (m, 4H), 4.17 (t, 2H, J=6), 3.92, (m, 8H), 2.25 (m, 2H); $^{13}$C NMR (CDCl$_3$) δ 167.4, 165.0, 164.3, 162.1, 160.5, 146.7, 144.0, 133.2, 132.6, 131.1, 122.5, 112.3, 70.4, 65.6, 63.1, 51.4, 34.1, 27.0; IR (thin film NaCl) 3162, 3096, 2953, 2247, 1771, 1740, 1712, 1639, 1587, 1519, 1437, 1394, 1344, 1322, 1272, 1203, 1145, 1112, 1036, 993, 915, 804, 771, 724 cm$^{-1}$ HRMS (ESI) m/z calcd for C$_{32}$H$_{27}$N$_6$O$_{11}$ (M+H): 671.1732; found: 671.1733 e. Preparation of Compound 41

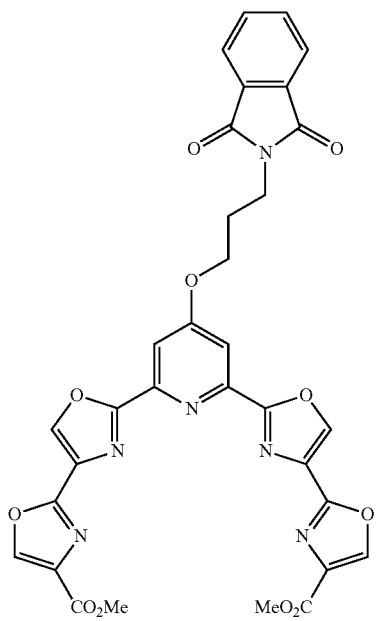

41

Compound 40 (637 mg, 1.0 mmol) was suspended in anhydrous CH$_3$CN (20 mL) and placed under argon. This was cooled to 0° C. and treated dropwise with DBU (0.6 mL, 4.0 mmol) and BrCCl$_3$ (0.5 mL, 4.80 mmol). The reaction warmed to room temperature overnight and a white precipitate formed. This was filtered and washed with CH$_3$CN to give Compound 41 as a white solid (470 mg, 68%). Melting Point 147-150° C.; $^1$H NMR (DMSO) δ 9.16 (s, 2H), 9.02 (s, 2H), 7.82 (m, 4H), 7.61 (s, 2H), 4.37 (t, 2H, J=6), 3.81 (t, 2H, J=6), 2.14 (m, 2H); HRMS (ESI) m/z calcd for C$_{32}$H$_{23}$N$_6$O$_{11}$ (M+H): 667.1419; found: 667.1418 f. Preparation of Compound 42

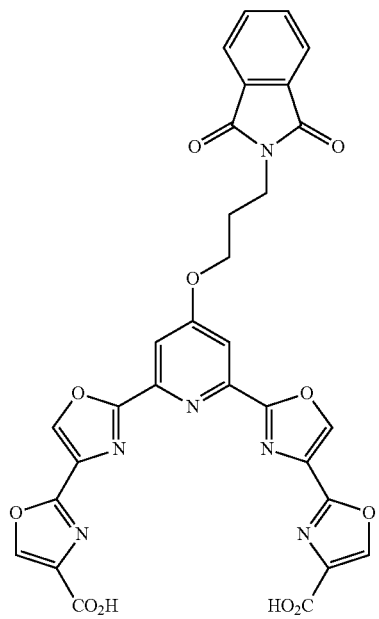

42

Compound 41 (150 mg, 0.23 mmol) and lithium chloride (95 mg, 2.3 mmol) were dissolved in wet DMF (5 mL) and placed under argon. This was refluxed overnight followed by concentration of the solvent in vacuo. The resulting residue was treated with 1N HCl and a white solid precipitated and was filtered. Compound 42 was isolated as a white solid (144 mg, 100%). Melting Point 147-150° C.; $^1$H NMR (DMSO) δ 9.14 (s, 2H) 8.90 (s, 2H), 7.82 (m, 4H), 7.62 (s, 2H), 4.37 (t, 2H, J=6), 3.81 (t, 2H, J=6), 2.14 (m, 2H); HRMS (ESI) m/z calcd for C$_{30}$H$_{19}$N$_6$O$_{11}$ (M+H): 639.1106; found: 639.1104.

Example 16

Preparation of Representative Compound of the Invention (44)

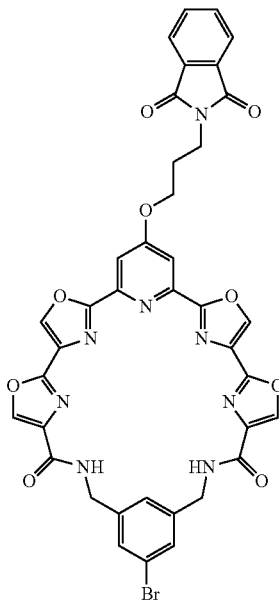

44

Compound 42 (22 mg, 0.034 mmol), EDC (26 mg, 0.13 mmol), HOBT (19 mg, 0.14 mmol) and (5-bromo-1,3-phenylene)dimethanamine (10 mg, 0.033 mmol) were dissolved in anhydrous DMF (15 mL). Then 2,6-lutidine (40 μL, 0.34 mmol) was added and the reaction was placed under argon. The reaction stirred at room temperature for 1.5 days and then concentrated under vacuum. The resulting residue was washed with water and the white precipitate was filtered and collected. The solid was flash chromatographed on $SiO_2$ with 1-5% $MeOH/CH_2Cl_2$ to give Compound 44 as a white solid (8 mg, 30%). Melting Point 289-290° C. (dec.); $^1$H NMR ($CDCl_3+CD_3OD$) δ 8.33 (s, 4H), 7.86 (dd, 2H, J=3, 5), 7.75 (dd, 2H, J=3, 5), 7.51 (m, 5H), 4.58 (s, 4H), 4.29 (t, 2H, J=6), 3.98 (t, 2H, J=7), 2.31 (dt, 2H, J=6, 12) $^{13}$C NMR ($CDCl_3+CD_3OD$) δ 168.6, 167.2, 160.9, 160.5, 154.3, 146.4, 141.6, 139.9, 139.3, 137.5, 134.4, 132.1, 131.9, 131.6, 128.7, 123.5, 122.8, 109.5, 66.9, 43.2, 35.1, 28.0 IR (thin film NaCl) 3390, 3144, 3056, 1768, 1705, 1672, 1593, 1554, 1516, 1432, 1405, 1365, 1308, 1165, 1112, 1062, 931, 916, 856, 787, 712 cm$^{-1}$; HRMS (ESI) m/z calcd for $C_{38}H_{26}BrN_8O_9$ (M+H): 817.1006; found: 817.0986.

Example 17

Preparation of Representative Compound of the Invention (45)

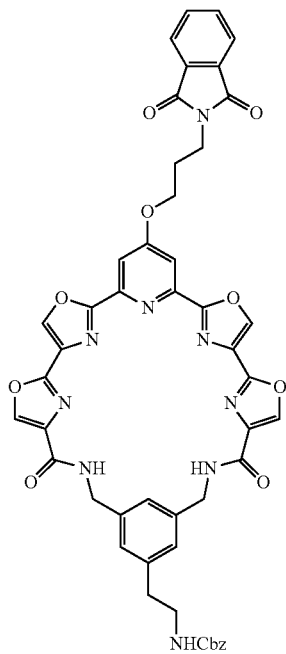

45

Compound 42 (21 mg, 0.033 mmol), EDC (34 mg, 0.19 mmol), HOBT (26 mg, 0.19 mmol) and benzyl 3,5-bis(aminomethyl)phenethylcarbamate (15 mg, 0.033 mmol) were dissolved in anhydrous DMF (25 mL) Then 2,6-lutidine (45 μL, 0.38 mmol) was added and the reaction was placed under argon. The reaction stirred at room temperature for 1.5 days and then concentrated under vacuum. The resulting residue was washed with water and the white precipitate was filtered and collected. The solid was flash chromatographed on $SiO_2$ with 1-5% $MeOH/CH_2Cl_2$ to give Compound 45 as a white solid (11 mg, 40%). Melting Point 167-170° C.; $^1$H NMR ($CDCl_3$) δ 8.24 (s, 2H), 8.23 (s, 2H), 7.85 (dd, 2H, J=3.5), 7.72 (dd, 2H, J=3.5), 7.56 (m, 2H), 7.47 (s, 2H), 7.27 (m, 5H), 7.17 (s, 3H), 5.04 (s, 2H), 4.95 (m, 1H), 4.56 (d, 4H, J=6), 4.27 (t, 2H, J=6), 3.97 (t, 2H, J=6), 3.45 (m, 2H), 2.81 (m, 2H), 2.32 (dt, 2H, J=6, 12); $^{13}$C NMR ($CDCl_3$) δ 168.4, 166.8, 160.5, 159.7, 156.3, 154.2, 146.7, 140.6, 138.8, 138.1, 137.4, 134.1, 132.1, 131.8, 130.0, 129.1, 128.4, 128.3, 128.2, 127.9, 125.3, 123.4, 109.4, 66.7, 43.8, 35.0, 28.0; HRMS (ESI) m/z calcd for $C_{48}H_{38}N_9O_{11}$ (M+H): 916.2691; found: 916.2669.

Example 18

Preparation of Representative Compound of the Invention (46)

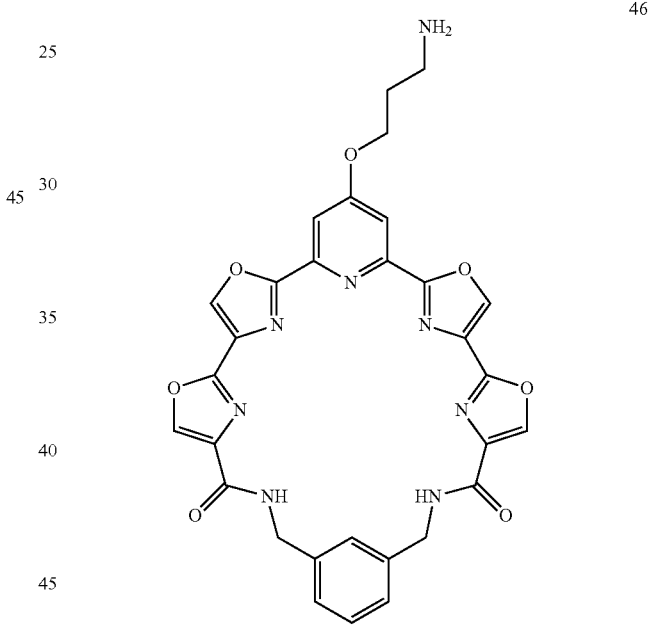

46

Compound 45 (24 mg, 0.033 mmol) was dissolved in ethanol (10 mL) and hydrazine monohydrate (0.5 mL) was added. This was refluxed for 3 hours and the solvent was then removed in vacuo. The resulting residue was taken up in dichloromethane and washed with 10% NaOH. The organic layer was dried with $Na_2SO_4$ and concentrated to give Compound 46 as a white solid (20 mg, 100%). Melting Point 237-239° C. (dec.); $^1$H NMR ($CDCl_3+CD_3OD$) δ 8.32 (m, 4H), 7.57 (s, 3H), 7.36 (m, 3H), 4.63 (s, 4H), 4.27 (m, 2H), 2.94 (t, 2H J=), 2.04 (dt, 2H, J=); $^{13}$C NMR ($CDCl_3+CD_3OD$) δ 167.4, 160.9, 160.3, 154.3, 146.4, 141.4, 139.4, 137.8, 137.5, 131.6, 130.2, 129.5, 129.2, 109.6, 66.7, 43.8, 38.4, 32.0; IR (thin film NaCl) 3378, 3129, 3096, 2926, 1646, 1588, 1557, 1521, 1445, 1316, 1261, 1099, 917, 796 cm$^{-1}$; HRMS (ESI) m/z calcd for $C_{30}H_{25}N_8O_7$ (M+H): 609.1846; found: 609.1825.

Example 19

Preparation of Representative Compound of the Invention (47)

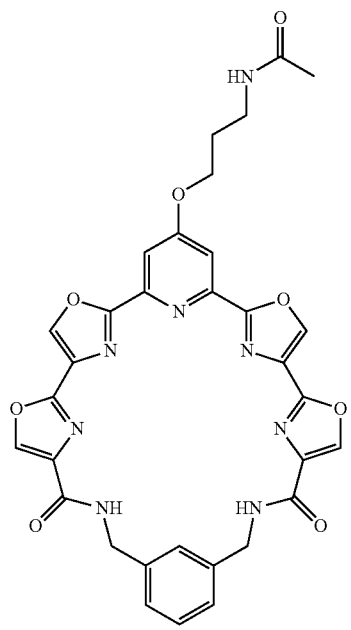

47

Compound 46 (15 mg, 0.25 mmol) was treated with a mixture of acetic anhydride (2 mL) and pyridine (2 mL) and stirred at room temperature overnight. The solvent was removed in vacuo and the resulting residue was washed with methanol. A white solid precipitated and was filtered to provide Compound 47 (9 mg, 56%). $^1$H NMR (DMSO) δ 9.22 (s, 2H), 9.00 (s, 2H), 8.44 (t, 1H), 7.76 (s, 2H), 7.40 (m, 4H), 4.54 (s, 4H), 4.39 (t, 2H, J=), 3.30 (m, 2H), 2.39 (s, 6H), 1.99 (m, 2H).

Example 20

Preparation of Representative Compound of the Invention (48)

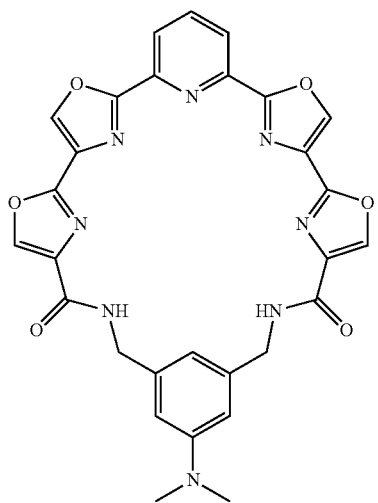

48

Compound 5 (68 mg, 0.156 mmol), EDC (120 mg, 0.63 mmol), and HOBT (85 mg, 0.63 mmol) were suspended in anhydrous DMF (60 mL) The reaction was placed under argon and 2,6-lutidine (182 μL, 1.56 mmol) was added. Then a solution of (5-(dimethylamino)-1,3-phenylene)dimethanamine (28 mg, 0.156 mmol) in DMF (10 mL) was added dropwise. The reaction stirred at room temperature for 2 days and then concentrated in vacuo. The resulting residue was washed with water and the white precipitate was filtered and collected. The solid was flash chromatographed on SiO$_2$ with 1-2.5% MeOH/CH$_2$Cl$_2$ to give the product as a white solid weighing 9 mg, 10%. $^1$H NMR (CDCl$_3$) δ 8.32 (m, 6H), 8.10 (m, 3H), 6.90 (s, 1H), 6.71 (s, 2H), 4.56 (s, 4H), 2.93 (s, 6H); $^{13}$C NMR (CDCl$_3$) δ 160.8, 160.3, 154.3, 151.7, 145.2, 141.4, 139.4, 138.9, 138.4, 137.7, 131.8, 122.8, 118.3, 113.3, 44.0, 40.6; IR (thin film, NaCl) 3417, 1644, 1605, 1439, 1370, 1172, 1112, 926 cm$^{-1}$.

Example 21

Preparation of Representative Compound of the Invention (53)

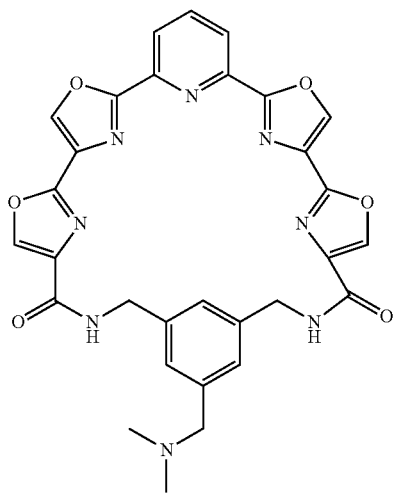

53

Compound 5 (87 mg, 0.2 mmol) and manganese (II) sulfate monohydrate (169 mg, 1 mmol) were suspended in anhydrous DMF (90 mL) and placed under argon. This was heated to 65° C. for 15 minutes and then cooled for 10 minutes. Then EDC (158 mg, 0.8 mmol), and HOBT (108 mg, 0.8 mmol) and 2,6-lutidine (186 μL, 1.6 mmol) was added. Then a solution of (5-((dimethylamino)methyl)-1,3-phenylene)dimethanamine (39 mg, 0.2 mmol) in DMF (5 mL) was added dropwise. The reaction stirred at room temperature for 2 days and then concentrated in vacuo. The resulting residue was washed with water and the white precipitate was filtered and collected. The solid was flash chromatographed on SiO$_2$ with 1-5% MeOH/CH$_2$Cl$_2$ to give the product as a white solid weighing 5 mg, 4%. $^1$H NMR (CDCl$_3$) δ 8.58 (s, 2H), 8.44 (m, 4H), 8.63 (s, 2H), 8.07 (m, 2H), 3.97 (m, 6H), 3.46 (s, 3H), 3.12 (s, 3H).

The intermediate compound 52 was prepared as follows.

a. Preparation of Compound 49.

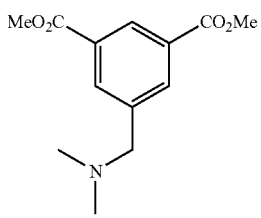

49

Dimethyl 5-(bromomethyl)isophthalate (890 mg, 3.11 mmol) was dissolved in anhydrous THF (15 mL) and treated with a solution of dimethylamine (10 mL, 20 mmol, 2M in THF). This stirred at room temperature for 30 minutes during which a white solid precipitated. The mixture was poured into 1N NaOH and extracted with ethyl acetate. The combined organic layers were washed with brine and dried with $Na_2SO_4$. Concentration in vacuo gave the product as a yellow oil weighing 761 mg, 97%. $^1$H NMR ($CDCl_3$) δ 8.59 (s, 1H), 8.19 (s, 2H), 3.95 (s, 6H), 3.51 (s, 2H), 2.26 (s, 6H); $^{13}$C NMR ($CDCl_3$) δ 166.3, 140.2, 134.4, 134.3, 130.7, 129.6, 128.8, 63.5, 52.3, 45.4; IR (thin film, NaCl) 3434, 2951, 2856, 2820, 2776, 2256, 1728, 1640, 1606, 1456, 1435, 1366, 1329, 1244, 1205, 1148, 1122, 1107, 1043, 1008, 913, 873, 842, 790, 755, 733, 647 $cm^{-1}$ b. Preparation of Compound 50

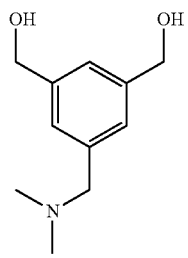

50

Dimethyl 5-((dimethylamino)methyl)isophthalate (760 mg, 2.96 mmol) was dissolved in THF (30 mL) and cooled to 0° C. To this solution was added lithium borohydride (390 mg, 17.7 mmol) and ethanol (5 mL). The reaction stirred and warmed to room temperature overnight. The mixture was poured into water and extracted with ethyl acetate. The combined organic layers were washed with brine and dried with $Na_2SO_4$. Concentration in vacuo resulted in a yellow oil that was flash chromatographed on $SiO_2$ with 1-20% methanol in $CH_2Cl_2$. The product was isolated as a white solid weighing 222 mg, 38%. $^1$H NMR ($CDCl_3$) δ 7.42 (s, 1H), 7.27 (s, 2H), 4.75 (s, 4H), 3.99 (s, 2H), 2.53 (s, 6H); $^{13}$C NMR ($CDCl_3$) δ 141.6, 132.0, 129.9, 126.0, 67.5, 64.8, 50.0; IR (thin film, NaCl) 3396, 3004, 2950, 2370, 2271, 1644, 1525, 1468, 1368, 1168, 1018, 873, 847, 821 $cm^{-1}$.

c. Preparation of Compound 51

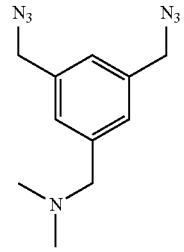

51

(5-((Dimethylamino)methyl)-1,3-phenylene)dimethanol (222 mg, 1.14 mmol) was dissolved in anhydrous THF (5 mL) and placed under argon. The solution was cooled to 0° C. and treated dropwise with both DBU (0.7 mL, 4.55 mmol) and DPPA (1 mL, 4.55 mmol). This stirred at 0° C. for 4 hours and a white solid precipitated and then warmed to room temperature overnight. The resulting clear yellow solution was poured into brine and extracted with ethyl acetate. The combined organic layers were dried with $Na_2SO_4$ and concentrated in vacuo to give a yellow oil. This was flash chromatographed on $SiO_2$ with 10-30% ethyl acetate in hexane to isolate the product as a colorless oil weighing 200 mg, 72%. $^1$H NMR ($CDCl_3$) δ 7.30 (m, 3H), 4.43 (s, 4H), 4.01 (s, 2H), 2.56 (s, 6H); $^{13}$C NMR ($CDCl_3$) δ 136.6, 132.7, 131.7, 125.6, 67.1, 54.1, 50.1; IR (thin film, NaCl) 2950, 2372, 2272, 2097, 1693, 1464, 1345, 1246, 1169, 1017, 842, 819 $cm^{-1}$.

d. Preparation of Compound 52

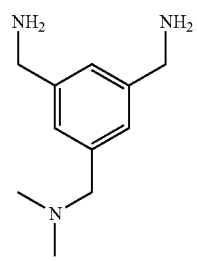

52

1-(3,5-Bis(azidomethyl)phenyl)-N,N-dimethylmethanamine was dissolved in a mixture of THF (10 mL) and water (1 mL) and polymer supported triphenylphosphine (333 mg, 1 mmol, ~3 mmol/g) was added. The reaction stirred at room temperature for 18 hours but TLC showed it was not complete. Additional polymer supported triphenylphosphine (100 mg, 0.3 mmol) and water (1 mL) were added. After stirring for an additional 24 hours the resin was filtered and washed with ethyl acetate. The filtrate was dried with $Na_2SO_4$ and concentrated in vacuo to give the product as a colorless oil weighing 77 mg, 100%. $^1$H NMR ($CDCl_3$) δ 7.37 (s, 1H), 7.22 (s, 2H), 3.82 (m, 6H), 2.49 (s, 6H); $^{13}$C NMR ($CDCl_3$) δ 143.6, 130.6, 129.8, 120.1, 67.4, 66.2, 49.7; IR (thin film, NaCl) 3314, 2945, 2369, 2318, 2271, 1666, 1605, 1467, 1169, 1017, 819 $cm^{-1}$.

Example 22

Preparation of Representative Compound of the Invention (59)

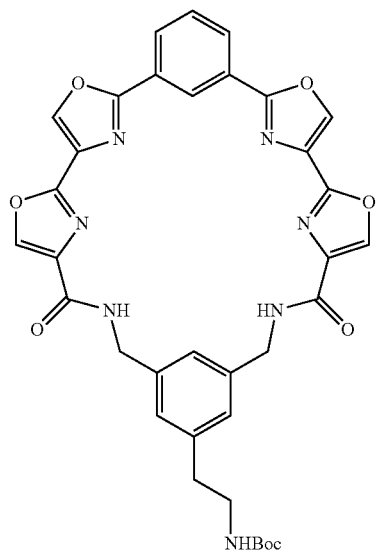

59

Compound 58 (60 mg, 0.138 mmol), EDC (106 mg, 0.53 mmol), and HOBT (75 mg, 0.53 mmol) were dissolved in anhydrous DMF (60 mL). The reaction was placed under argon and 2,6-lutidine (161 μL, 1.38 mmol) was added. Then a solution of tert-butyl 3,5-bis(aminomethyl)phenethylcarbamate (38 mg, 0.138 mmol) in DMF (8 mL) was added dropwise. The reaction stirred at room temperature for 1.5 days and then concentrated in vacuo. The resulting residue was washed with water and the white precipitate was filtered and collected. The solid was flash chromatographed on $SiO_2$ with 0.5-4% $MeOH/CH_2Cl_2$ to give the product as a white solid weighing 18 mg, 19%. $^1H$ NMR ($CDCl_3$) δ 9.43 (s, 1H), 8.32 (s, 2H), 8.26 (s, 2H), 8.04 (d, 2H, J=8), 7.62 (m, 2H), 7.30 (m, 2H), 7.20 (s, 2H), 4.90 (br s, 1H), 4.59 (d, 4H, J=8), 3.35 (m, 2H), 2.79 (m, 2H), 1.42 (s, 9H); $^{13}C$ NMR ($CDCl_3$) δ 162.0, 159.9, 159.8, 156.1, 155.0, 141.2, 138.7, 137.8, 137.1, 137.1, 131.0, 130.3, 129.6, 128.7, 128.4, 127.6, 127.4, 127.1, 79.3, 44.0, 43.9, 35.9, 28.4; IR (thin film, NaCl) 3390, 3164, 3117, 3043, 2977, 2932, 2494, 1702, 1660, 1592, 1503, 1458, 1428, 1366, 1347, 1316, 1290, 1253, 1172, 1104, 1066, 982, 941, 918, 836, 807, 777, 765, 723, 712, 686 $cm^{-1}$.

The intermediate compound 59 was prepared as follows.

a. Preparation of Compound 54

54

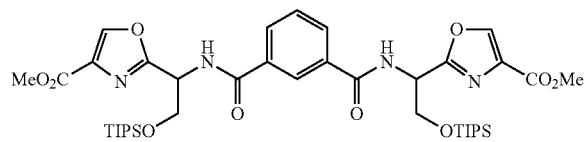

Isophthalic acid (364 mg, 2.2 mmol), methyl 2-(1-amino-2-(triisopropylsilyloxy)ethyl)oxazole-4-carboxylate (1.5 g, 4.4 mmol), EDC (1.69 g, 8.8 mmol) and HOBT (1.19 g, 8.8 mmol) were dissolved in anhydrous DMF (50 mL) 2,6-Lutidine (2.6 mL, 22 mmol) was added and the reaction mixture was placed under argon. The reaction mixture stirred at room temperature overnight and then the solvent was removed in vacuo. The resulting residue was taken up in a mixture of ethyl acetate and water and the layers were separated. The organic layer was washed with brine, saturated $NaHCO_3$, 5% HCl, water and brine. This was then dried with $Na_2SO_4$ and concentrated to a colorless oil which was flash chromatographed on $SiO_2$ with 10-45% ethyl acetate/hexane. The product was isolated as a colorless oil weighing 319 mg, 18%. $^1H$ NMR ($CDCl_3$) δ 8.37 (s, 1H), 8.35 (s, 2H), 8.00 (d, 2H, J=8), 7.56 (t, 1H, J=8), 7.31 (d, 2H, J=8), 7.57 (m, 2H), 4.29 (m, 2H), 4.13 (m, 2H), 3.92 (s, 6H), 1.00 (m, 42H); $^{13}C$ NMR ($CDCl_3$) δ 166.1, 163.5, 161.4, 144.1, 134.2, 133.4, 130.5, 129.1, 126.1, 64.7, 52.1, 50.3, 17.7, 11.8; IR (thin film, NaCl) 3322, 2944, 2866, 1736, 1668, 1583, 1530, 1464, 1439, 1384, 1323, 1265, 1203, 1114, 1070, 997, 920, 882, 803, 732, 684 $cm^{-1}$.

b. Preparation of Compound 55

55

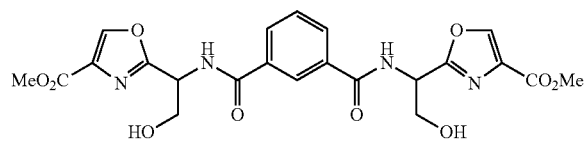

Compound 54 (319 mg, 0.39 mmol) was dissolved in a mixture of anhydrous THF (10 mL) and pyridine (0.5 mL) followed by the addition of HF-pyridine complex (0.25 mL) The reaction stirred under a drying tube overnight at room temperature and a white solid precipitated. A saturated solution of $NaHCO_3$ was added forming a white precipitate which was filtered and washed with water. The solid was collected and the aqueous filtrate was extracted with $CH_2Cl_2$. The organic solution was dried with $Na_2SO_4$ and concentrated in vacuo to a white solid. This was combined with the filtered solid to give 158 mg of product as a white solid, 81%. Melting point 185-187° C. $^1H$ NMR ($CDCl_3$) δ 8.41 (s, 1H), 8.32 (d, 2H, J=8), 8.16 (s, 1H), 8.10 (s, 1H), 7.83 (dd, 2H, J=8, 24), 7.22 (m, 1H), 5.55 (m, 2H), 4.13 (m, 4H), 3.95 (s, 3H), 3.92 (s, 3H); $^{13}C$ NMR ($CDCl_3$) δ 166.8, 163.4, 161.4, 144.4, 133.0, 132.7, 131.5, 128.8, 124.9, 62.6, 52.3, 50.5; IR (thin film, NaCl) 3358, 2954, 1731, 1658, 1584, 1534, 1440, 1324, 1270, 1202, 1148, 1112, 1071, 998, 806, 772, 730 $cm^{-1}$.

c. Preparation of Compound 56.

56

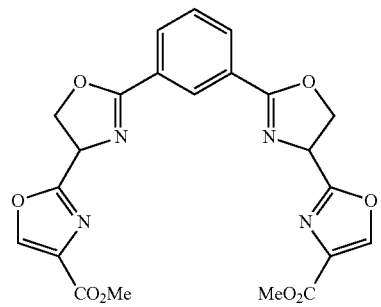

Compound 55 (151 mg, 0.3 mmol) was suspended in anhydrous $CH_2Cl_2$ (8 mL) and placed under argon. After cooling to −78° C., DAST (0.1 mL, 0.79 mmol) was added and the reaction stirred for 4 hours at low temperature. Then $K_2CO_3$ (109 mg, 0.79 mmol) was added and the reaction mixture warmed to room temperature. This was poured into a solution of saturated $NaHCO_3$ and extracted with $CH_2Cl_2$. The combined organic extracts were dried with $Na_2SO_4$ and concentrated to give the product as a colorless oil weighing 119 mg, 85%. $^1H$ NMR ($CDCl_3$) δ 8.57 (s, 1H), 8.27 (s, 2H), 8.13 (d, 2H, J=8), 7.50 (t, 1H, J=8), 5.59 (dd, 2H, J=8, 8), 4.86 (m, 4H), 3.91 (s, 6H); $^{13}C$ NMR ($CDCl_3$) δ 165.7, 163.4, 161.3, 144.8, 133.4, 131.9, 128.8, 128.7, 127.2, 70.7, 63.9, 52.2; IR (thin film, NaCl) 3435, 3160, 2954, 2359, 1740, 1646, 1583, 1438, 1345, 1321, 1272, 1233, 1204, 1144, 1112, 1073, 976, 915, 805, 773, 731, 705 $cm^{-1}$.

d. Preparation of Compound 57.

57

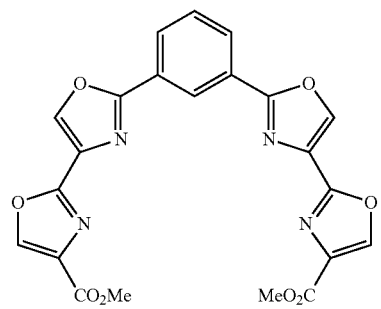

Compound 56 (119 mg, 0.26 mmol) was suspended in anhydrous $CH_3CN$ (7 mL) and placed under argon. This was cooled to 0° C. and treated dropwise with DBU (156 μL, 1.04 mmol) and $BrCCl_3$ (123 μL, 1.25 mmol). The reaction warmed to room temperature overnight and a white precipitate formed. This was filtered and washed with $CH_2Cl_2$ to give the product as a white solid weighing 86 mg, 72%. Melting point 225-227° C. (decomposed). $^1$H NMR ($CDCl_3$+$CD_3OD$) δ 8.88 (s, 1H), 8.54 (s, 2H), 8.50 (s, 2H), 8.30 (d, 2H, J=8), 7.69 (t, 1H, J=8), 3.97 (s, 6H).

e. Preparation of Compound 58.

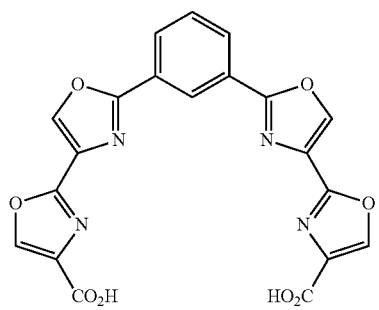

58

Compound 57 (79 mg, 0.17 mmol) was suspended in a mixture of THF (10 mL) and water (3.3 mL) and LiOH (16 mg, 0.37 mmol) was added. This was refluxed overnight followed by partial concentration in vacuo to remove THF. The resulting white precipitate was treated with 5% HCl, filtered and washed with water. This produced 74 mg of product as a white solid, 100%. Melting point >280° C.

Example 23

Preparation of Representative Compound of the Invention (60)

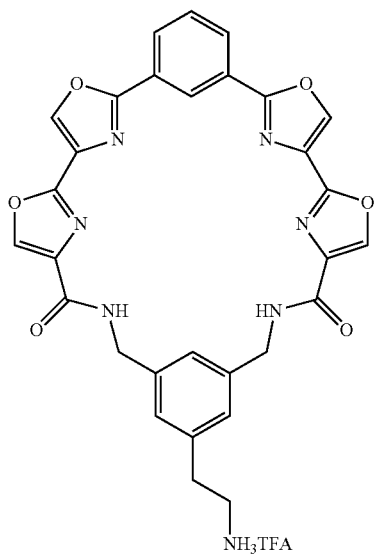

60

Compound 59 (16 mg, 0.024 mmol) was suspended in anhydrous $CH_2Cl_2$ (2 mL) and cooled to 0° C. in an ice bath. This was then treated with TFA (2 mL) and the reaction mixture stirred at 0° C. for 2 hours. The solvent was next removed in vacuo and the resulting solid was azeotroped with benzene twice. The solid was triturated with hexane and $CH_2Cl_2$ to remove nonpolar impurities. The product was isolated as a white solid weighing 14 mg, 88%. $^1$H NMR ($CDCl_3$+$CD_3OD$) δ 9.36 (s, 1H), 8.37 (s, 4H), 8.08 (d, 2H, J=8), 7.66 (t, 1H, J=8), 7.40 (m, 2H), 4.59 (s, 4H), 3.17 (m, 2H), 2.97 (m, 2H); $^{13}$C NMR ($CDCl_3$+$CD_3OD$) δ 161.8, 160.0, 154.9, 141.1, 138.8, 138.0, 138.0, 136.4, 130.4, 129.6, 129.5, 129.1, 127.4, 126.8, 43.4, 40.2, 32.9; IR (thin film, NaCl) 2938, 1660, 1458, 1315, 1179, 1127, 916, 714 cm$^{-1}$.

Example 24

Preparation of Representative Compound of the Invention (61)

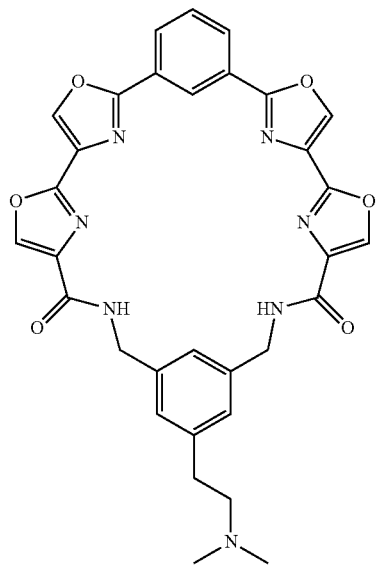

61

Compound 60 (11 mg, 0.016 mmol) was dissolved in 1:4 MeOH/$CH_2Cl_2$ (3 mL) and a solution of 37% aqueous formaldehyde (1 mL) was added. The reaction mixture was allowed to stir at room temperature for 10 min after which sodium triacetoxyborohydride (35 mg, 0.16 mmol) was added. The reaction was stirred at room temperature overnight and was then poured into saturated $NaHCO_3$ and extracted with $CH_2Cl_2$. The organic extracts were dried with $Na_2SO_4$ and concentration in vacuo afforded a white solid. This was flash chromatographed on $SiO_2$ using 3-12% MeOH/$CH_2Cl_2$ with 1% $NH_4OH$ to produce the product as a white solid weighing 5 mg 50%. $^1$H NMR ($CDCl_3$) δ 9.51 (s, 1H), 8.28 (s, 2H), 8.24 (s, 2H), 8.03 (d, 2H, J=8), 7.60 (t, 1H, J=8), 7.32 (m, 2H), 4.60 (d, 4H, J=8), 2.77 (m, 2H), 2.55 (m, 2H), 2.28 (s, 6H); $^{13}$C NMR ($CDCl_3$) δ 162.0, 159.6, 154.9, 142.4, 140.9, 138.6, 137.6, 137.4, 131.0, 130.2, 129.4, 128.8, 128.3, 127.4, 127.0, 61.1, 45.4, 44.0, 33.9; IR (thin film, NaCl) 3390, 3159, 1664, 1591, 1500, 1456, 1369, 1317, 1179, 1110, 981, 918, 810, 765, 714 cm$^{-1}$.

Example 25

Preparation of Representative Compound of the Invention (76)

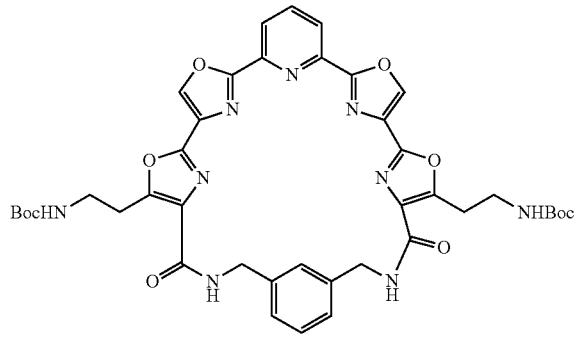

76

Compound 75 (35 mg, 0.049 mmol) and manganese (II) sulfate monohydrate (41 mg, 0.24 mmol) were suspended in anhydrous DMF (35 mL) and placed under argon. This was heated to 65° C. for 15 minutes and then cooled for 10 minutes. Then EDC (38 mg, 0.19 mmol), and HOBT (26 mg, 0.19 mmol) and 2,6-lutidine (45 µL, 0.39 mmol) was added. Then a solution of m-xylylenediamine (6 µL, 0.049 mmol) in DMF (2 mL) was added dropwise. The reaction stirred at room temperature for 2 days and then concentrated in vacuo. The resulting residue was washed with water and the white precipitate was filtered and collected. The solid was flash chromatographed on $SiO_2$ with 1-5% $MeOH/CH_2Cl_2$ to give the product as a white solid weighing 11 mg, 28%. $^1H$ NMR ($CDCl_3$) δ 8.24 (s, 2H), 8.06 (d, 2H, J=8), 7.58 (s, 1H), 7.37 (m, 4H), 5.26 (s, 2H), 4.57 (d, 4H, J=4), 3.55 (m, 4H), 3.37 (t, 4H, J=8), 1.43 (s, 18H); $^{13}C$ NMR ($CDCl_3$) δ 161.1, 160.4, 156.1, 153.7, 152.2, 145.5, 138.8, 138.4, 137.9, 131.9, 131.5, 129.8, 129.4, 122.7, 79.3, 43.8, 39.2, 28.4, 26.4; IR (thin film, NaCl) 3322, 2976, 1695, 1646, 1525, 1440, 1366, 1284, 1250, 1170, 1093, 1047, 992, 926, 780, 734, 707 cm$^{-1}$.

The intermediate compound 76 was prepared as follows.

a. Preparation of Compound 62

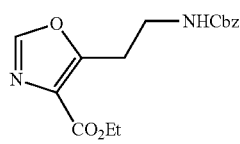

62

Cbz-β-alanine (6.41 g, 28.7 mmol) was dissolved in anhydrous $CH_2Cl_2$ (20 mL) and cooled to 0° C. in an ice bath. It was then treated with oxalyl chloride (5 mL) and stirred at 0° C. for 30 minutes. The reaction was next warmed to room temperature and stirred for 2.5 hours. Removal of solvents in vacuo gave the acid chloride as a colorless oil. This was dissolved in anhydrous DMF (15 mL) and added to a solution of ethyl isocyanoacetate (2.4 mL, 22.1 mmol) and DBU (5 mL, 33.2 mmol) in anhydrous DMF (15 mL) under argon. The dark brown solution was heated to 80° C. for 4.5 hours and was then poured into saturated $NaHCO_3$. This was extracted with ethyl acetate and the combined organic layers were washed with 5% HCl, and brine. After concentration, the resulting brown oil was flash chromatographed on $SiO_2$ with 15-40% ethyl acetate in hexane. The product was isolated as a pale orange oil weighing 3.01 g, 43%. $^1H$ NMR ($CDCl_3$) δ 7.75 (s, 1H), 7.32 (m, 5H), 5.11 (m, 3H), 4.36 (q, 21-1, J=8), 3.55 (m, 2H), 3.28 (t, 2H, J=8), 1.37 (t, 3H, J=8); $^{13}C$ NMR ($CDCl_3$) δ 162.0, 157.0, 156.2, 149.4, 136.5, 128.7, 128.5, 128.4, 128.1, 128.0, 66.7, 61.2, 39.2, 26.6, 14.1; IR (thin film, NaCl) 3338, 3131, 3065, 3033, 2982, 2942, 2248, 1716, 1612, 1525, 1455, 1399, 1379, 1349, 1313, 1254, 1184, 1103, 1073, 1038, 912, 840, 788, 776, 736, 699, 647 cm$^{-1}$.

b. Preparation of Compound 63

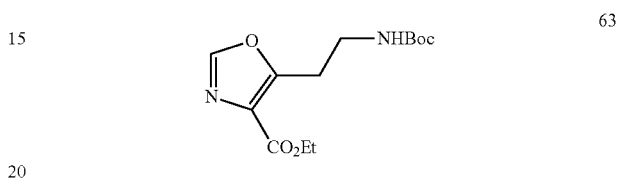

63

Compound 62 (3 g, 9.43 mmol) was dissolved in ethyl acetate (50 mL) and di-tert-butyl dicarbonate (3.09 g, 14.2 mmol) and 10% palladium on carbon (300 mg) were added. This stirred under 1 atm of hydrogen overnight. The reaction mixture was filtered through Celite while washing with ethyl acetate. This was concentrated in vacuo to give a yellow oil which was flash chromatographed on $SiO_2$ with 10-40% ethyl acetate in hexane. The product was isolated as a yellow oil weighing 1.94 g, 72%. $^1H$ NMR ($CDCl_3$) δ 7.82 (s, 1H), 4.92 (br s, 1H), 4.40 (q, 2H, J=8), 3.48 (m, 2H), 3.27 (t, 2H, J=8), 1.41 (t, 3H, J=8); $^{13}C$ NMR ($CDCl_3$) δ 162.0, 157.3, 155.8, 149.4, 128.3, 79.4, 61.2, 33.7, 28.4, 26.8, 14.3; IR (thin film, NaCl) 3366, 3125, 2979, 2936, 2360, 1716, 1612, 1522, 1455, 1393, 1380, 1367, 1349, 1314, 1278, 1252, 1172, 1103, 1074, 1042, 1026, 957, 869, 841, 789, 648 cm$^{-1}$.

c. Preparation of Compound 64

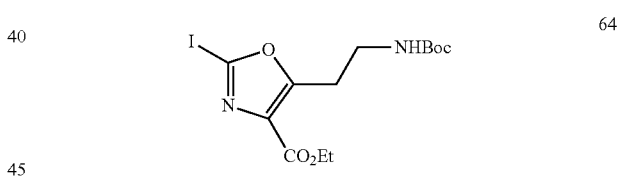

64

Compound 63 (1.94 g, 6.83 mmol) was flushed with argon and dissolved in anhydrous THF (10 mL) The solution was cooled to −42° C. and treated with freshly prepared LiHMDS (19 mL, 15.03 mmol, 0.8 M in THF). The solution became dark yellow in color and stirred for 20 minutes. Then a solution of $ZnCl_2$ (30 mL, 15.03 mmol, 0.5 M in THF) was added and a white precipitate formed. The reaction was warmed to 0° C. for 45 minutes and the solution became clear. Then solid iodine (2.25 g, 8.9 mmol) was added and the reaction stirred at room temperature for 1 hour. The reaction mixture was poured into saturated sodium thiosulfate solution with 25% $NH_4OH$ solution added. This was extracted with ethyl acetate and the combined organic layers were dried with brine and $Na_2SO_4$. Removal of the solvent in vacuo gave the product as an orange oil weighing 2.5 g, 89%. $^1H$ NMR ($CDCl_3$) δ 4.77 (br s, 1H), 4.38 (q, 2H, J=8), 3.46 (m, 2H), 3.26 (t, 2H, J=8), 1.41 (s, 9H); $^{13}C$ NMR ($CDCl_3$) δ 162.6, 160.9, 155.6, 131.9, 99.9, 79.6, 61.4, 38.7, 28.3, 26.9, 14.3; IR (thin film, NaCl) 3367, 2978, 2934, 1698, 1614, 1518, 1494, 1455, 1393, 1367, 1323, 1281, 1250, 1172, 1123, 1076, 1042, 1028, 843, 785, 733 cm$^{-1}$.

d. Preparation of Compound 65.

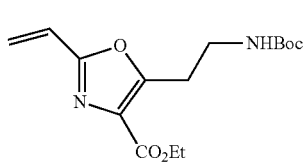

Oxazole 64 (2.5 g, 6.1 mmol) and vinyl tributyltin (2.7 mL, 9.15 mmol) were dissolved in anhydrous dioxane (20 mL0 and placed under argon. Then bis(triphenylphosphine)palladium(II) dichloride (214 mg, 0.31 mmol) was added and the reaction mixture was heated to 105° C. for 4 hours. After cooling the solvent was removed in vacuo and the resulting brown oil was flash chromatographed on $SiO_2$ with 10-30% ethyl acetate in hexane. The product was isolated as a yellow oil weighing 1.49 g, 79%. $^1$H NMR ($CDCl_3$) δ 6.59 (dd, 1H, J=12, 16), 6.21 (d, 1H, J=16), 5.70 (dd, 1H, J=12), 4.86 (br s, 1H), 4.40 (q, 2H, J=8), 3.48 (m, 2H), 3.26 (t, 2H, J=8), 1.41 (s, 9H); $^{13}$C NMR ($CDCl_3$) δ 162.2, 159.3, 156.8, 155.7, 129.4, 123.2, 122.8, 79.4, 61.1, 38.3, 28.3, 26.8, 14.2; IR (thin film, NaCl) 3357, 2978, 2935, 1714, 1607, 1520, 1453, 1393, 1380, 1366, 1326, 1278, 1250, 1176, 1097, 1046, 983, 952, 852, 769, 732 $cm^{-1}$.

e. Preparation of Compound 66.

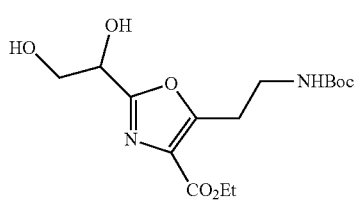

AD-mix-β (17 g) and methane sulfonamide (458 mg, 4.81 mmol) were dissolved in a mixture of tert-butanol (150 mL) and water (150 mL) and stirred at room temperature until clear. Then a solution of oxazole 65 (1.49 g, 4.81 mmol) in tert-butanol (25 mL) was added. The reaction stirred at room temperature for 16 hours and TLC showed it was not complete. Additional AD-mix-β (3 g) and methane sulfonamide (458 mg, 4.81 mmol) were added and the reaction stirred at room temperature for another 24 hours. Then sodium sulfite (22 g) was added and the reaction stirred for 30 minutes. It was next poured into a separatory funnel and the layers were separated. The aqueous layer was extracted with ethyl acetate and the combined aqueous layers were dried with $Na_2SO_4$. The solvent was removed in vacuo to give a pale yellow oil which was flash chromatographed on $SiO_2$ with 2-4% methanol in $CH_2Cl_2$. The product was obtained as a colorless oil weighing 901 mg, 55%. $^1$H NMR ($CDCl_3$) δ 4.84 (m, 2H), 4.38 (q, 211, J=8), 4.01 (m, 2H), 3.64 (br s, 1H), 3.47 (m, 3H), 3.21 (m, 2H), 1.37 (m, 12H); $^{13}$C NMR ($CDCl_3$) δ 162.4, 162.2, 157.3, 156.0, 129.0, 79.9, 68.4, 65.0, 61.2, 38.7, 28.3, 27.4, 14.4; IR (thin film, NaCl) 3406, 2979, 1693, 1520, 1368, 1252, 1168, 1093, 1046 $cm^{-1}$.

f. Preparation of Compound 67.

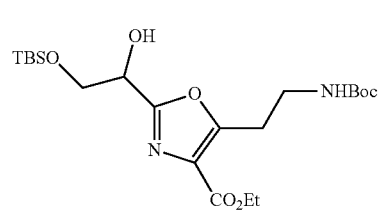

Oxazole 66 (900 mg, 2.62 mmol) and imidazole (356 mg, 5.23 mmol) were dissolved in anhydrous DMF (10 mL) and placed under argon. The reaction mixture was cooled to 0° C. and a solution of tert-butyldimethylsilyl chloride (434 mg, 2.88 mmol) in DMF (2 mL) was added dropwise. This was allowed to slowly warm to room temperature and stirred for 24 hours. Additional tert-butyldimethylsilyl chloride (120 mg, 0.8 mmol) was added and the reaction stirred at room temperature for 6 hours. This was then poured into 5% HCl and extracted with $CH_2Cl_2$. The organic extracts were dried with $Na_2SO_4$ and concentrated in vacuo to give a colorless oil. This was flash chromatographed on $SiO_2$ with 20-40% ethyl acetate in hexane and the product was isolated as a colorless oil weighing 942 mg, 79%. $^1$H NMR ($CDCl_3$) δ 4.82 (m, 1H), 4.80 (br s, 1H), 4.35 (q, 2H, J=8), 3.93 (m, 2H), 3.42 (m, 2H), 3.20 (t, 2H , J=8), 3.12 (d, 1H, J=4), 1.35 (m, 12H), 0.82 (s, 9H), 0.01 (d, 6H, J=4); $^{13}$C NMR ($CDCl_3$) δ 162.1, 161.2, 157.4, 155.7, 128.7, 79.5, 68.5, 65.3, 61.2, 38.8, 28.4, 25.8, 18.2, 14.2, −5.43; IR (thin film, NaCl) 3365, 2955, 2931, 2858, 1717, 1614, 1518, 1463, 1392, 1367, 1326, 1252, 1176, 1127, 1096, 1046, 839, 780 $cm^{-1}$.

g. Preparation of Compound 68.

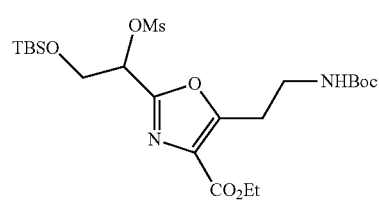

Oxazole 67 (842 mg, 1.84 mmol) was dissolved in anhydrous $CH_2Cl_2$ (20 mL) and placed under argon. The solution was cooled to 0° C. and triethylamine (0.64 mL, 4.6 mmol) was added followed by the dropwise addition of methanesulfonyl chloride (0.21 mL, 2.76 mmol). The reaction stirred at 0° C. for 5 hours and was then poured into brine. This was extracted with $CH_2Cl_2$ and the organic extracts were dried with $Na_2SO_4$. Concentration in vacuo afforded the product as a colorless oil weighing 958 mg, 97%. $^1$H NMR ($CDCl_3$) δ 5.58 (dd, 1H, J=4, 8), 4.79 (br s, 1H), 4.32 (q, 2H, J=8), 4.08 (m, 2H), 3.38 (m, 2H), 3.17 (m, 2H), 3.02 (m, 4H), 1.32 (m, 12H), 0.80 (s, 9H), 0.01 (d, 6H, J=4); $^{13}$C NMR ($CDCl_3$) δ 161.7, 158.3, 156.7, 155.7, 129.2, 79.5, 75.2, 63.3, 61.4, 45.9, 38.8, 28.3, 27.1, 25.7, 18.2, 14.3, −5.38; IR (thin film, NaCl) 3407, 2933, 2858, 2251, 1716, 1611, 1513, 1473, 1366, 1253, 1175, 1133, 1094, 1031, 971, 918, 839, 782, 735, 668, 647 $cm^{-1}$.

h. Preparation of Compound 69.

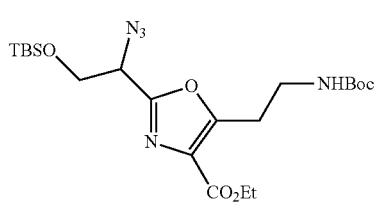

69

Oxazole 68 (958 mg, 1.79 mmol) and sodium azide (581 mg, 8.74 mmol) were dissolved in anhydrous DMF (10 mL) and placed under argon. The reaction stirred at room temperature for 17 hours and was then poured into brine. This was extracted with ethyl acetate and the combined organic extracts were dried with $Na_2SO_4$. Concentration in vacuo afforded the product as a colorless oil weighing 813 mg, 94%. $^1$H NMR (CDCl$_3$) δ 4.76 (br s, 1H), 4.57 (m, 1H), 4.30 (q, 2H, J=8), 4.01 (m, 2H), 3.38 (m, 2H), 3.16 (t, 2H, J=8), 1.31 (m, 12H), 0.80 (s, 9H), 0.00 (d, 6H, J=4); $^{13}$C NMR (CDCl$_3$) δ 160.8, 157.1, 156.8, 154.7, 127.9, 78.4, 63.5, 60.3, 58.7, 37.7, 27.3, 25.9, 24.6, 17.1, 13.3, −6.53; IR (thin film, NaCl) 3372, 2932, 2858, 2107, 1716, 1613, 1514, 1464, 1366, 1323, 1253, 1175, 1096, 1031, 839, 780, 733 cm$^{-1}$.

i. Preparation of Compound 70.

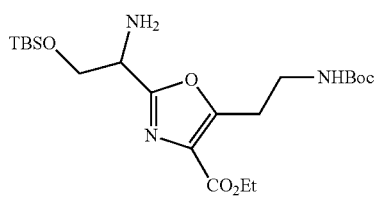

70

Oxazole 69 (813 mg, 1.68 mmol) was dissolved in a mixture of THF (20 mL) and water (2 mL) and polymer supported triphenylphosphine (842 mg, 2.52 mmol, ~3 mmol/g) was added. This stirred at room temperature overnight and TLC revealed the reaction was not complete. Additional polymer supported triphenylphosphine (300 mg, 0.9 mmol) was added and the reaction stirred for 3 more hours. The resin was then filtered and washed with ethyl acetate. The filtrate was dried with $Na_2SO_4$ and concentrated in vacuo to give the product as a pale yellow oil weighing 510 mg, 66%. $^1$H NMR (CDCl$_3$) δ 4.78 (br s, 1H), 4.36 (q, 2H, J=8), 4.13 (m, 1H), 3.90 (m, 2H), 3.42 (m, 2H), 3.18 (t, 2H, J=8), 2.29 (br s, 2H), 1.36 (m, 12H), 0.82 (s, 9H), −0.01 (d, 6H, J=4); $^{13}$C NMR (CDCl$_3$) δ 162.3, 157.0, 156.5, 155.7, 128.6, 79.4, 65.9, 61.2, 52.1, 39.9, 28.4, 26.8, 25.8, 18.2, 14.4, −5.44; IR (thin film, NaCl) 3379, 2931, 2857, 1716, 1615, 1518, 1463, 1366, 1252, 1174, 1095, 838, 779 cm$^{-1}$.

j. Preparation of Compound 71.

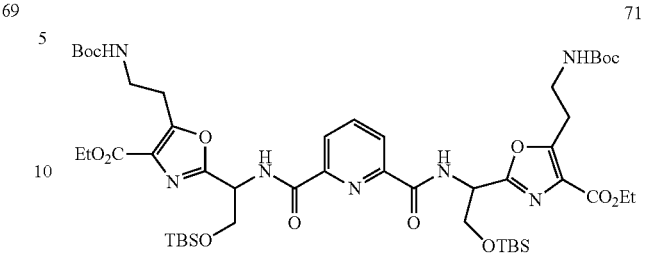

71

2,6-pyridinedicarboxylic acid (37 mg, 0.22 mmol), oxazole 70 (200 mg, 0.44 mmol), EDC (172 mg, 0.88 mmol) and HOBT (118 mg, 0.88 mmol) were dissolved in anhydrous DMF (10 mL). 2,6-Lutidine (0.26 mL, 2.2 mmol) was added and the reaction mixture was placed under argon. The reaction mixture stirred at room temperature overnight and then the solvent was removed in vacuo. The resulting residue was taken up in a mixture of ethyl acetate and water and the layers were separated. The organic layer was washed with brine, saturated NaHCO$_3$, 5% HCl, water and brine. This was then dried with Na$_2$SO$_4$ and concentrated to give the product as a colorless oil weighing 195 mg, 85%. $^1$H NMR (CDCl$_3$) δ 8.36 (m, 2H), 8.02 (m, 1H), 5.52 (m, 1H), 4.36 (m, 4H), 4.13 (m, 2H), 3.42 (m, 2H), 3.17 (m, 2H), 1.30 (m, 24H), 0.80 (s, 18H), 0.00 (s, 12H); $^{13}$C NMR (CDCl$_3$) δ 163.2, 160.8, 157.1, 156.0, 148.6, 138.9, 127.1, 125.7, 79.4, 63.6, 61.0, 49.8, 38.7, 28.3, 26.9, 25.6, 21.3, 18.0, −5.2; IR (thin film, NaCl) 3343, 2931, 2858, 1716, 1615, 1525, 1463, 1392, 1367, 1348, 1325, 1253, 1175, 1122, 1094, 1032, 1003, 919, 840, 780, 735 cm$^{-1}$.

k. Preparation of Compound 72.

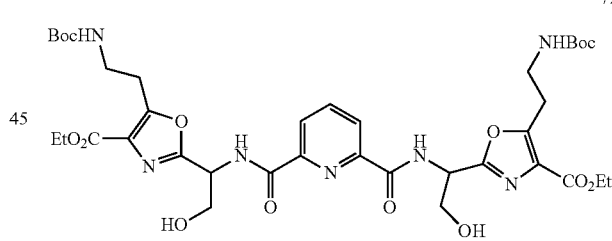

72

Compound 71 (192 mg, 0.18 mmol) was dissolved in a mixture of anhydrous THF (10 mL) and pyridine (0.5 mL) followed by the addition of HF-pyridine complex (0.25 mL) The reaction stirred under a drying tube overnight at room temperature and a white solid precipitated. This was poured into a saturated solution of NaHCO$_3$ and extracted with CH$_2$Cl$_2$. The organic extracts were dried with Na$_2$SO$_4$ and concentrated in vacuo to give 134 mg of product as a yellow oil, 89%. $^1$H NMR (CDCl$_3$) δ 8.60 (s, 2H), 7.67 (m, 1H), 5.50 (m, 1H), 4.23 (m, 4H), 3.45 (m, 2H), 3.15 (m, 2H), 1.36 (m, 24H); $^{13}$C NMR (CDCl$_3$) δ 163.6, 161.9, 157.8, 156.0, 155.9, 148.5, 125.3, 123.8, 79.5, 62.9, 61.2, 53.5, 37.7, 28.3, 27.1, 14.2; IR (thin film, NaCl) 3339, 2978, 2934, 2248, 1716, 1616, 1529, 1445, 1367, 1347, 1325, 1281, 1250, 1174, 1092, 1047, 1000, 917, 846, 788, 733, 706 cm$^{-1}$.

l. Preparation of Compound 73.

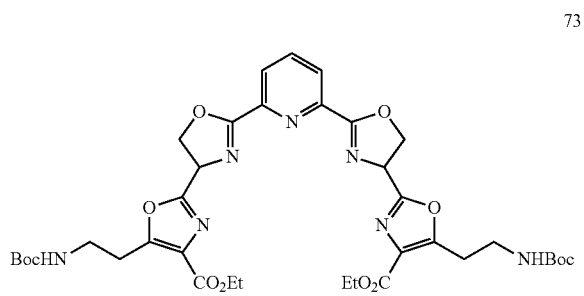 [SMILES: CCOC(=O)c1nc(C2COC(c3cccc(C4=NC(c5nc(C(=O)OCC)c(CCNC(=O)OC(C)(C)C)o5)CO4)n3)=N2)oc1CCNC(=O)OC(C)(C)C]

73

Compound 72 (134 mg, 0.16 mmol) was dissolved in anhydrous CH$_2$Cl$_2$ (5 mL) and placed under argon. After cooling to −78° C., DAST (54 μL, 0.41 mmol) was added and the reaction stirred for 3 hours at low temperature. Then K$_2$CO$_3$ (57 mg, 0.41 mmol) was added and the reaction mixture warmed to room temperature. This was poured into a solution of saturated NaHCO$_3$ and extracted with CH$_2$Cl$_2$. The combined organic extracts were dried with Na$_2$SO$_4$ and concentrated to give the product as an orange oil weighing 116 mg, 91%. $^1$H NMR (CDCl$_3$) δ 8.25 (d, 2H, J=8), 7.93 (t, 1H, J=8), 5.61 (t, 2H, J=8), 4.91 (m, 6H), 4.39 (q, 4H, J=8), 3.46 (m, 4H), 3.24 (t, 4H, J=8), 1.41 (m, 24H); $^{13}$C NMR (CDCl$_3$) δ 164.9, 162.0, 160.6, 158.1, 155.7, 146.2, 137.6, 128.9, 126.8, 79.5, 71.3, 64.0, 61.2, 38.7, 28.3, 18.9; IR (thin film, NaCl) 3364, 2977, 1713, 1520, 1458, 1366, 1250, 1175, 1093, 1031, 921, 844, 733 cm$^{-1}$.

m. Preparation of Compound 74.

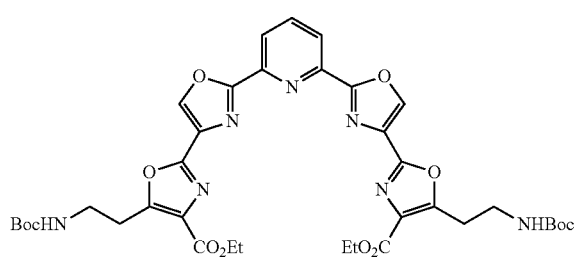

74

Compound 73 (116 mg, 0.15 mmol) was suspended in anhydrous CH$_3$CN (3 mL) and placed under argon. This was cooled to 0° C. and treated dropwise with DBU (89 μL, 0.59 mmol) and BrCCl$_3$ (71 μL, 0.72 mmol). The reaction was warmed to room temperature overnight and a white precipitate formed. The precipitate was filtered and washed with CH$_2$Cl$_2$. The filtrate was poured into 1N HCl and extracted with CH$_2$Cl$_2$. The organic extract was dried with Na$_2$SO$_4$ and concentrated in vacuo to give a brown oil. This was flash chromatographed on SiO$_2$ with 1-4% methanol/CH$_2$Cl$_2$. The product was isolated as a white solid weighing 58 mg, 50%. $^1$H NMR (CDCl$_3$+CD$_3$OD) δ 8.55 (s, 2H), 8.43 (d, 2H, J=4), 8.08 (t, 1H, J=8), 5.13 (br s, 2H), 4.44 (d, 4H, J=8), 3.56 (m, 4H), 3.36 (m, 4H), 1.42 (m, 24H); $^{13}$C NMR (CDCl$_3$+CD$_3$OD) δ 161.8, 160.4, 157.3, 155.7, 153.2, 145.5, 140.6, 138.4, 131.4, 129.7, 124.2, 79.3, 61.3, 38.1, 28.3, 27.0, 14.3; IR (thin film, NaCl) 3355, 2978, 1710, 1639, 1524, 1452, 1367, 1250, 1171, 1089, 1048, 926, 733 cm$^{-1}$.

n. Preparation of Compound 75.

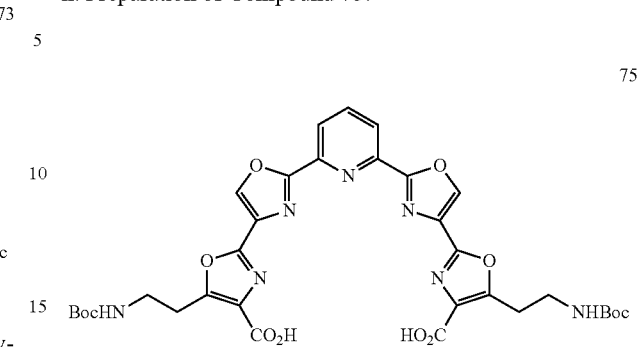

75

Compound 74 (58 mg, 0.075 mmol) was suspended in a mixture of THF (10 mL) and water (3.3 mL) and LiOH (7 mg, 0.16 mmol) was added. This was heated to 60° C. for 30 minutes and then stirred at room temperature overnight. The solvent was concentrated in vacuo to remove THF. The resulting white precipitate was treated with 5% HCl, filtered and washed with water. This produced 35 mg of product as a white solid, 65%. $^1$H NMR (CDCl$_3$+CD$_3$OD) δ 8.28 (s, 2H), 8.11 (d, 2H, J=4), 7.82 (t, 1H, J=8), 5.44 (br s, 2H), 3.22 (m, 4H), 3.05 (m, 4H), 1.13 (s, 18H); $^{13}$C NMR (CDCl$_3$+CD$_3$OD) δ 168.2, 165.1, 161.9, 157.8, 157.7, 150.3, 145.3, 143.3, 136.4, 134.8, 128.9, 83.6, 43.6, 35.1, 19.1; IR (thin film, NaCl) 3439, 2977, 2253, 2127, 1702, 1525, 1453, 1392, 1366, 1342, 1281, 1250, 1173, 1026, 926, 824, 762, 710 cm$^{-1}$.

Example 26

Preparation of Representative Compound of the Invention (77)

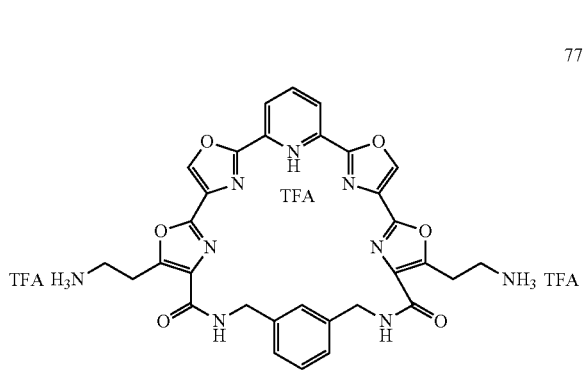 [SMILES: NCCc1oc2nc1C(=O)NCc1cccc(c1)CNC(=O)c1nc(oc1CCN)-c1coc(n1)-c1cccc(n1)-c1nc-2co1]

77

Compound 76 (10 mg, 0.012 mmol) was suspended in anhydrous CH$_2$Cl$_2$ (2 mL) and cooled to 0° C. in an ice bath. This was then treated with TFA (2 mL) and the reaction mixture stirred at 0° C. for 1 hour. The solvent was next removed in vacuo and the resulting solid was azeotroped with benzene twice. The product was isolated as a white solid weighing 11 mg, 100%. $^1$H NMR (CD$_3$OD) δ 8.63 (s, 2H), 8.57 (s, 41-1), 7.53 (s, 1H), 7.30 (s, 4H), 4.48 (s, 4H), 3.42 (s, 4H); IR (thin film, NaCl) 3405, 2964, 2926, 2855, 1653, 1529, 1452, 1266, 1025, 992, 827, 800 cm$^{-1}$.

Example 27

Preparation of Representative Compound of the Invention (78)

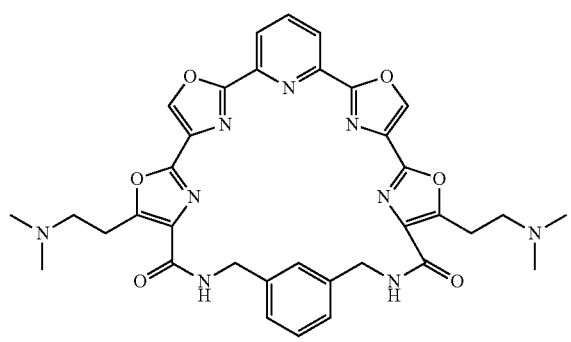

Compound 77 (8 mg, 0.009 mmol) was dissolved in 1:4 MeOH/CH$_2$Cl$_2$ (3 mL) and a solution of 37% aqueous formaldehyde (1 mL) was added. The reaction mixture was allowed to stir at room temperature for 10 min after which sodium triacetoxyborohydride (35 mg, 0.16 mmol) was added. The reaction stirred at room temperature overnight and was then poured into saturated NaHCO$_3$ and extracted with CH$_2$Cl$_2$. The organic extracts were dried with Na$_2$SO$_4$ and concentration in vacuo afforded the product as a white solid weighing 6 mg 100%. $^1$H NMR (CDCl$_3$+CD$_3$OD) δ 8.31 (s, 2H), 8.08 (s, 3H), 7.52 (s, 1H), 7.35 (s, 3H), 5.32 (s, 4H), 2.80 (t, 4H, J=8), 2.39 (m, 16H); $^{13}$C NMR (CDCl$_3$+CD$_3$OD) δ 162.5, 160.9, 145.4, 139.0, 129.4, 129.1, 122.8, 64.5, 44.9, 43.7, 23.9.

Example 28

Preparation of Intermediate of the Invention (82)

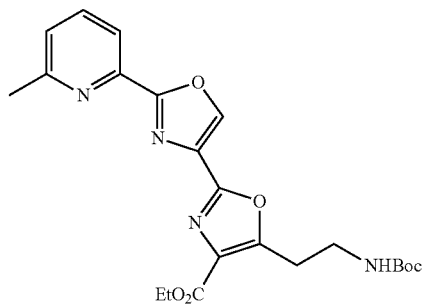

Compound 81 (248 mg, 0.56 mmol) was suspended in anhydrous CH$_3$CN (3 mL) and placed under argon. This was cooled to 0° C. and treated dropwise with DBU (167 μL, 1.18 mmol) and BrCCl$_3$ (132 μL, 1.34 mmol). The reaction warmed to room temperature overnight and then poured into 1N HCl and extracted with CH$_2$Cl$_2$. The organic extract was dried with Na$_2$SO$_4$ and concentrated in vacuo to give a brown oil. This was flash chromatographed on SiO$_2$ with 1-3% methanol/CH$_2$Cl$_2$. The product was isolated as a yellow oil weighing 100 mg, 40%. $^1$H NMR (CDCl$_3$) δ 8.48 (s, 1H), 8.09 (d, 1H, J=8), 7.75 (t, 1H, J=8), 7.30 (m, 1H), 4.95 (br s, 1H), 4.42 (q, 2H, J=8), 3.57 (m, 2H), 3.35 (t, 2H, J=8), 2.68 (s, 3H), 1.43 (m, 12H); $^{13}$C NMR (CDCl$_3$) δ 161.9, 161.5, 159.2, 157.2, 155.7, 153.5, 144.6, 140.1, 137.2, 131.2, 129.7, 125.2, 120.0, 79.4, 61.3, 38.9, 28.2, 26.9, 24.6, 14.3; IR (thin film, NaCl) 3356, 2978, 1712, 1594, 1525, 1459, 1366, 1345, 1251, 1172, 1084, 1046, 926, 805, 734 cm$^{-1}$.

a. Preparation of Compound 79.

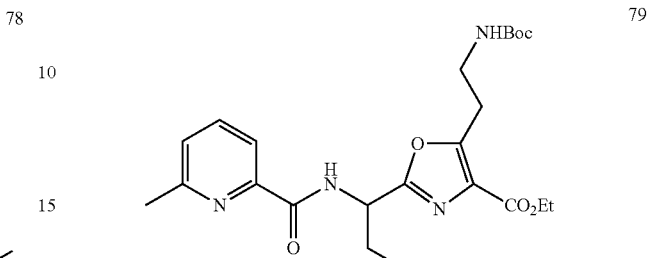

6-Methylpicolinic acid (137 mg, 1 mmol), oxazole 70 (306 mg, 0.67 mmol), EDC (257 mg, 1.34 mmol) and HOBT (181 mg, 1.34 mmol) were dissolved in anhydrous DMF (15 mL) Then 2,6-lutidine (0.4 mL, 3.35 mmol) was added and the reaction was placed under argon. The reaction stirred at room temperature for 16 hours and was then concentrated in vacuo. The residue was dissolved in ethyl acetate and water and poured into brine. The organic layer was washed successively with saturated NaHCO$_3$, 1N HCl, water and brine. This was then dried with Na$_2$SO$_4$ and concentrated to a pale brown oil weighing 386 mg, 100%. $^1$H NMR (CDCl$_3$) δ 7.90 (d, 1H, J=8), 7.63 (m, 1H), 7.25 (d, 1H, J=8), 5.38 (m, 1H), 4.86 (s, 1H), 4.32 (q, 2H, J=8), 4.13, (dd, 1H, J=4, 12), 4.00 (dd, 1H, J=4, 8), 3.38 (m, 2H), 3.16 (t, 2H, J=8), 2.51 (s, 3H), 1.31 (m, 12H), 0.81 (s, 9H), −0.02 (d, 6H, J=4); $^{13}$C NMR (CDCl$_3$) δ 164.4, 162.0, 161.0, 160.2, 157.4, 155.7, 148.5, 137.4, 128.7, 120.5, 119.4, 79.3, 64.2, 61.1, 49.5, 38.8, 28.3, 26.8, 25.6, 24.1, 18.0, 14.2, −5.6; IR (thin film, NaCl) 3380, 2955, 2930, 2857, 1795, 1716, 1614, 1595, 1515, 1454, 1366, 1346, 1325, 1255, 1173, 1095, 1043, 994, 921, 839, 781, 746, 665 cm$^{-1}$.

b. Preparation of Compound 80.

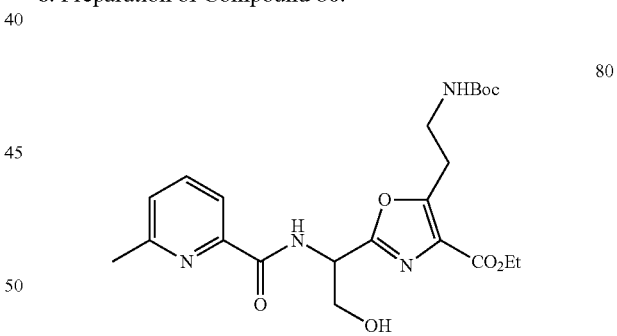

Compound 79 (386 mg, 0.67 mmol) was dissolved in a mixture of anhydrous THF (10 mL) and pyridine (1 mL) followed by the addition of HF-pyridine complex (0.25 mL). The reaction stirred under a drying tube overnight at room temperature and a white solid precipitated. This was poured into a saturated solution of NaHCO$_3$ and extracted with CH$_2$Cl$_2$. The organic extracts were dried with Na$_2$SO$_4$ and concentrated in vacuo to give 134 mg of product as a colorless oil, 87%. $^1$H NMR (CDCl$_3$) δ 7.97 (d, 1H, J=8), 7.73 (m, 1H), 7.28 (d, 1H, J=8), 5.50 (m, 1H), 5.01 (m, 1H), 4.37 (q, 2H, J=8), 4.23 (dd, 1H, J=4, 12), 4.07 (dd, 1H, J=4, 12), 3.46 (m, 2H), 3.22 (m, 2H), 2.58 (s, 3H), 1.36 (m, 12H); $^{13}$C NMR (CDCl$_3$) δ 164.8, 162.1, 161.0, 159.2, 157.4, 156.0, 149.6, 137.4, 123.8, 119.5, 79.6, 64.0, 61.1, 49.8, 38.7, 28.3, 26.9, 21.3, 14.3; IR (thin film, NaCl) 3376, 3058, 2979, 2934, 2249, 1716, 1615, 1596, 1517, 1454, 1367, 1253, 1173, 1091, 1032, 994, 913, 852, 824, 788, 759, 734, 704, 647 cm$^{-1}$.

c. Preparation of Compound 81.

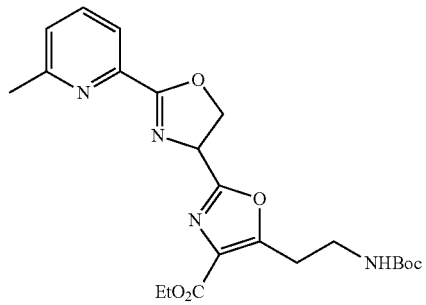

81

Compound 80 (270 mg, 0.58 mmol) was dissolved in anhydrous CH$_2$Cl$_2$ (5 mL) and placed under argon. After cooling to −78° C., DAST (116 µL, 0.88 mmol) was added and the reaction stirred for 3 hours at low temperature. Then K$_2$CO$_3$ (122 mg, 0.88 mmol) was added and the reaction mixture warmed to room temperature. This was poured into a solution of saturated NaHCO$_3$ and extracted with CH$_2$Cl$_2$. The combined organic extracts were dried with Na$_2$SO$_4$ and concentrated to give the product as a colorless oil weighing 248 mg, 96%. $^1$H NMR (CDCl$_3$) δ 7.97 (d, 1H, J=8), 7.70 (m, 1H), 7.33 (d, 1H, J=8), 5.60 (t, 1H, J=8), 4.90 (m, 2H), 4.40 (q, 2H, J=8), 3.46 (m, 2H), 3.18 (t, 2H, J=8), 2.64 (s, 3H), 1.34 (m, 12H); $^{13}$C NMR (CDCl$_3$) δ 164.7, 161.8, 160.8, 159.2, 158.0, 157.7, 155.6, 136.8, 125.9, 121.6, 119.4, 79.4, 65.0, 63.2, 61.1, 38.7, 28.2, 27.2, 24.5, 13.6; IR (thin film, NaCl) 3370, 2978, 2933, 2247, 1714, 1613, 1594, 1517, 1454, 1367, 1347, 1323, 1251, 1174, 1092, 1031, 970, 918, 852, 788, 759, 733 cm$^{-1}$.

Example 29

Preparation of Representative Compound of the Invention (83)

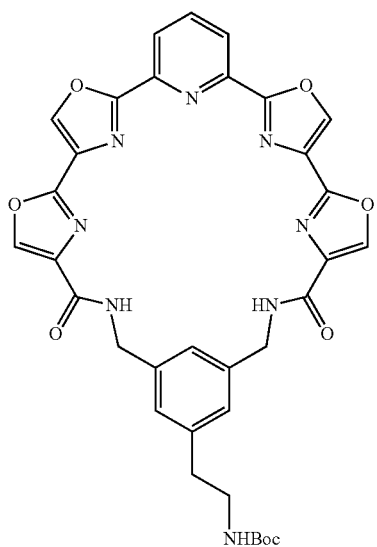

83

The yield of the macrocyclization step, as utilized in this example and in certain preceding examples, can be increased by complexing the pentacyclic diacid with a metal prior to cyclization. A representative procedure for this reaction is described below. Compound 5 (50 mg, 0.115 mmol) and manganese (II) sulfate monohydrate (97 mg, 0.58 mmol) were suspended in dry DMF (50 mL) and placed under an argon atmosphere. This was heated to 65° C. for 5 minutes and then cooled to room temperature. Then EDC (88 mg, 0.46 mmol), HOBT (62 mg, 0.46 mmol) and 2,6-lutidine (107 µL, 0.92 mmol) were added. Next a solution of tert-butyl 3,5-bis(aminomethyl)phenethylcarbamate (32 mg, 0.115 mmol) in DMF (5 mL) was added dropwise. This stirred at room temperature for 48 hours and then the solvent was removed in vacuo. The resulting residue was washed with water and the white precipitate was filtered and collected. The solid was flash chromatographed on SiO$_2$ with 1.5-4% MeOH/CH$_2$Cl$_2$ to give the product as a white solid weighing 33 mg, 42%. $^1$H NMR (CDCl$_3$+CD$_3$OD) δ 8.33 (s, 2H), 8.29 (s, 2H), 8.90 (s, 3H), 7.42 (s, 1H), 7.18 (s, 2H), 4.60 (d, 4H, J=4), 3.34 (m, 2H), 2.78 (t, 2H, J=8), 1.38 (s, 9H); $^{13}$C NMR (CDCl$_3$+CD$_3$OD) δ 160.8, 160.2, 160.1, 156.1, 154.2, 145.1, 141.4, 140.6, 139.3, 138.9, 138.0, 137.7, 137.7, 131.7, 129.6, 128.3, 122.8, 79.2, 53.5, 43.8, 35.9, 28.4; IR (thin film, NaCl) 3374, 1704, 1650, 1592, 1506, 1456, 1345, 1365, 1325, 1286, 1265, 1168, 1101, 983, 959, 917, 819, 778, 724, 707 cm$^{-1}$.

Example 30

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

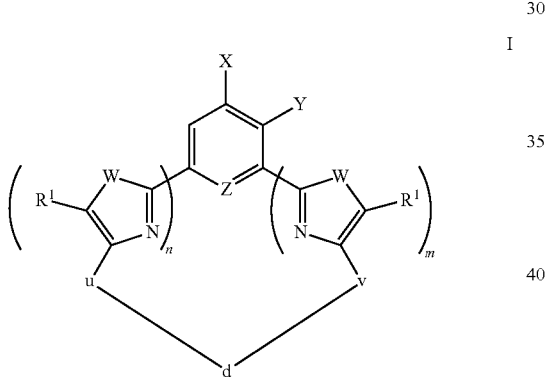

wherein:
Z is CH or N;
each W is independently NH, S, or O;
n is 1 and m is 3; or n is 2 and m is 2; or n is 3 and m is 1; or n is 4 and m is 0;
X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;
Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, $-NR_aR_b$, $-C(=O)NR_aR_b$, or $-NR_aC(=O)-R_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, $-NR_aR_b$, $-C(=O)NR_aR_b$, and $-NR_aC(=O)-R_c$;

each $R^1$ is independently H or $(C_1-C_6)$alkyl wherein any $(C_1-C_6)$alkyl of $R^1$ is optionally is optionally substituted with one or more groups independently selected from hydroxy, halo, cyano, nitro, $(C_1-C_3)$alkoxy, $(C_1-C_3)$alkanoyl, $(C_1-C_3)$alkanoyl oxy, $(C_1-C_3)$alkoxycarbonyl, $-NR_{a1}R_{b1}$, $-C(=O)NR_{a1}R_{b1}$, and $-NR_{a1}C(=O)-R_{c1}$;

each $R_a$ and $R_b$ is independently H, $(C_1-C_6)$alkyl, $(C_1-C_6)$alkanoyl, or aryl$(C_1-C_6)$alkyl; or $R_a$ and $R_b$ together with the nitrogen to which they are attached form an N-linked heterocycle containing from 3 to 10 atoms that is optionally substituted with one or more oxo;

each $R_c$ is $(C_1-C_3)$haloalkyl;

each $R_{a1}$ and $R_{b1}$ is independently H, $(C_1-C_6)$alkyl, $(C_1-C_6)$alkanoyl, or aryl$(C_1-C_6)$alkyl; or $R_{a1}$ and $R_{b1}$ together with the nitrogen to which they are attached form an N-linked heterocycle containing from 3 to 10 atoms that is optionally substituted with one or more oxo;

each $R_{c1}$ is halo$(C_1-C_6)$alkyl, $(C_1-C_6)$alkoxy or aryl$(C_1-C_6)$alkoxy; and wherein -u-d-v- is selected from:

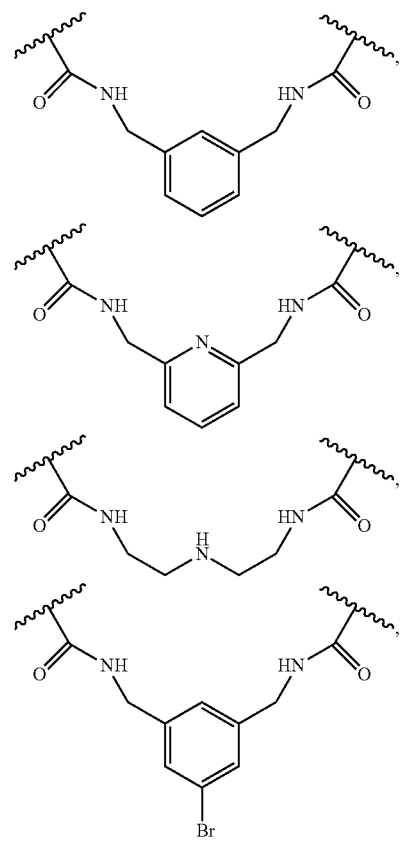

109
-continued
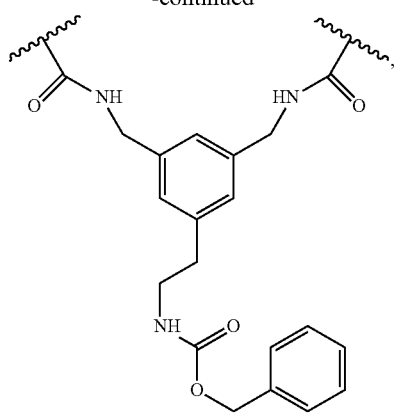
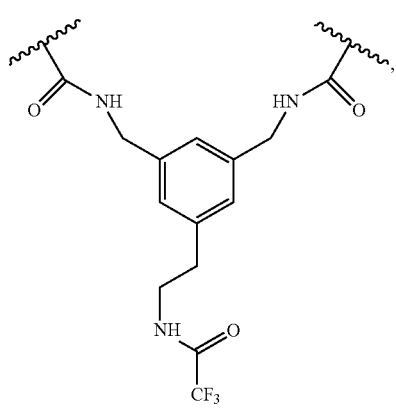
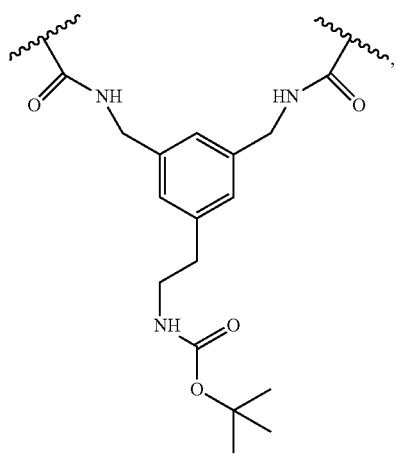
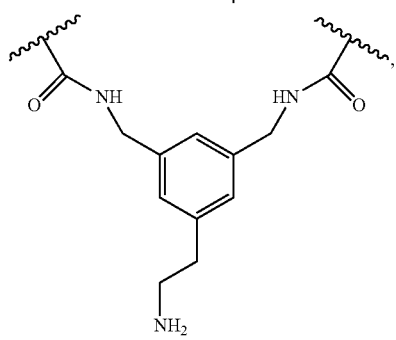
110
-continued
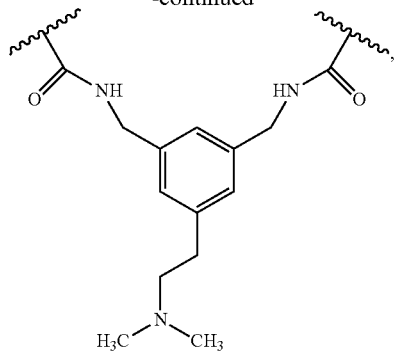
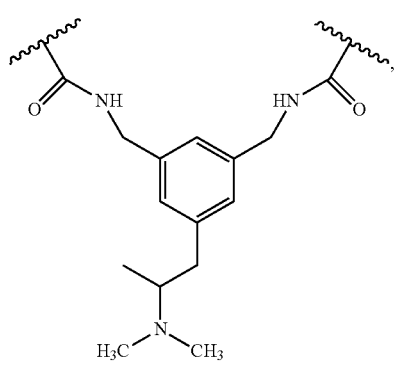
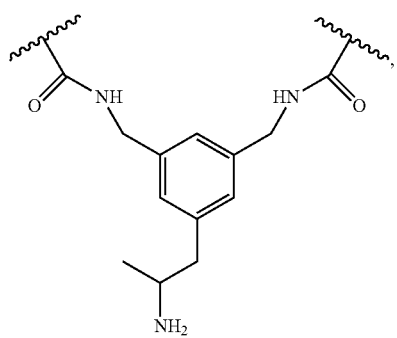
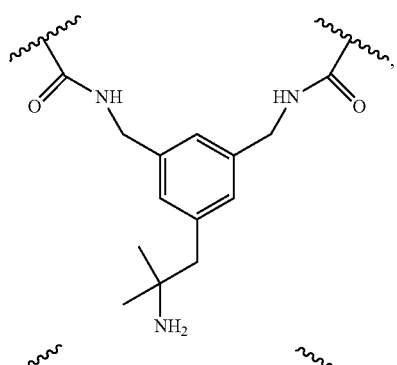
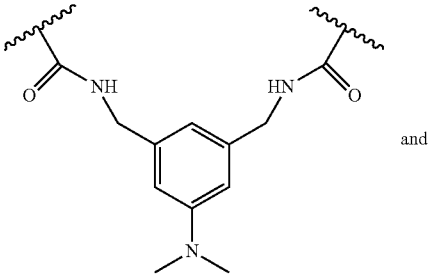
and -continued

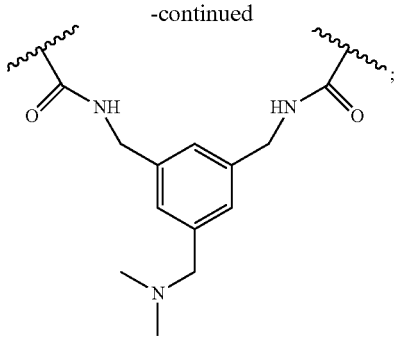

or a salt thereof.

2. The compound of claim 1 wherein n is 1 and m is 3.
3. The compound of claim 1 wherein n is 2 and m is 2.
4. The compound of claim 1 wherein n is 3 and m is 1.
5. A compound of formula Ia:

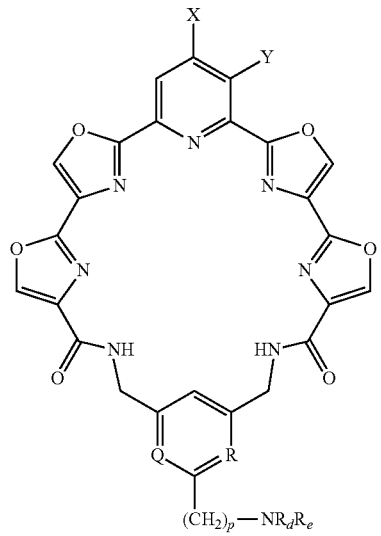

Ia wherein:
X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —NR$_a$R$_b$, —C(=O)NR$_a$R$_b$, or —NR$_a$C(=O)—R$_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —NR$_a$R$_b$, —C(=O)NR$_a$R$_b$, and —NR$_a$C(=O)—R$_c$;
Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —NR$_a$R$_b$, —C(=O)NR$_a$, R$_b$, or —NR$_a$C(=O)—R$_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —NR$_a$R$_b$, —C(=O)NR$_a$R$_b$, and —NR$_a$C(=O)—R$_c$;
Q is CH or N;
R is CH or N;
p is 0, 1, 2, 3, or 4;
each R$_a$ and R$_b$ is independently H, $(C_1-C_6)$alkyl, $(C_1-C_6)$alkanoyl, or aryl$(C_1-C_6)$alkyl; or R$_a$ and R$_b$ together with the nitrogen to which they are attached form an N-linked heterocycle containing from 3 to 10 atoms that is optionally substituted with one or more oxo;
each R$_c$ is $(C_1-C_3)$haloalkyl; and
each R$_d$ and R$_e$ is independently H or $(C_1-C_6)$alkyl;
or a salt thereof.

6. A compound of formula Ib:

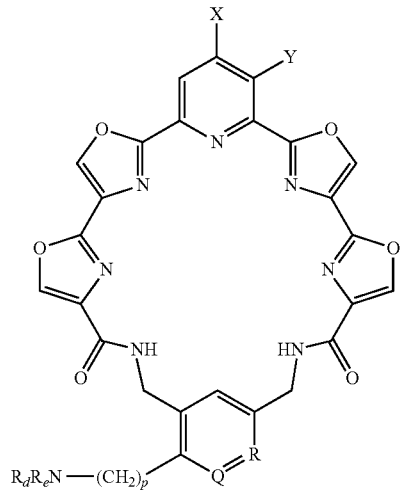

Ib wherein:
X is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —NR$_a$R$_b$, —C(=O)NR$_a$R$_b$, or —NR$_a$C(=O)—R$_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of X is optionally substituted with one or more groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —NR$_a$R$_b$, —C(=O)NR$_a$R$_b$, and —NR$_a$C(=O)—R$_c$;
Y is H, hydroxy, halo, cyano, nitro, $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, $(C_1-C_6)$alkoxycarbonyl, —NR$_a$R$_b$, —C(=O)NR$_a$,R$_b$, or —NR$_a$C(=O)—R$_c$; wherein each $(C_1-C_6)$alkyl, $(C_2-C_6)$alkenyl, $(C_2-C_6)$alkynyl, $(C_1-C_6)$alkoxy, $(C_1-C_6)$alkanoyl, $(C_1-C_6)$alkanoyloxy, and $(C_1-C_6)$alkoxycarbonyl of Y is optionally substituted with one or more groups independently selected from hydroxy, halo, cyano, nitro, $(C_1-C_3)$alkoxy, $(C_1-C_3)$alkanoyl, $(C_1-C_3)$alkanoyloxy, $(C_1-C_3)$alkoxycarbonyl, —NR$_a$R$_b$, —C(=O)NR$_a$R$_b$, and —NR$_a$C(=O)—R$_c$;

Q is CH or N;
R is CH or N;
p is 0, 1, 2, 3, or 4;
each $R_a$ and $R_b$ is independently H, ($C_1$-$C_6$)alkyl, ($C_1$-$C_6$)alkanoyl, or aryl($C_1$-$C_6$)alkyl; or $R_a$ and $R_b$ together with the nitrogen to which they are attached form an N-linked heterocycle containing from 3 to 10 atoms that is optionally substituted with one or more oxo;
each $R_c$ is ($C_1$-$C_3$)haloalkyl; and
each $R_d$ and $R_e$ is independently H or ($C_1$-$C_6$)alkyl;
or a salt thereof.

7. A compound of formula Ic:

Ic wherein:
X is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_aR_b$, —C(=O)$NR_aR_b$, or —$NR_aC$(=O)—$R_c$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl of X is optionally substituted with one or more groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_aR_b$, —C(=O)$NR_aR_b$, and —$NR_aC$(=O)—$R_c$;
Y is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_aR_b$, —C(=O)$NR_aR_b$, or —$NR_aC$(=O)—$R_c$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl of Y is optionally substituted with one or more groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_aR_b$, —C(=O)$NR_aR_b$, and —$NR_aC$(=O)—$R_c$;
Q is CH or N;
R is CH or N;
p is 0, 1, 2, 3, or 4;
each $R^1$ is independently H or ($C_1$-$C_6$)alkyl wherein any ($C_1$-$C_6$)alkyl of $R^1$ is optionally is optionally substituted with one or more groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_{a1}R_{b1}$, —C(=O)$NR_{a1}R_{b1}$, and —$NR_{a1}C$(=O)—$R_{c1}$;
each $R_a$ and $R_b$ is independently H, ($C_1$-$C_6$)alkyl, ($C_1$-$C_6$)alkanoyl, or aryl($C_1$-$C_6$)alkyl; or $R_a$ and $R_b$ together with the nitrogen to which they are attached form an N-linked heterocycle containing from 3 to 10 atoms that is optionally substituted with one or more oxo;
each $R_c$ is ($C_1$-$C_3$)haloalkyl;
each $R_d$ and $R_e$ is independently H or ($C_1$-$C_6$)alkyl;
each $R_{a1}$ and $R_{b1}$ is independently H, ($C_1$-$C_6$)alkyl, ($C_1$-$C_6$)alkanoyl, or aryl($C_1$-$C_6$)alkyl; or $R_{a1}$ and $R_{b1}$ together with the nitrogen to which they are attached form an N-linked heterocycle containing from 3 to 10 atoms that is optionally substituted with one or more oxo;
each $R_{c1}$ is halo($C_1$-$C_6$)alkyl, ($C_1$-$C_6$)alkoxy or aryl($C_1$-$C_6$)alkoxy; and
each $R_{z1}$ is independently H or ($C_1$-$C_3$)alkyl
or a salt thereof.

8. A compound of formula Id:

Id wherein:
X is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —$NR_aR_b$, —C(=O)$NR_aR_b$, or —$NR_aC$(=O)—$R_c$; wherein each ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, and ($C_1$-$C_6$)alkoxycarbonyl of X is optionally substituted with one or more groups independently selected from hydroxy, halo, cyano, nitro, ($C_1$-$C_3$)alkoxy, ($C_1$-$C_3$)alkanoyl, ($C_1$-$C_3$)alkanoyloxy, ($C_1$-$C_3$)alkoxycarbonyl, —$NR_aR_b$, —C(=O)$NR_aR_b$, and —$NR_aC$(=O)—$R_c$;
Y is H, hydroxy, halo, cyano, nitro, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkanoyl, ($C_1$-$C_6$)alkanoyloxy, ($C_1$-$C_6$)alkoxycarbonyl, —NR$_a$R$_b$, —C(=O)NR$_a$R$_b$, or —NR$_a$C(=O)—R$_c$; wherein each (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, and (C$_1$-C$_6$)alkoxycarbonyl of Y is optionally substituted with one or more groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_a$R$_b$, —C(=O)NR$_a$R$_b$, and —NR$_a$C(=O)—R$_c$;

Q is CH or N;

R is CH or N;

p is 0, 1, 2, 3, or 4;

each R$^1$ is independently H or (C$_1$-C$_6$)alkyl wherein any (C$_1$-C$_6$)alkyl of R$^1$ is optionally is optionally substituted with one or more groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_{a1}$R$_{b1}$, —C(=O)NR$_{a1}$R$_{b1}$ and —NR$_{a1}$C(=O)—R$_{c1}$;

each R$_a$ and R$_b$ is independently H, (C$_1$-C$_6$)alkyl, (C$_1$-C$_6$)alkanoyl, or aryl(C$_1$-C$_6$)alkyl; or R$_a$ and R$_b$ together with the nitrogen to which they are attached form an N-linked heterocycle containing from 3 to 10 atoms that is optionally substituted with one or more oxo;

each R$_c$ is (C$_1$-C$_3$)haloalkyl;

each R$_d$ and R$_e$ is independently H or (C$_1$-C$_6$)alkyl;

each R$_{a1}$ and R$_{b1}$ is independently H, (C$_1$-C$_6$)alkyl, (C$_1$-C$_6$)alkanoyl, or aryl(C$_1$-C$_6$)alkyl; or R$_{a1}$ and R$_{b1}$ together with the nitrogen to which they are attached form an N-linked heterocycle containing from 3 to 10 atoms that is optionally substituted with one or more oxo;

each R$_{c1}$ is halo(C$_1$-C$_6$)alkyl, (C$_1$-C$_6$)alkoxy or aryl(C$_1$-C$_6$)alkoxy; and each R$_{e1}$ is independently H or (C$_1$-C$_3$)alkyl or a salt thereof.

9. A compound of formula Ie or formula If:

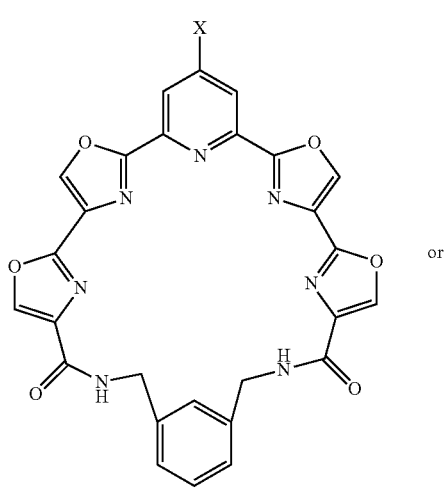

Ie

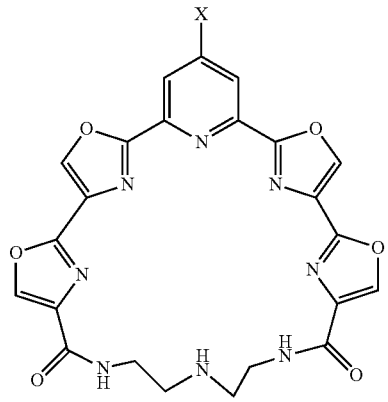

If wherein:

X is H, hydroxy, halo, cyano, nitro, (C$_1$-C$_6$)alkyl, (C$_2$-C$_6$)alkenyl, (C$_2$-C$_6$)alkynyl, C$_1$-C$_6$)alkoxy, (C$_1$-C$_6$)alkanoyl, (C$_1$-C$_6$)alkanoyloxy, (C$_1$-C$_6$)alkoxycarbonyl, —NR$_a$R$_b$. —C(=O)NR$_a$R$_b$, or —NR$_a$C(=O)—R$_c$; wherein each (C$_1$-C$_6$)alkyl, (C$_2$-C$_6$)alkenyl, (C$_2$-C$_6$)alkynyl, (C$_1$-C$_6$)alkoxy, (C$_1$-C$_6$)alkanoyl, (C$_1$-C$_6$)alkanoyloxy, and (C$_1$-C$_6$)alkoxycarbonyl of X is optionally substituted with one or more groups independently selected from hydroxy, halo, cyano, nitro, (C$_1$-C$_3$)alkoxy, (C$_1$-C$_3$)alkanoyl, (C$_1$-C$_3$)alkanoyloxy, (C$_1$-C$_3$)alkoxycarbonyl, —NR$_a$R$_b$, —C(=O)NR$_a$R$_b$, and —NR$_a$C(=O)—R$_c$;

each R$_a$ and R$_b$ is independently H, (C(C$_1$-C$_6$)alkanoyl, or aryl(C$_1$-C$_6$)alkyl; or R$_a$ and R$_b$ together with the nitrogen to which they are attached form an N-linked heterocycle containing from 3 to 10 atoms that is optionally substituted with one or more oxo; and each R$_c$ is (C$_1$-C$_3$)haloalkyl;

or a salt thereof.

10. A pharmaceutical composition comprising a compound of formula (I) as defined in claim 1; or a pharmaceutically acceptable salt thereof; and a pharmaceutically acceptable carrier.

11. A therapeutic method for treating a cancer selected from a lymphoblastoma, a melanoma, and an epidermoid carcinoma comprising administering to a mammal in need of such therapy, an effective amount of a compound of formula (I) as defined in claim 1, or a pharmaceutically acceptable salt thereof.

12. A pharmaceutical composition comprising a compound of formula (I) as defined in claim 5; or a pharmaceutically acceptable salt thereof; and a pharmaceutically acceptable carrier.

13. A pharmaceutical composition comprising a compound of formula (I) as defined in claim 6; or a pharmaceutically acceptable salt thereof; and a pharmaceutically acceptable carrier.

14. A pharmaceutical composition comprising a compound of formula (I) as defined in claim 7; or a pharmaceutically acceptable salt thereof; and a pharmaceutically acceptable carrier.

15. A pharmaceutical composition comprising a compound of formula (I) as defined in claim 8; or a pharmaceutically acceptable salt thereof; and a pharmaceutically acceptable carrier.

16. A pharmaceutical composition comprising a compound of formula (I) as defined in claim 9; or a pharmaceutically acceptable salt thereof; and a pharmaceutically acceptable carrier.

* * * * *

UNITED STATES PATENT AND TRADEMARK OFFICE
CERTIFICATE OF CORRECTION

PATENT NO. : 8,796,300 B2
APPLICATION NO. : 13/508012
DATED : August 5, 2014
INVENTOR(S) : LaVoie et al.

It is certified that error appears in the above-identified patent and that said Letters Patent is hereby corrected as shown below:

On the Title Page

Item (73), Assignees

Replace:

Rutgers, the State University of New Jersey

With:

Rutgers, The State University of New Jersey

In the Claims

In Claim 1, Column 108, Line 10:

Replace:

is optionally is optionally

With:

is optionally

In Claim 1, Column 108, Line 13:

Replace:

$(C_1-C_6)$alkanoyl oxy

With:

$(C_1-C_6)$alkanoyloxy

Signed and Sealed this
Nineteenth Day of May, 2015

Michelle K. Lee
*Director of the United States Patent and Trademark Office*

In Claim 5, Column 111, Line 49:

Replace:

–C(=O)NR$_a$,R$_b$

With:

–C(=O)NR$_a$R$_b$

In Claim 5, Column 111, Line 62:

Replace:

–C(=O)NR$_a$, R$_b$

With:

–C(=O)NR$_a$R$_b$

In Claim 6, Column 112, Line 45:

Replace:

–C(=O)NR$_a$,R$_b$

With:

–C(=O)NR$_a$R$_b$

In Claim 6, Column 112, Line 58:

Replace:

–C(=O)NR$_a$,R$_b$

With:

–C(=O)NR$_a$R$_b$

In Claim 7, Column 113, Line 43:

Replace:

–C(=O)NR$_a$,R$_b$

With:

–C(=O)NR$_a$R$_b$

In Claim 7, Column 113, Line 57:

Replace:

–C(=O)NR$_a$,R$_b$

With:

–C(=O)NR$_a$R$_b$

CERTIFICATE OF CORRECTION (continued)
U.S. Pat. No. 8,796,300 B2

In Claim 7, Column 114, Line 3:

Replace:

is optionally is optionally

With:

is optionally

In Claim 8, Column 114, Line 55:

Replace:

–C(=O)NR$_a$,R$_b$

With:

–C(=O)NR$_a$R$_b$

In Claim 8, Column 114, Line 63:

Replace:

–C(=O)NR$_a$,R$_b$

With:

–C(=O)NR$_a$R$_b$

In Claim 8, Column 115, Line 1:

Replace:

–C(=O)NR$_a$,R$_b$

With:

–C(=O)NR$_a$R$_b$

In Claim 8, Column 115, Line 9:

Replace:

–C(=O)NR$_a$,R$_b$

With:

–C(=O)NR$_a$R$_b$

In Claim 9, Column 116, Line 24:

Replace:

–NR$_a$R$_b$.

With:

–NR$_a$R$_b$,

In Claim 9, Column 116, Line 33:

Replace:

H, (((C($C_1$-$C_6$)alkanoyl,

With:

H, ($C_1$-$C_6$)alkyl, ($C_1$-$C_6$)alkanoyl,